US010661014B2

(12) United States Patent
Sarkinen et al.

(10) Patent No.: US 10,661,014 B2
(45) Date of Patent: May 26, 2020

(54) INJECTION DEVICE HAVING VARIABLE DOSING

(71) Applicant: Antares Pharma, Inc., Ewing, NJ (US)

(72) Inventors: Bryan James Sarkinen, St. Louis Park, MN (US); Michael Travanty, Minneapolis, MN (US); Patrick Madsen, Litchfield, MN (US); Andrew Charles Mork, Minneapolis, MN (US)

(73) Assignee: Antares Pharma, Inc., Ewing, NJ (US)

( * ) Notice: Subject to any disclaimer, the term of this patent is extended or adjusted under 35 U.S.C. 154(b) by 256 days.

(21) Appl. No.: 15/545,358

(22) PCT Filed: Jan. 21, 2016

(86) PCT No.: PCT/US2016/014217
§ 371 (c)(1),
(2) Date: Jul. 21, 2017

(87) PCT Pub. No.: WO2016/118688
PCT Pub. Date: Jul. 28, 2016

(65) Prior Publication Data
US 2018/0001025 A1 Jan. 4, 2018

Related U.S. Application Data

(60) Provisional application No. 62/140,023, filed on Mar. 30, 2015, provisional application No. 62/116,836, (Continued)

(51) Int. Cl.
*A61M 5/20* (2006.01)
*A61M 5/31* (2006.01)
(Continued)

(52) U.S. Cl.
CPC ........ *A61M 5/2033* (2013.01); *A61M 5/3146* (2013.01); *A61M 5/3156* (2013.01);
(Continued)

(58) Field of Classification Search
CPC .............. A61M 5/2033; A61M 5/3156; A61M 5/31553; A61M 5/3146;
(Continued)

(56) References Cited

U.S. PATENT DOCUMENTS 4,636,198 A 1/1987 Stade
5,308,340 A 5/1994 Harris
(Continued)

FOREIGN PATENT DOCUMENTS

GB 2304060 A 3/1997
JP 2007509726 4/2007

OTHER PUBLICATIONS

Canadian Patent Application No. 2973592; Office Action dated May 17, 2018, 5 pages.
(Continued)

*Primary Examiner* — Amber R Stiles
(74) *Attorney, Agent, or Firm* — Morgan, Lewis & Bockius LLP

(57) ABSTRACT

An injection device for injecting medicament in a patient comprises a housing configured to house a fluid reservoir that has one of a plurality of volumes of medicament. An injection conduit fluidly coupled to the fluid reservoir defines a fluid pathway from the fluid reservoir to the patient. A firing mechanism is coupled to the fluid reservoir and is configured to expel the medicament from the fluid reservoir through the injection conduit. A volume setting mechanism is coupled to the firing mechanism and is configured to select the one of the plurality of volumes of medicament for the firing mechanism to expel. A dose setting mechanism is configured to select all or a fraction of the one of the plurality of volumes of medicament that is injected from the injection conduit when the firing mechanism is actuated.

39 Claims, 40 Drawing Sheets

Related U.S. Application Data filed on Feb. 16, 2015, provisional application No. 62/105,897, filed on Jan. 21, 2015.

(51) Int. Cl.
*A61M 5/315* (2006.01)
*A61M 5/32* (2006.01)
*A61M 5/48* (2006.01)

(52) U.S. Cl.
CPC .... *A61M 5/31536* (2013.01); *A61M 5/31553* (2013.01); *A61M 5/2053* (2013.01); *A61M 5/3204* (2013.01); *A61M 5/482* (2013.01); *A61M 2005/2013* (2013.01); *A61M 2005/2073* (2013.01); *A61M 2005/3154* (2013.01); *A61M 2207/00* (2013.01)

(58) Field of Classification Search
CPC .. A61M 2005/2073; A61M 2005/2013; A61M 5/3204; A61M 5/2053; A61M 2207/00; A61M 5/482
See application file for complete search history.

(56) References Cited

U.S. PATENT DOCUMENTS

| | | |
|---|---|---|
| 2001/0005781 A1 | 6/2001 | Bergens et al. |
| 2002/0173752 A1 | 11/2002 | Polzin |
| 2006/0270985 A1 | 11/2006 | Hommann et al. |
| 2008/0269671 A1 | 10/2008 | Lin et al. |
| 2009/0299278 A1 | 12/2009 | Lesch et al. |
| 2010/0010454 A1 | 1/2010 | Marshall et al. |
| 2011/0034881 A1 | 2/2011 | Bartha |
| 2012/0283660 A1 | 11/2012 | Jones et al. |
| 2013/0030409 A1 | 1/2013 | Macdonald et al. |
| 2013/0245565 A1 | 9/2013 | Leak et al. |
| 2013/0324965 A1* | 12/2013 | Lawlis ................ A61K 38/24 604/506 |
| 2014/0107587 A1 | 4/2014 | Hogdahl |
| 2014/0350484 A1* | 11/2014 | Kohlbrenner .......... A61M 5/24 604/222 |

OTHER PUBLICATIONS

International Preliminary Report on Patentability dated Jul. 25, 2017 for International Patent Application No. PCT/US2016/014217, 7 pp.
Search Report for European Patent Application No. 16740721.2, 4 pages.
Written Opinion dated May 17, 2016 for International Patent Application No. PCT/US2016/014217, 6 pp.
International Search Report dated May 17, 2016 for International Patent Application No. PCT/US2016/014217, 3 pp.
European Office Action dated Sep. 30, 2019 for European Patent Application No. 16740721.2, 4 pages.
Japanese Office Action for Japanese Patent Application No. 2017-538305 dated Dec. 6, 2019, 5 pages.

* cited by examiner

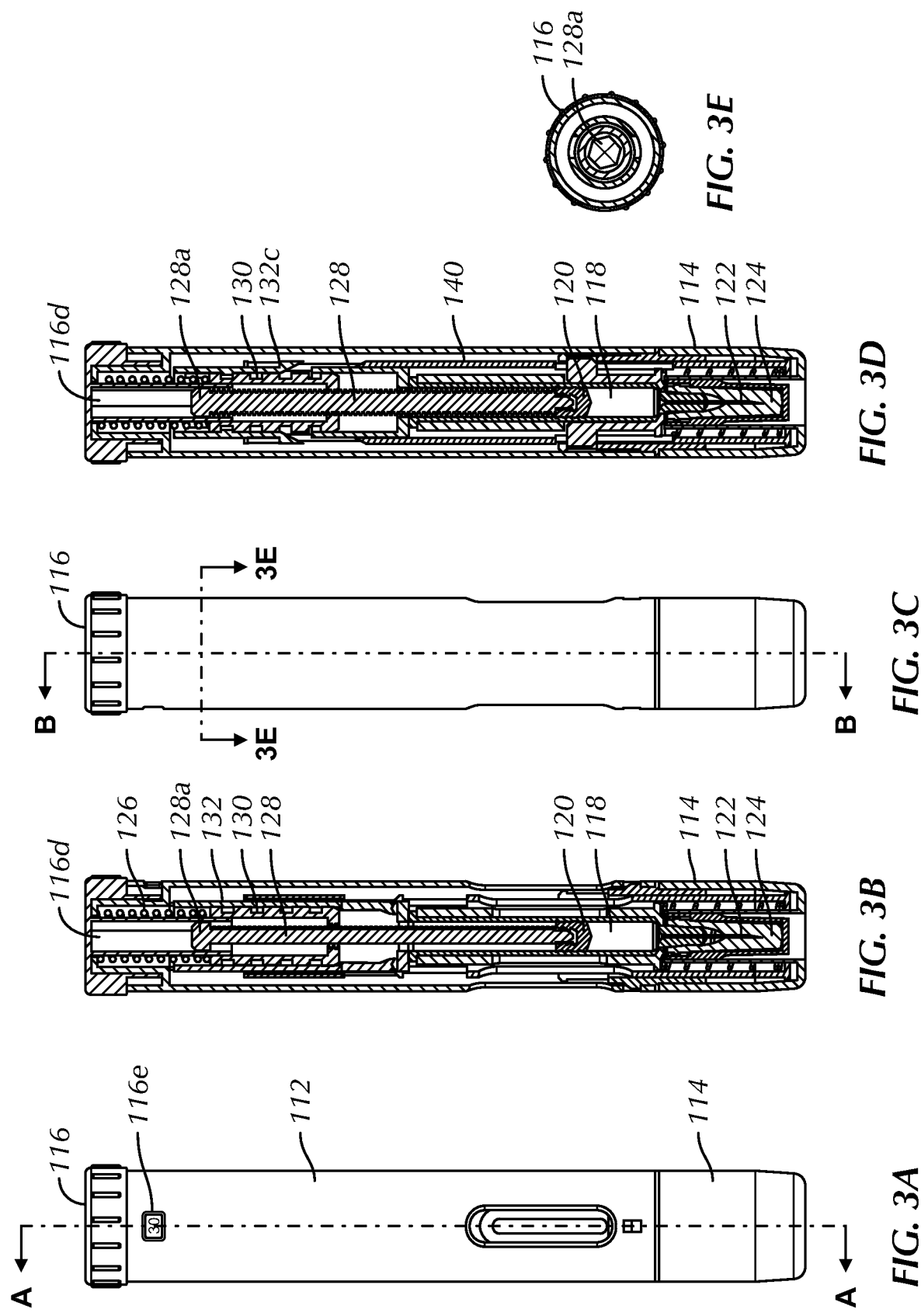

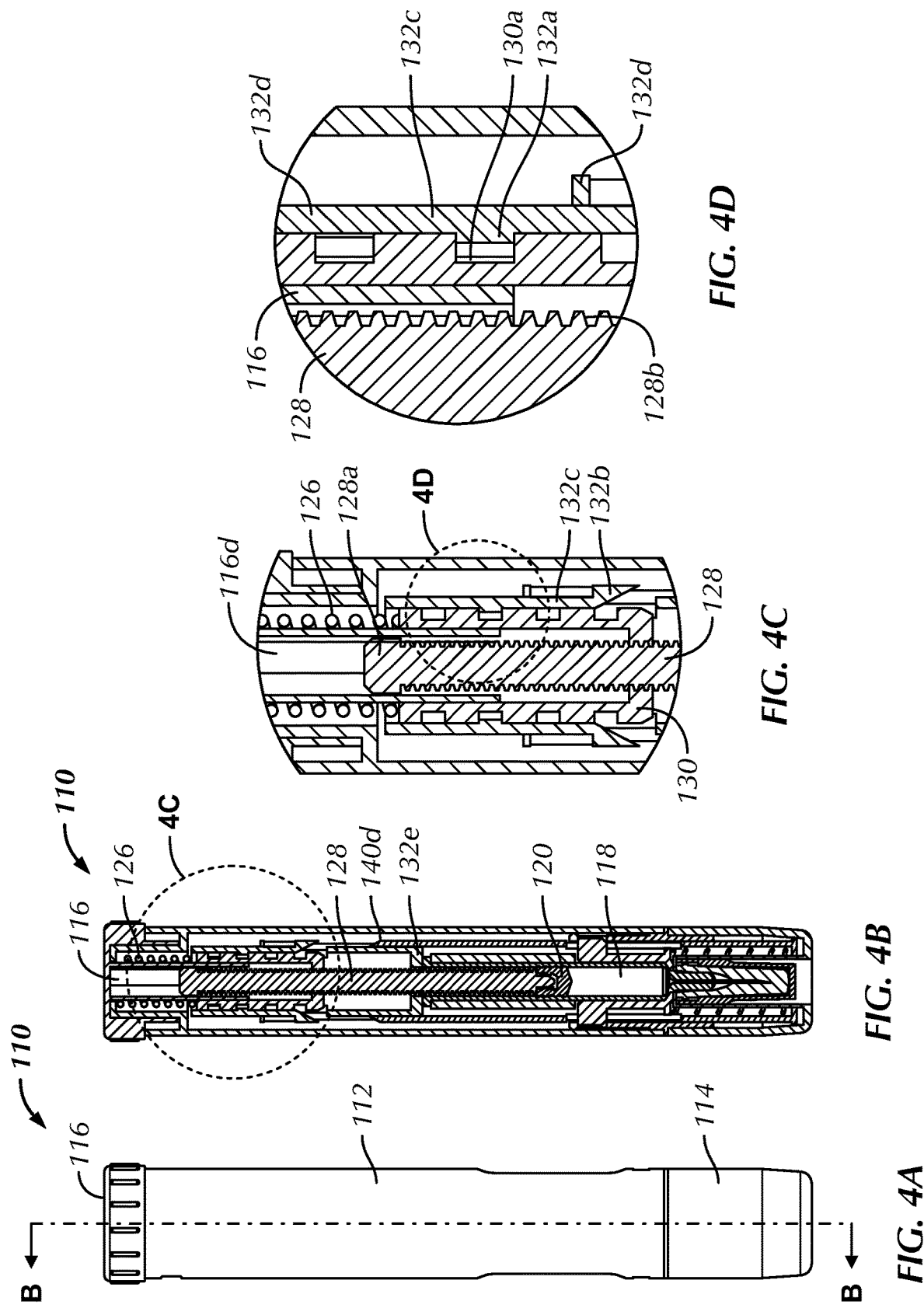

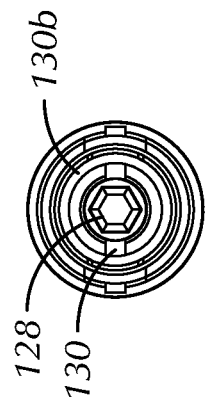
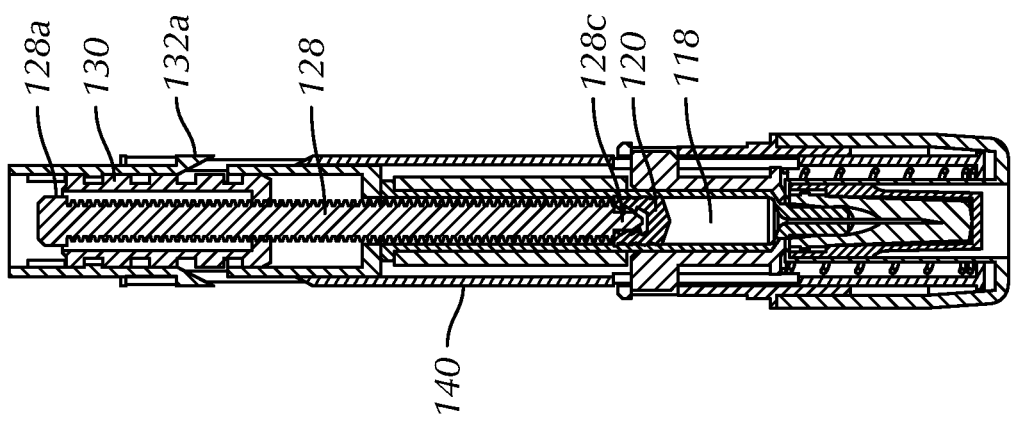
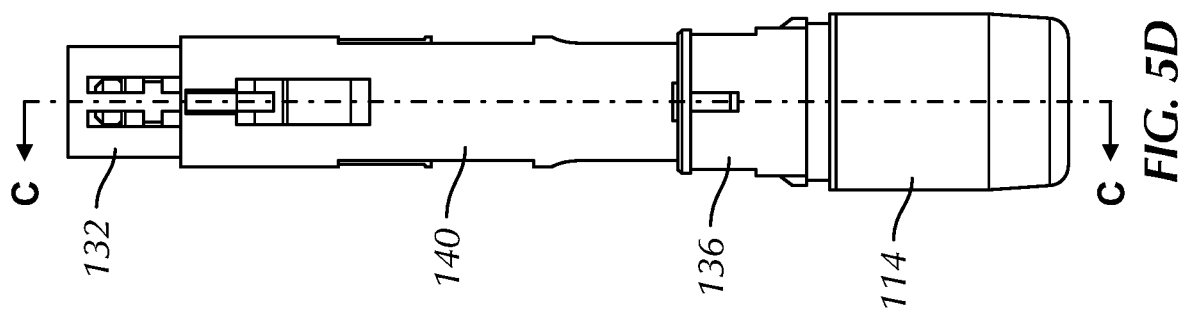
FIG. 5F
FIG. 5E
FIG. 5D

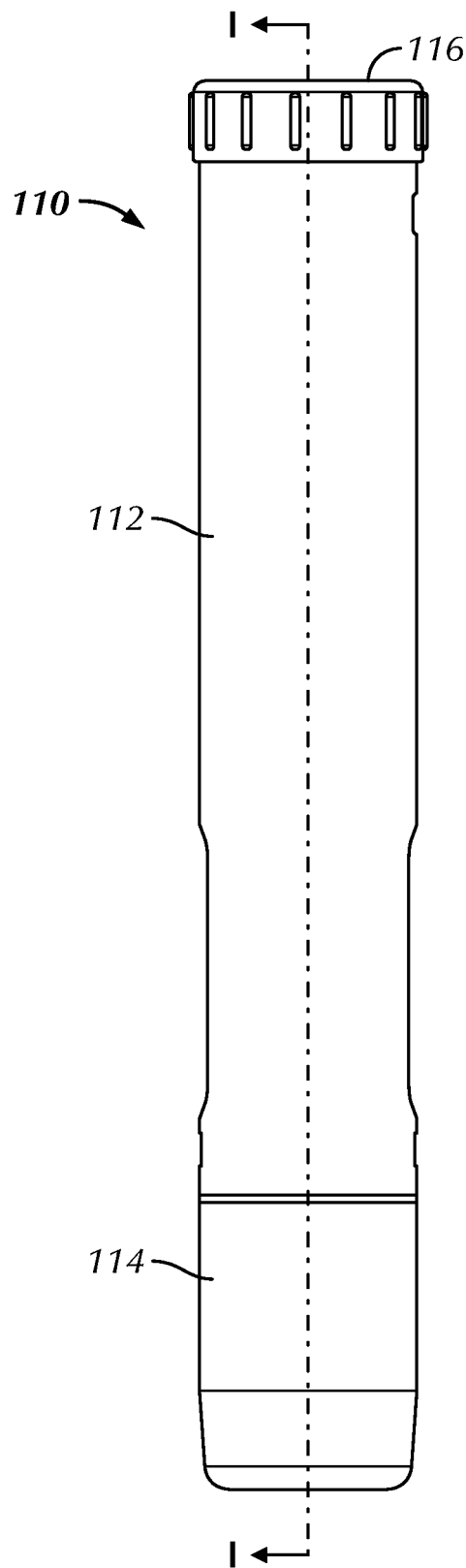
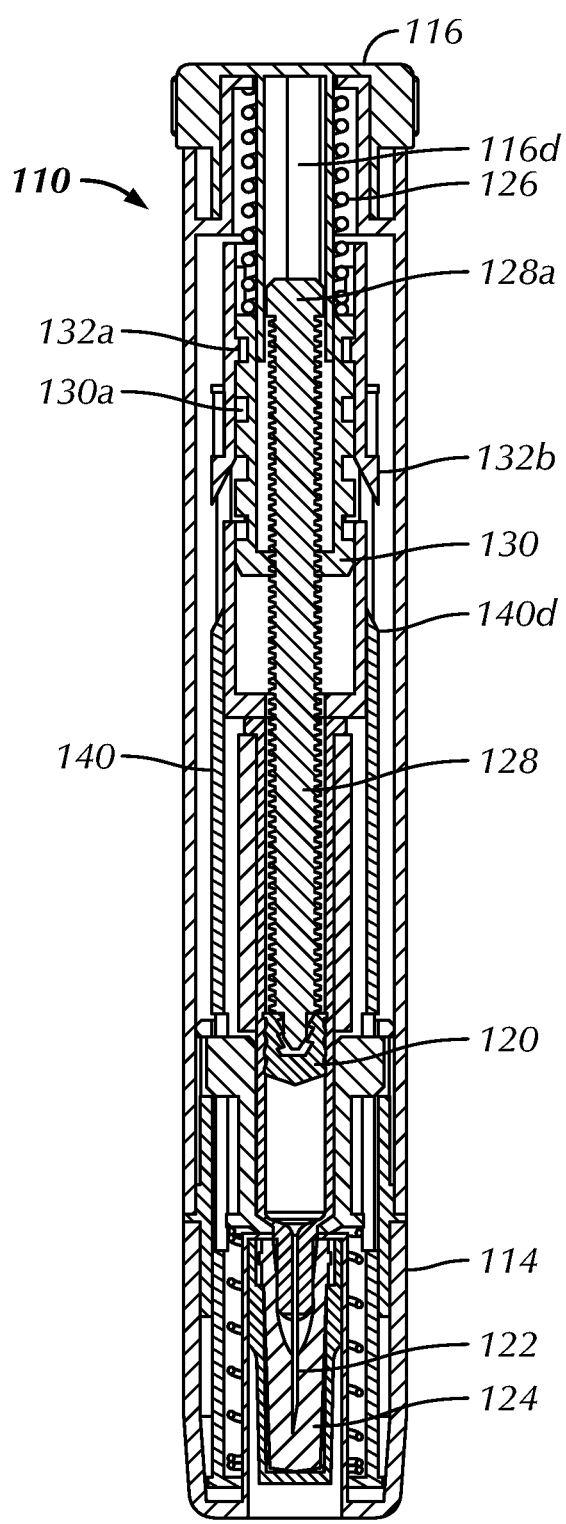
FIG. 6A
FIG. 6B

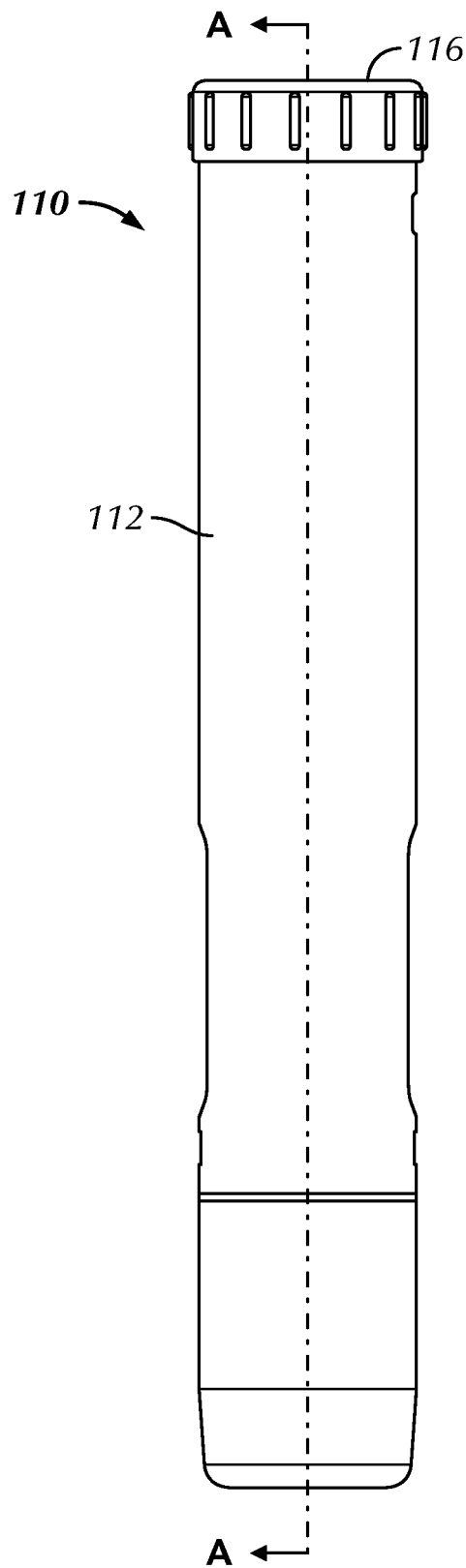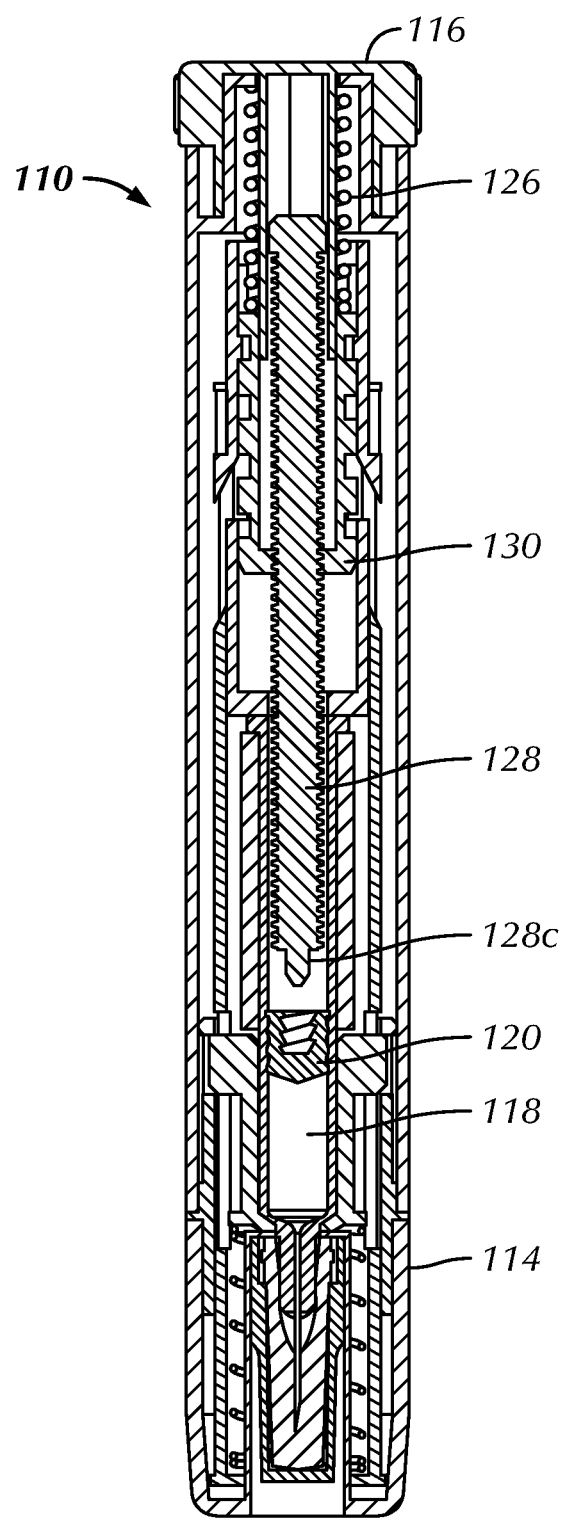
FIG. 7A
FIG. 7B

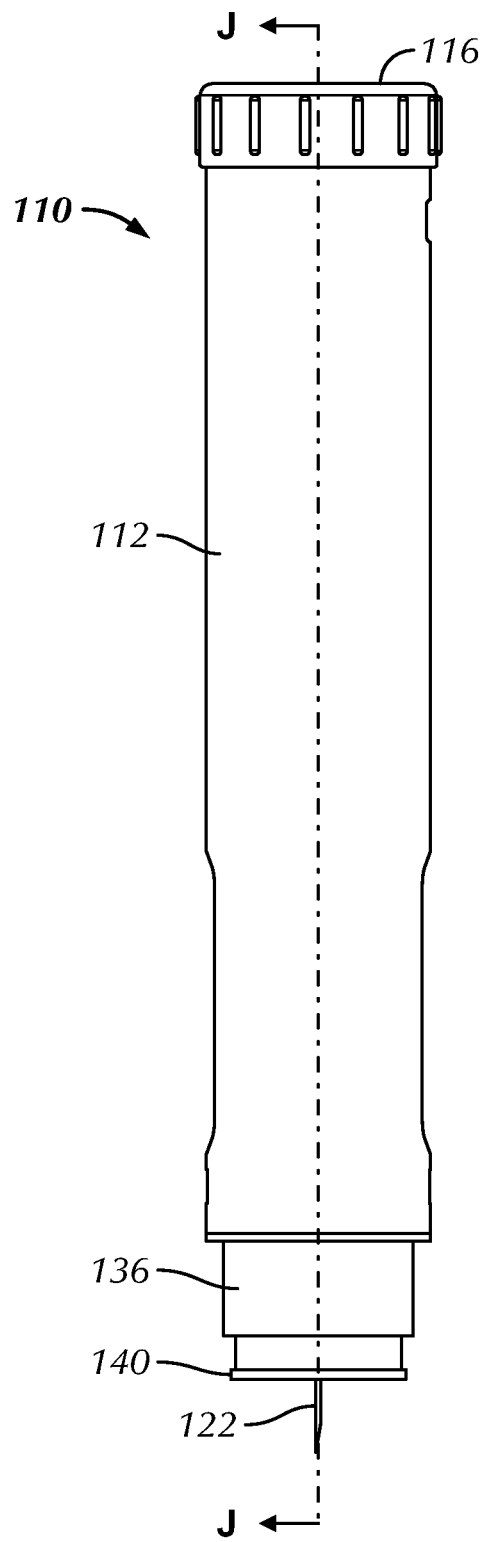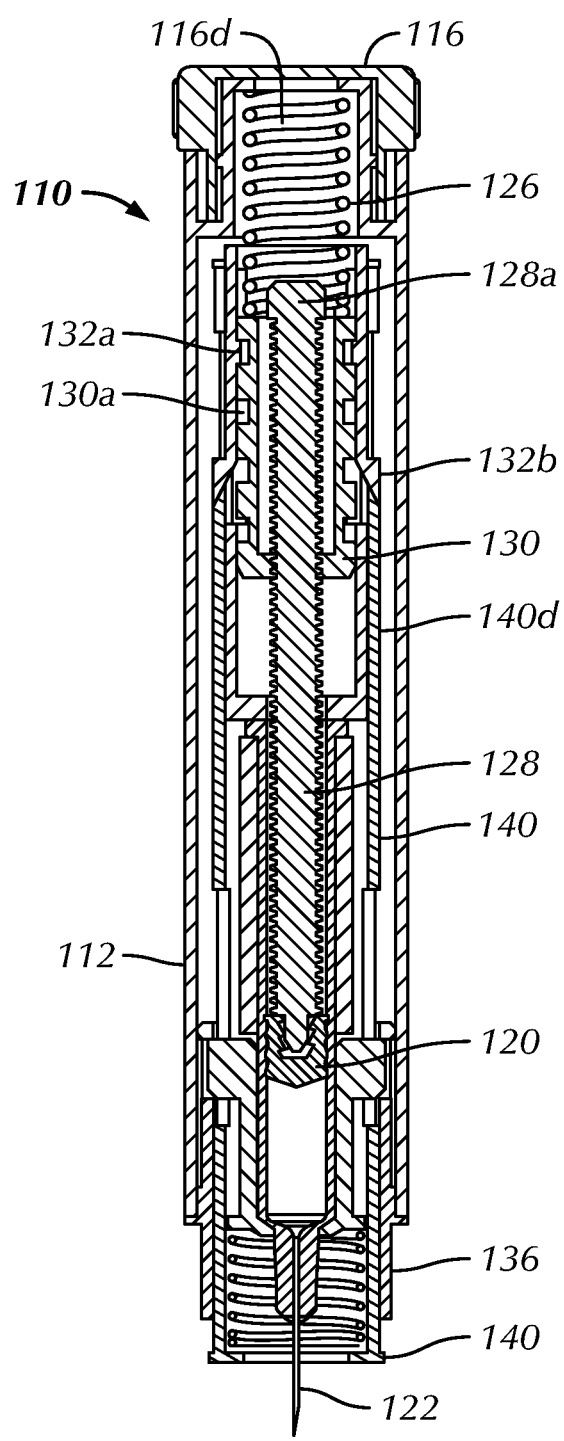
FIG. 8A
FIG. 8B

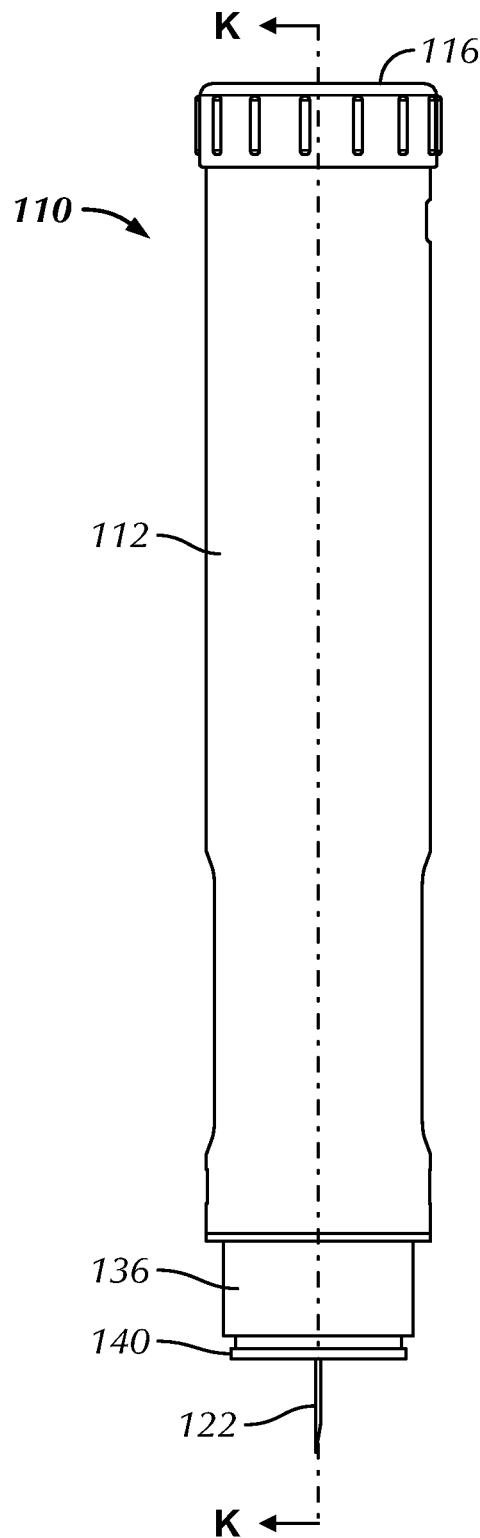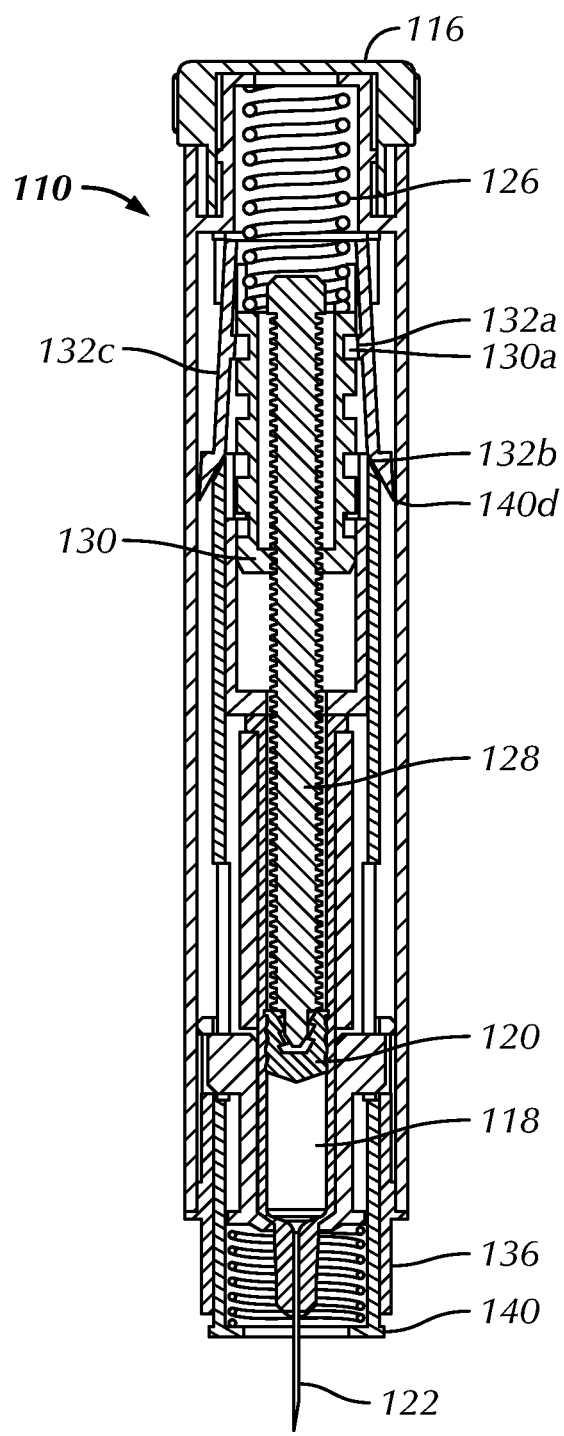
FIG. 9A
FIG. 9B

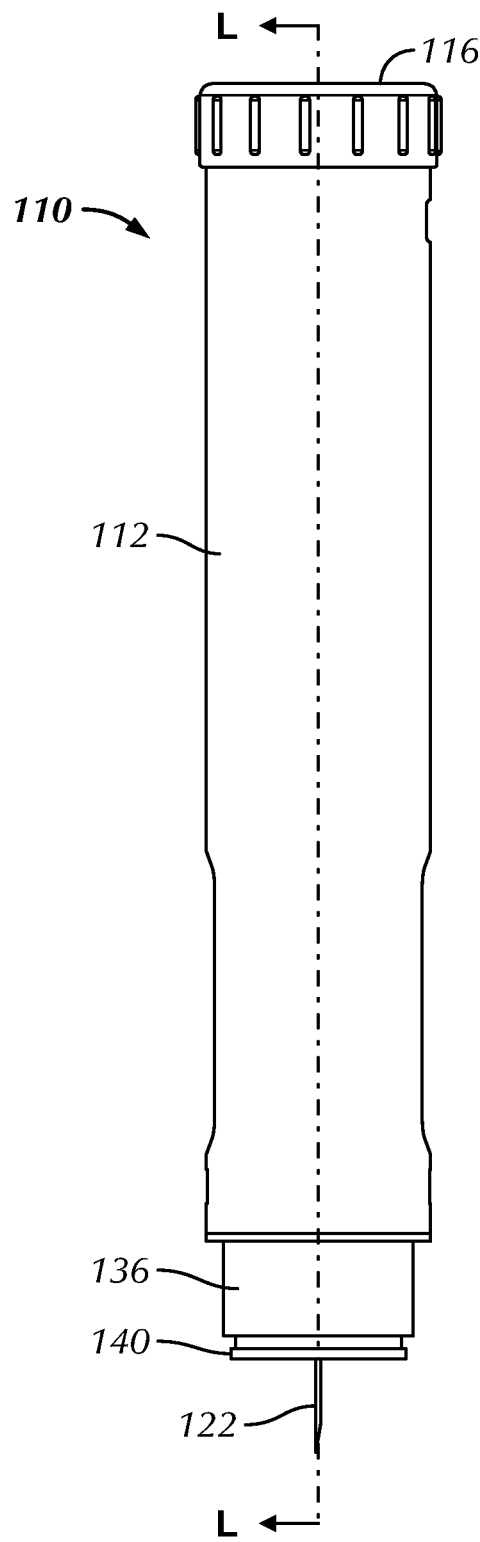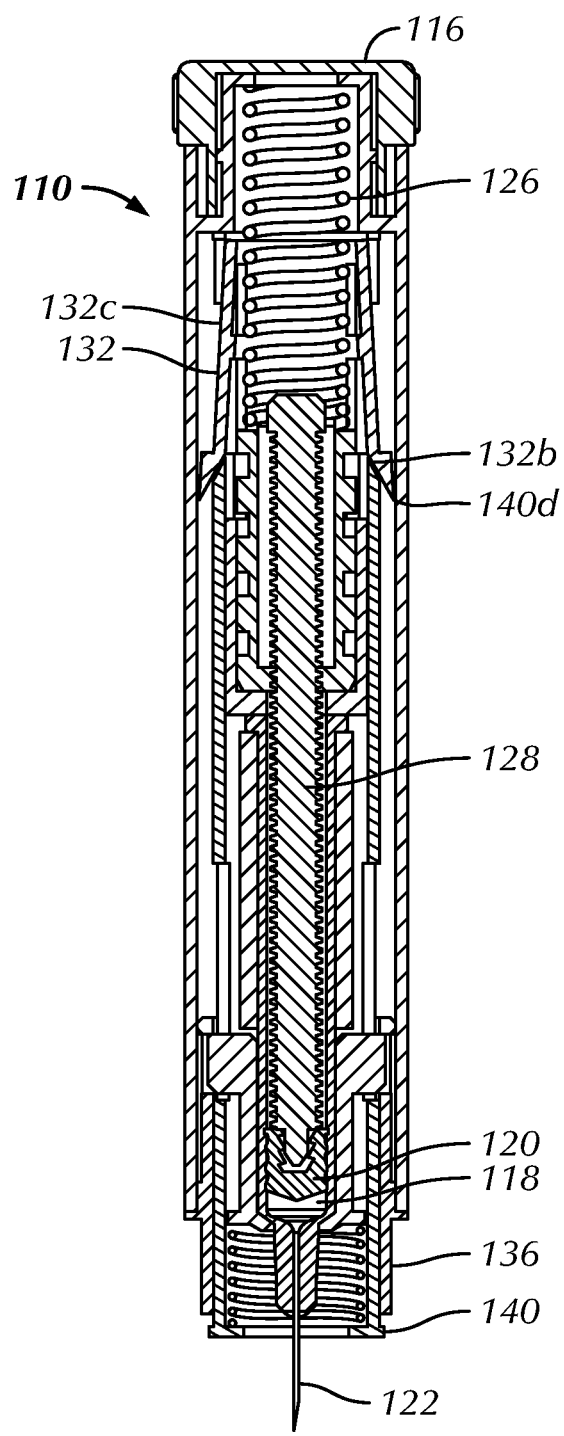
FIG. 10A
FIG. 10B

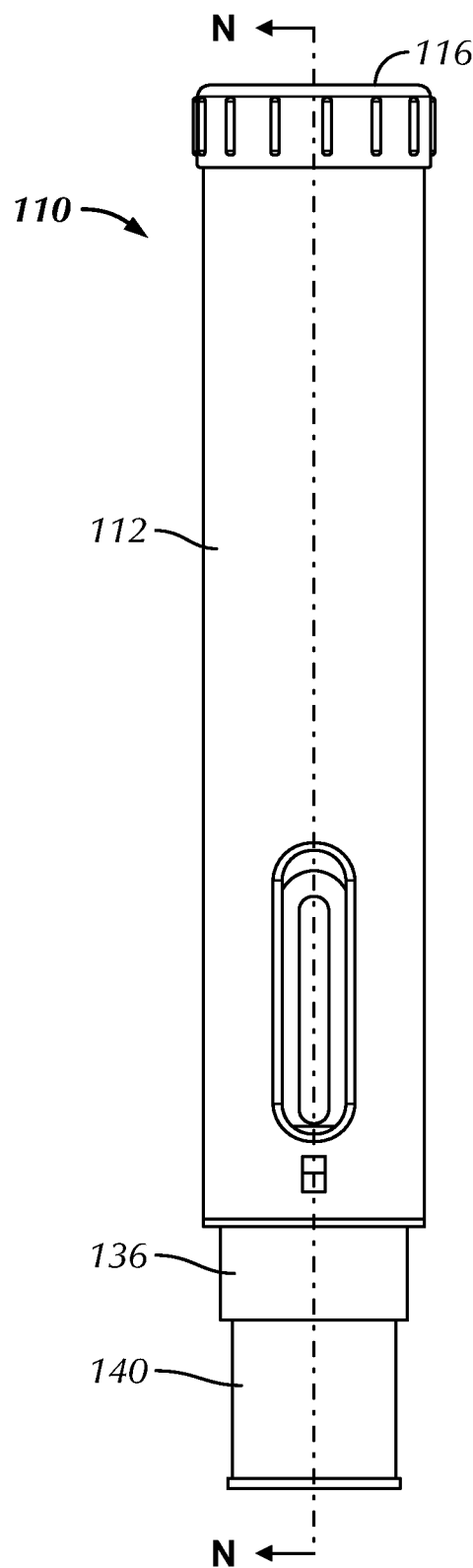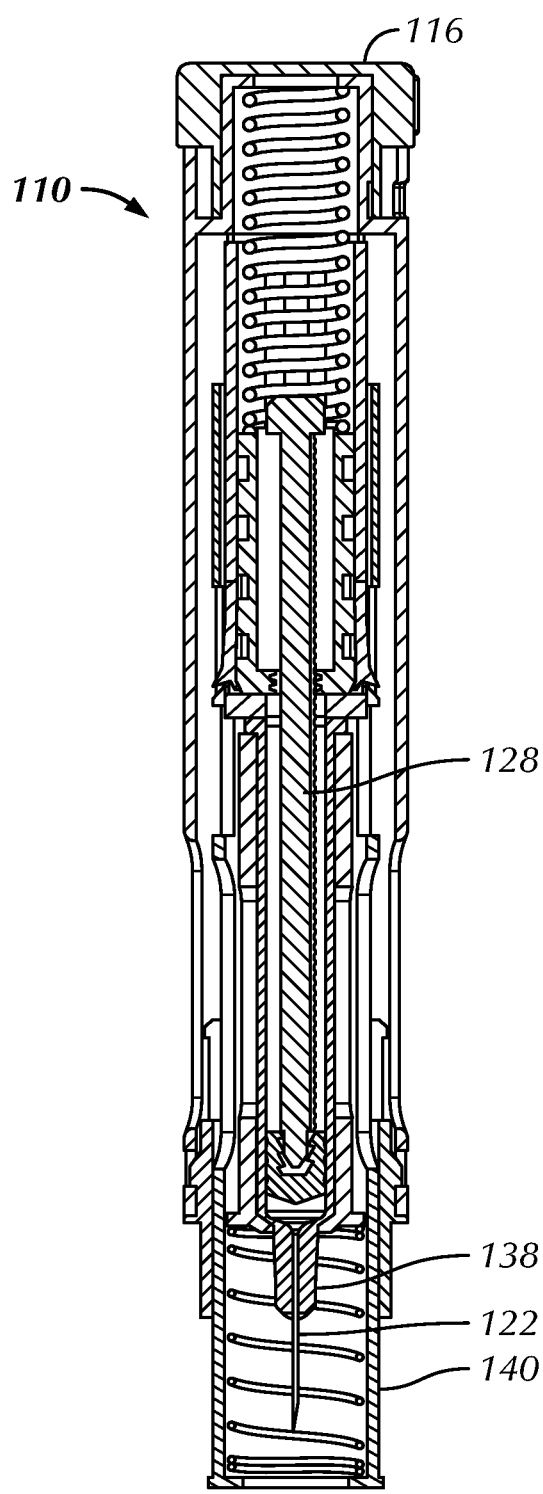
FIG. 12A
FIG. 12B

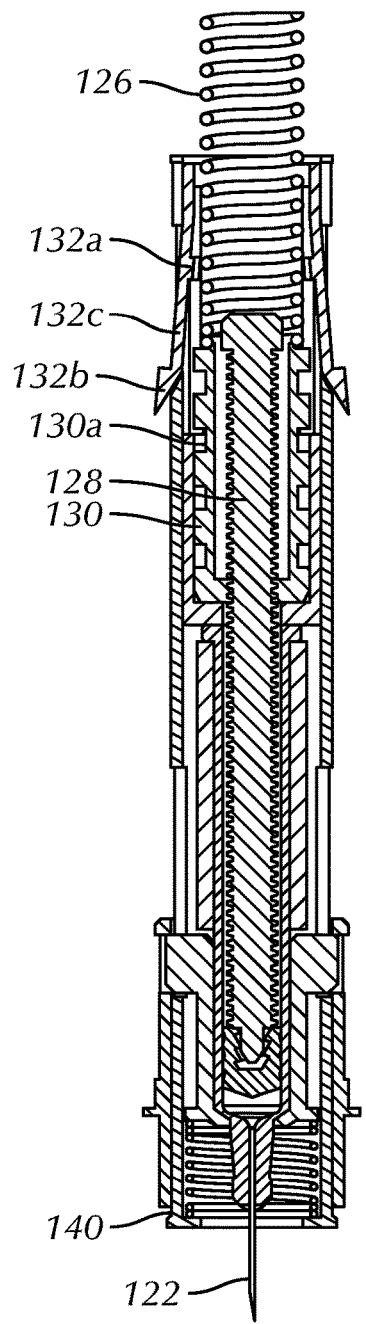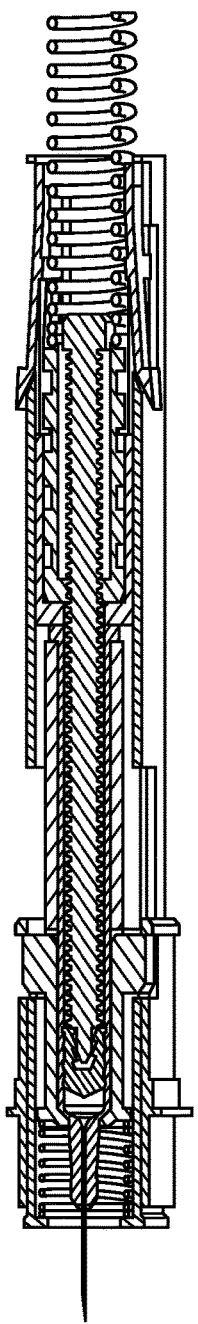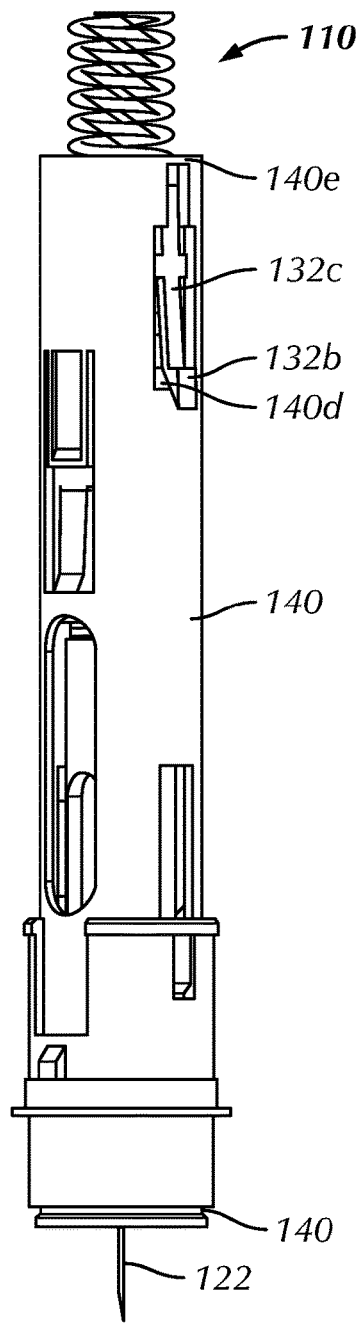
*FIG. 16A*    *FIG. 16B*    *FIG. 16C*

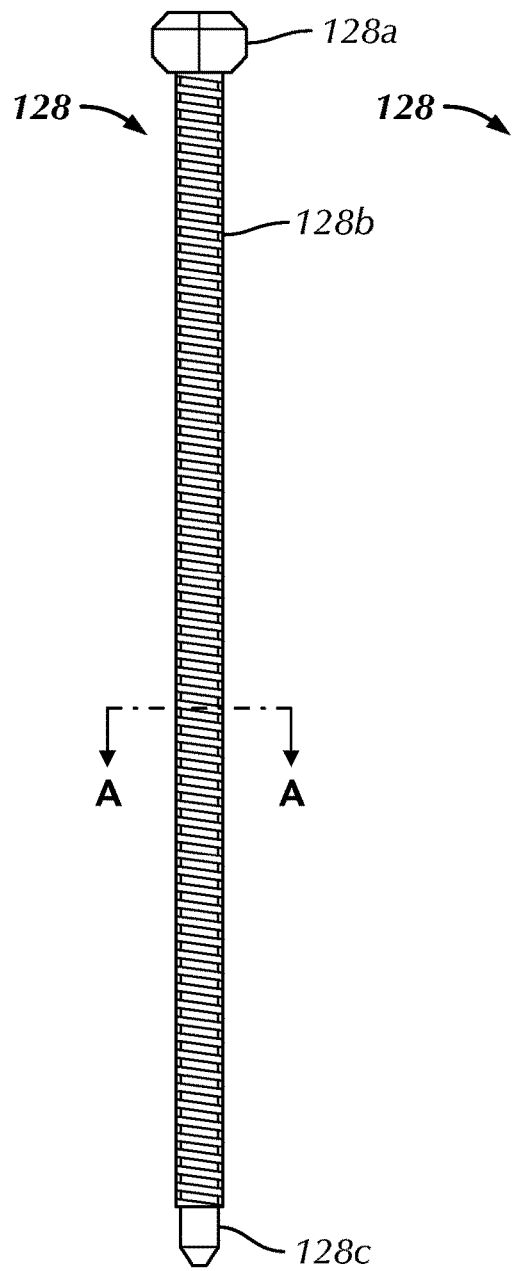
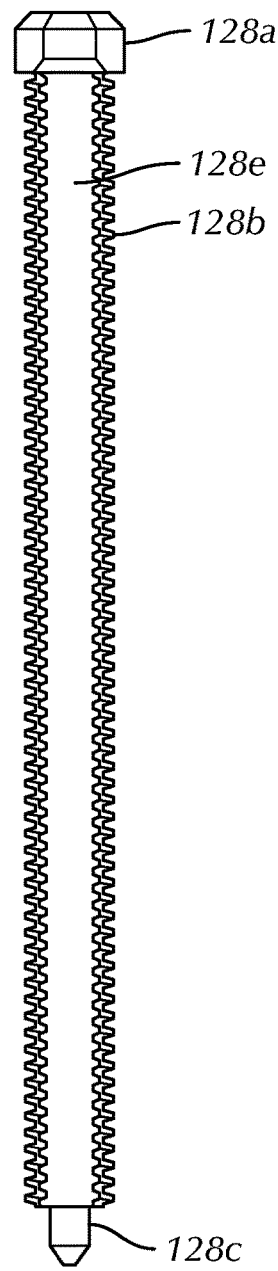
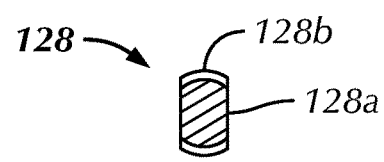
FIG. 18C
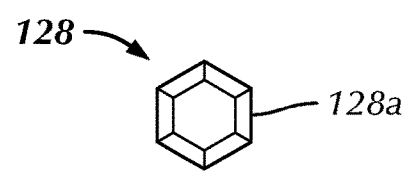
FIG. 18D
FIG. 18A          FIG. 18B

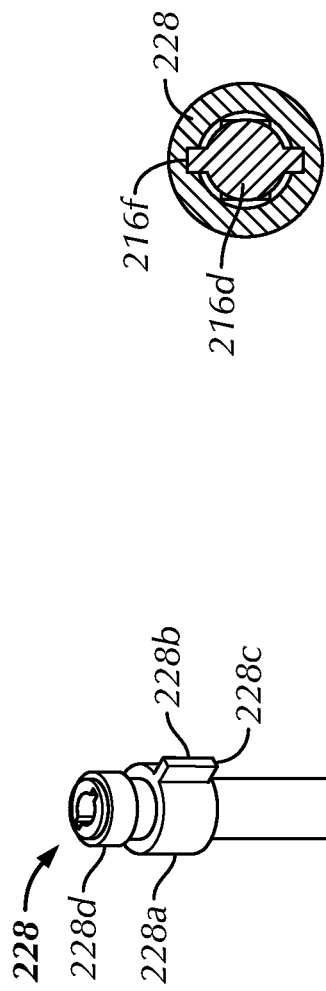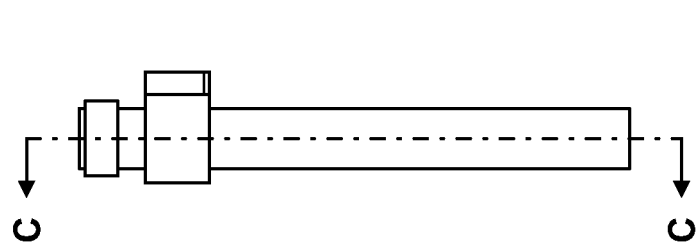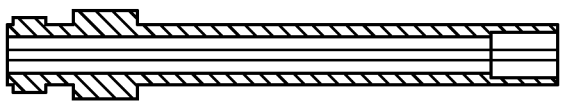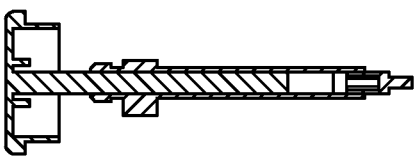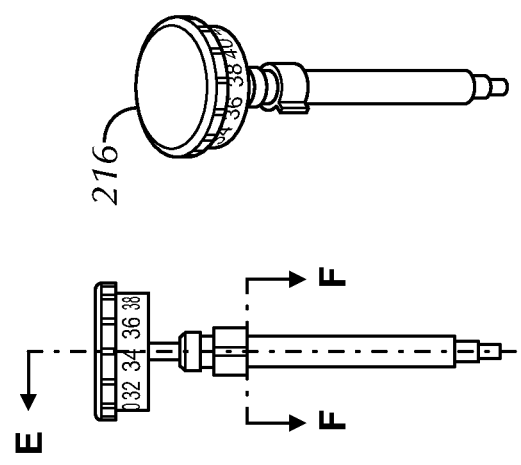

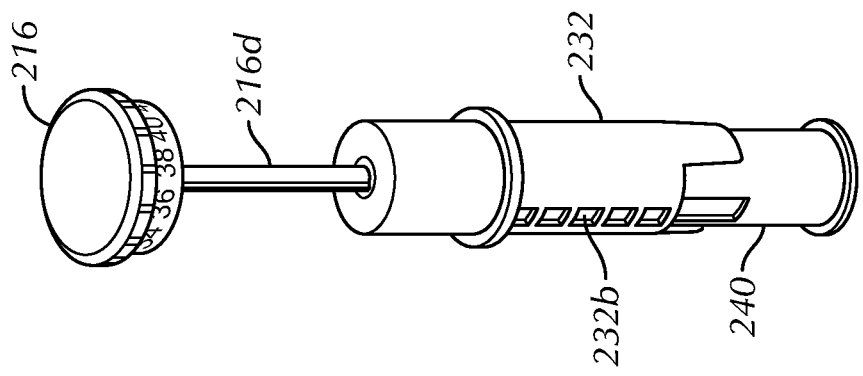
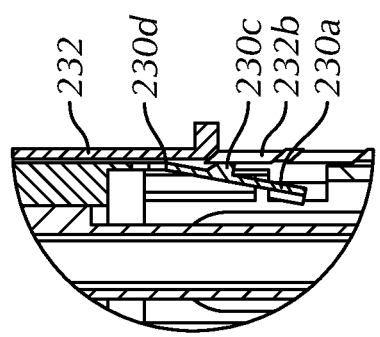
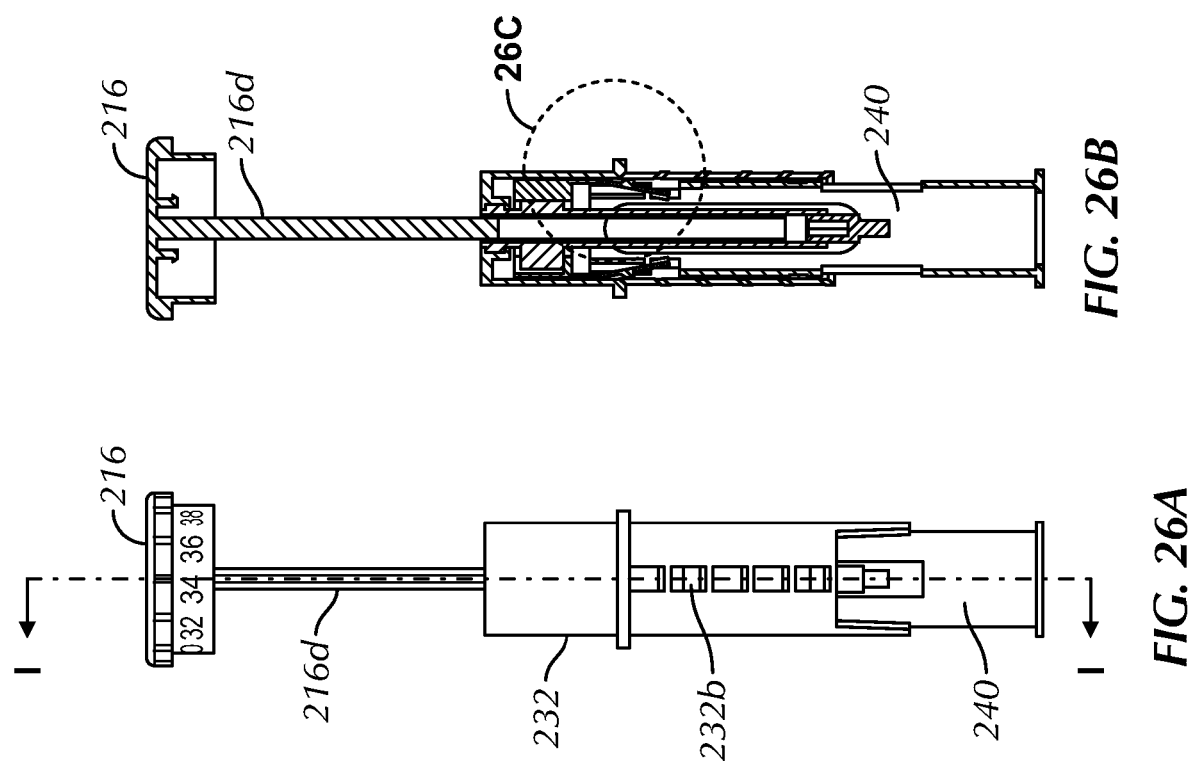
FIG. 26A  FIG. 26B  FIG. 26C  FIG. 26D

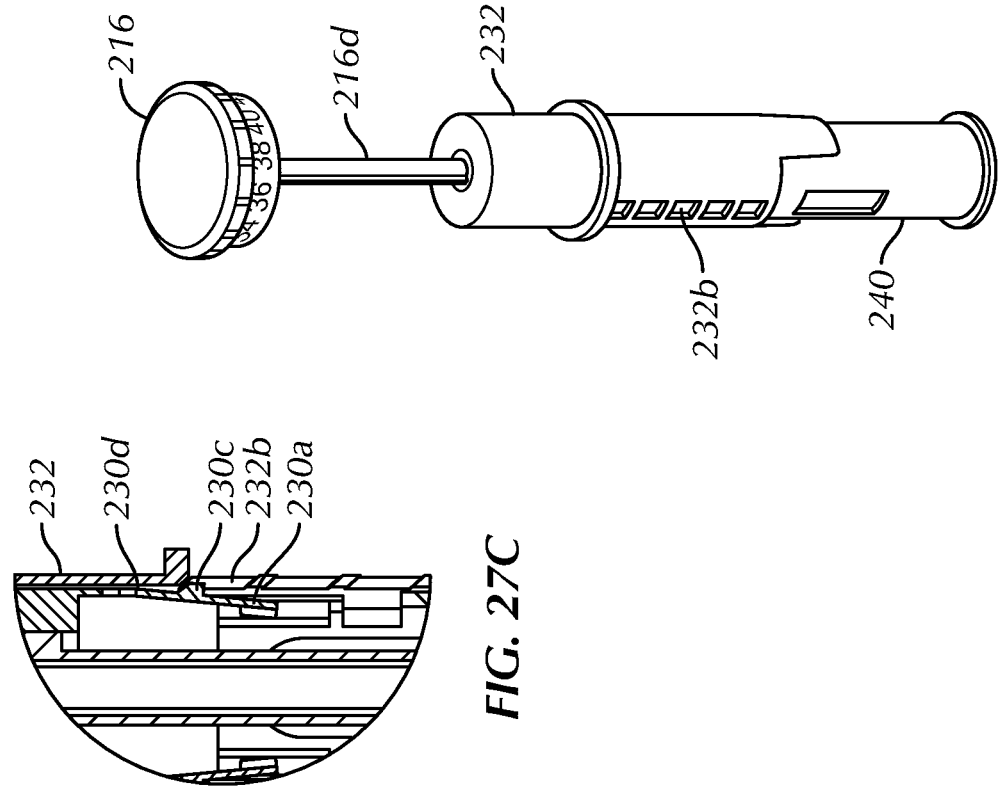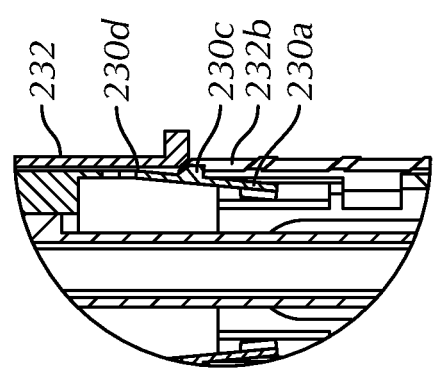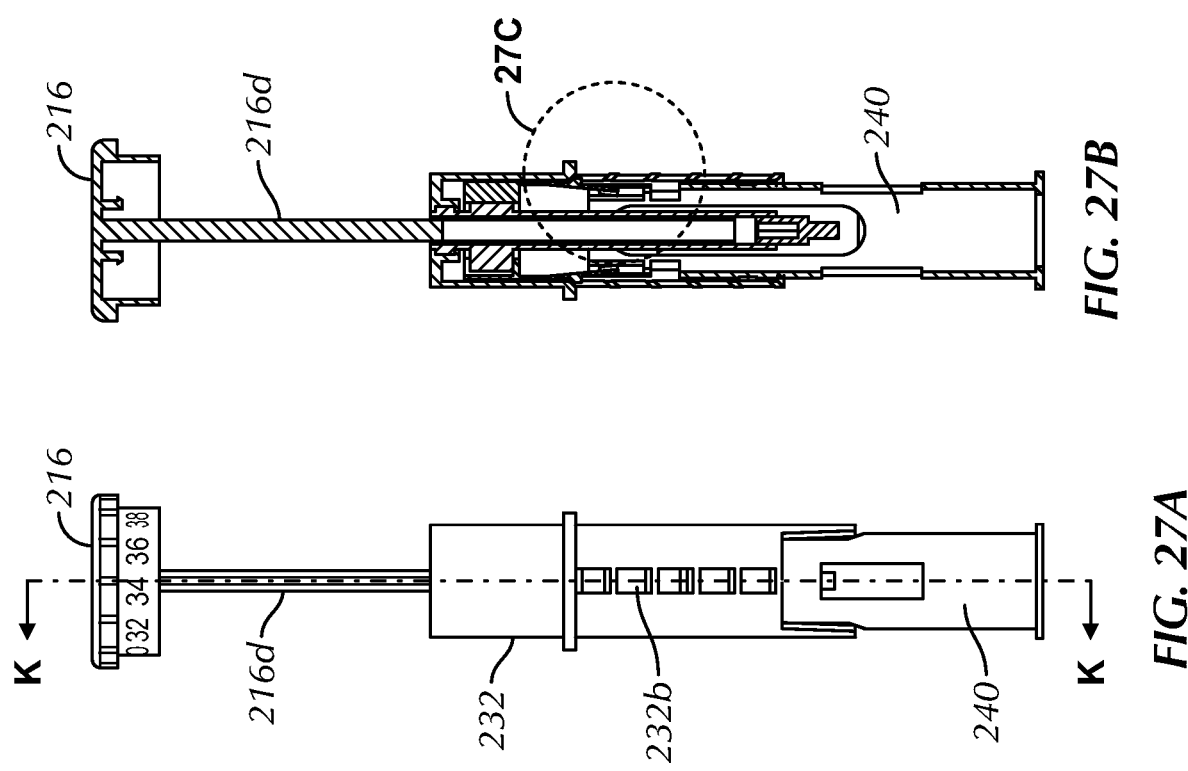
FIG. 27A  FIG. 27B  FIG. 27C  FIG. 27D

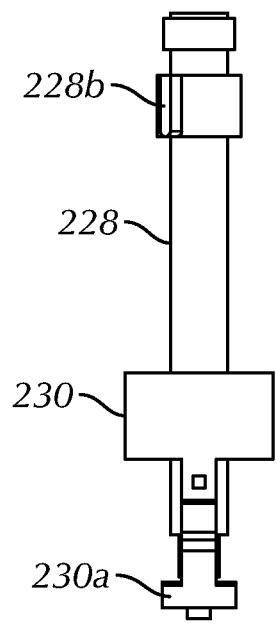
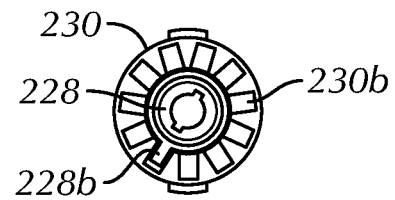
FIG. 28A
FIG. 28B
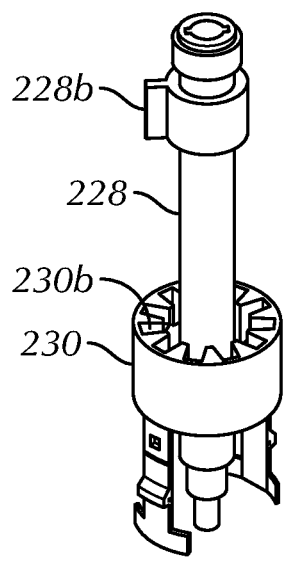
FIG. 28C
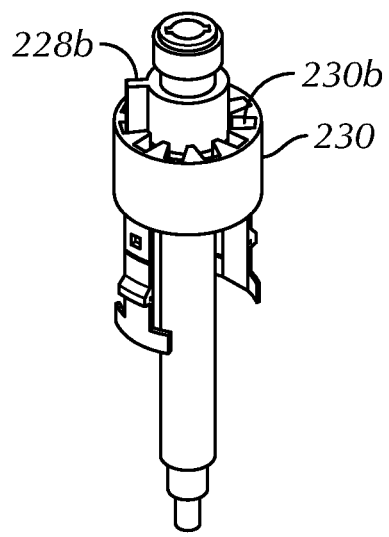
FIG. 29

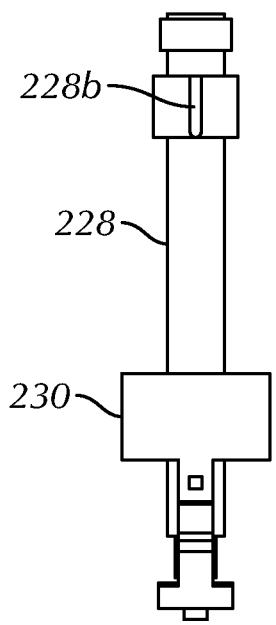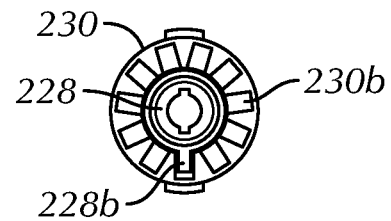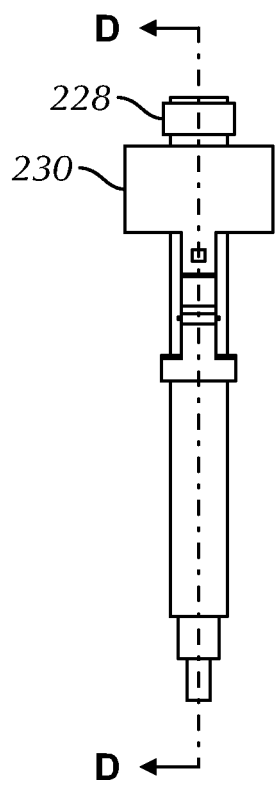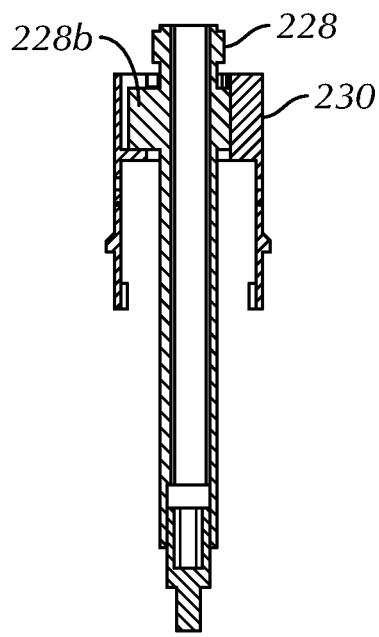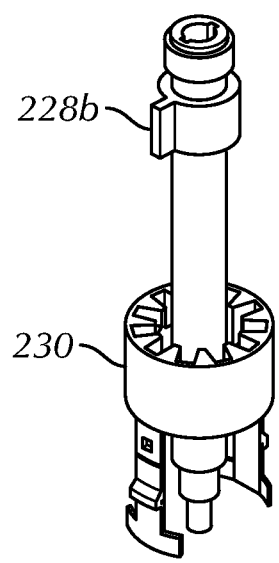
FIG. 30A
FIG. 30B
FIG. 31B
FIG. 30C
FIG. 31A

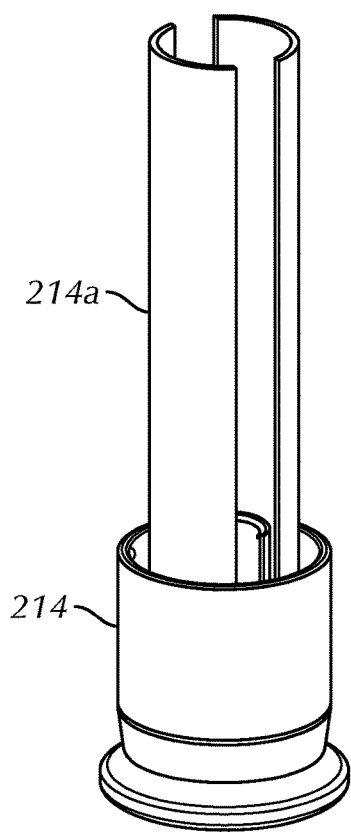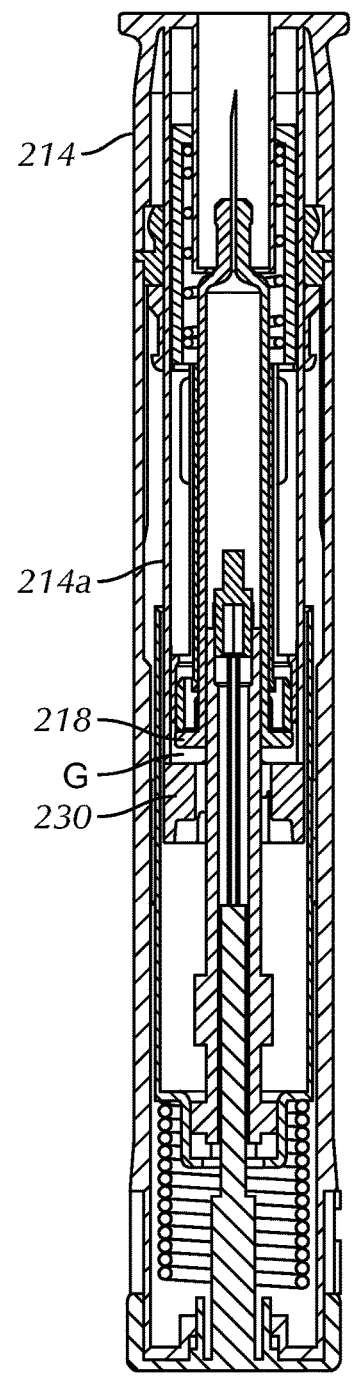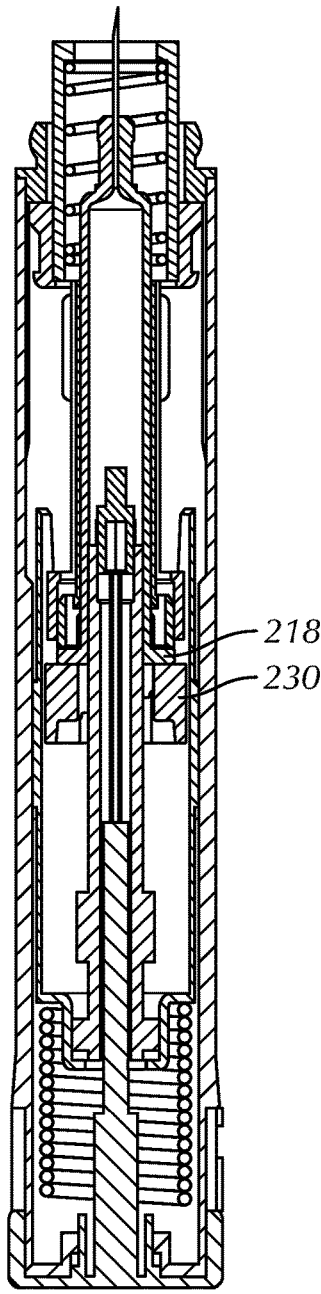
FIG. 32
FIG. 33A
FIG. 33B

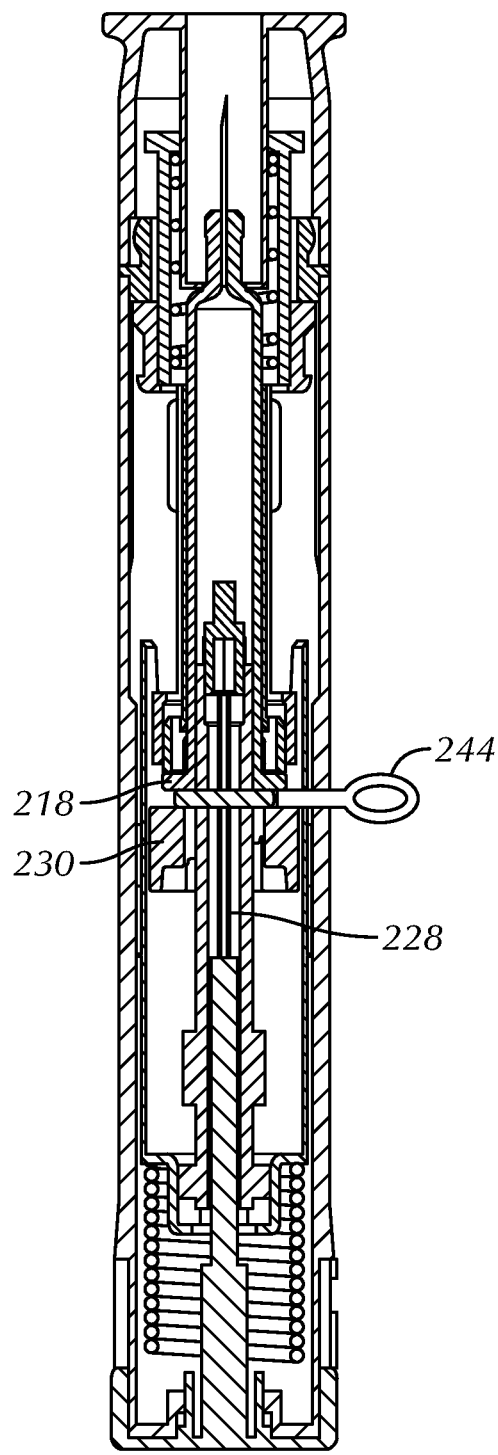
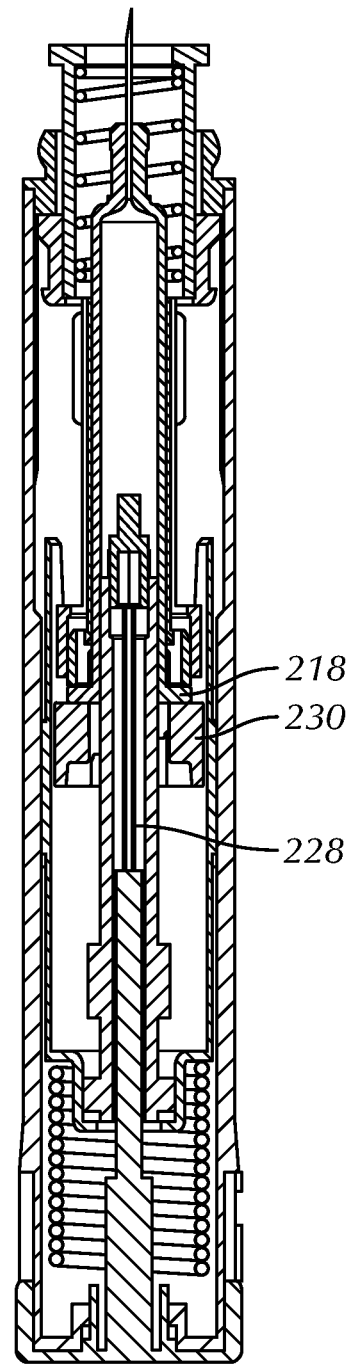
FIG. 34A
FIG. 34B

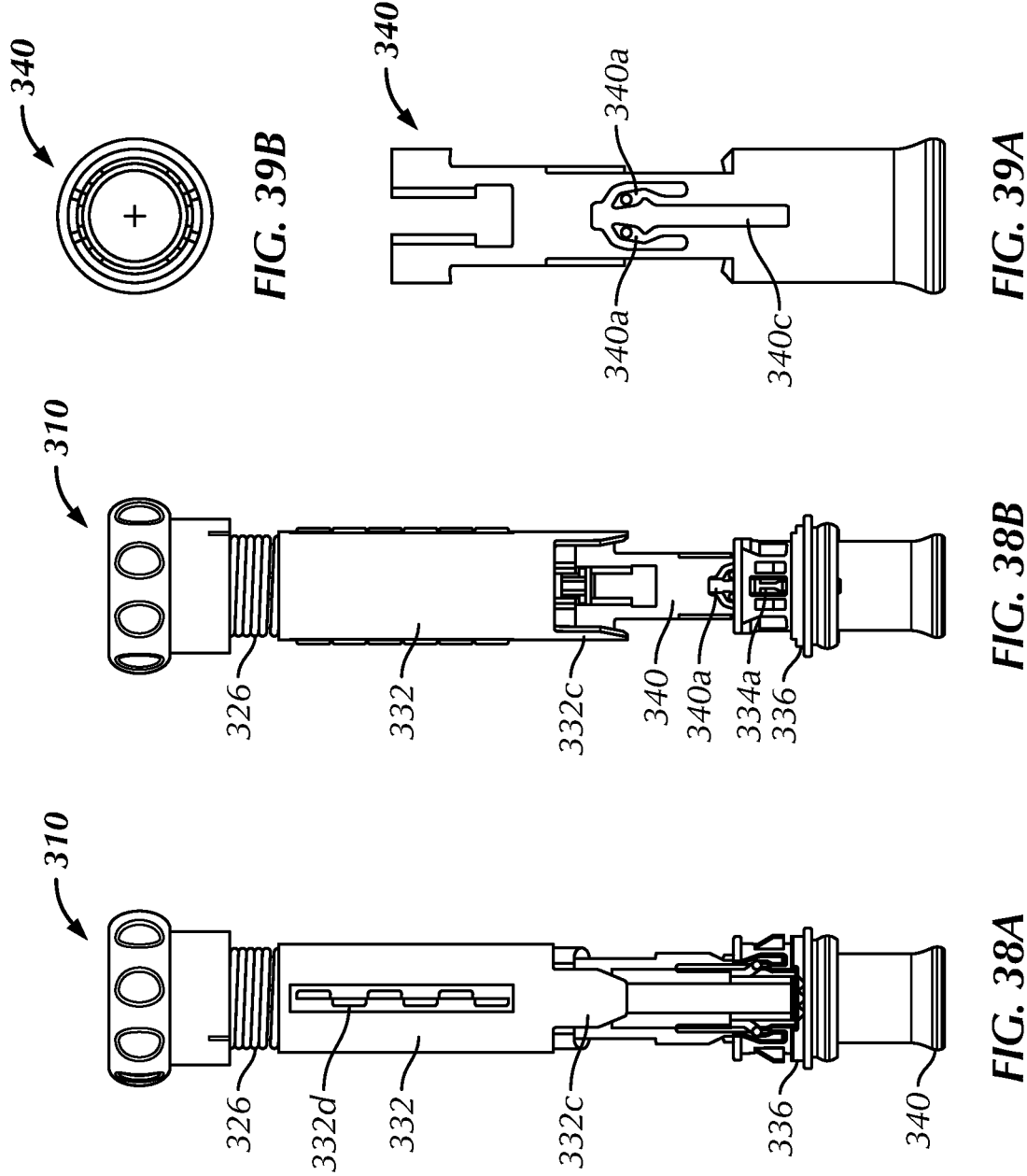

INJECTION DEVICE HAVING VARIABLE DOSING

CROSS-REFERENCE TO RELATED APPLICATIONS

This application is a U.S. National Stage of International Patent Application No. PCT/US2016/014217, filed Jan. 21, 2016, which claims the benefit of U.S. Provisional Patent Application No. 62/105,897 filed Jan. 21, 2015, U.S. Provisional Patent Application No. 62/116,836 filed Feb. 16, 2015, and U.S. Provisional Patent Application No. 62/140,023 filed Mar. 30, 2015, which are all entitled "Injection Device Having Variable Dosing" and each is incorporated by reference herein in its entirety.

FIELD OF THE INVENTION

The present invention generally relates to an injection device having variable dosing, and in some embodiments, to an auto-injection device having variable dosing.

BACKGROUND OF THE INVENTION

Injection devices for injection of medicaments into a patient are generally known. Such devices include, for example, traditional hypodermic needle syringes that contain a stock of medicament therein. Upon insertion of the needle under the patient's skin at an injection location, the medicament is forced out of the syringe and through the needle by depression of a plunger mechanism.

Self-injectors or auto-injectors like the ones disclosed in U.S. Pat. Nos. 4,553,962 and 4,378,015, and PCT Patent Application Publications WO 95/29720 and WO 97/14455 are configured to inject medicament at a rate and in a manner similar to hand-operated hypodermic syringes.

These injectors often are made for a single use, or alternatively to be refilled after each injection. Some refillable injectors can be refilled with a desired dosage to be injected. Upon injection, the entire loaded dosage is injected.

BRIEF SUMMARY OF THE INVENTION

In one embodiment there is an injection device for injecting medicament in a patient comprising: a housing configured to house a fluid reservoir having one of a plurality of volumes of medicament; an injection conduit fluidly coupled to the fluid reservoir configured to define a fluid pathway from the fluid reservoir to the patient; a firing mechanism coupled to the fluid reservoir and configured to expel the medicament from the fluid reservoir through the injection conduit; a volume setting mechanism coupled to the firing mechanism and configured to be adjusted to select the one of the plurality of volumes of medicament for the firing mechanism to expel; and a dose setting mechanism configured to be adjusted to select a fraction of the one of the plurality of volumes of medicament that is injected from the injection conduit when the firing mechanism is actuated.

In one embodiment, the volume setting mechanism includes a nut and the firing mechanism includes a ram and a biasing member, the nut being threadably coupled to the ram, the nut being releaseably retained against a force of the biasing member in an initial position by a latch. In one embodiment, the nut includes a plurality of indentations each configured to engage with a projection of the latch. In one embodiment, each of the plurality of indentations includes a ring shaped groove extending circumferentially around the nut. In a further embodiment, the injection device comprises a guard that is slideably coupled to the housing, wherein the guard is configured to release the latch from the nut. In a further embodiment, the injection device comprises a biasing member coupled to the guard and configured to bias the guard toward a distal end of the injection device, the guard configured to extend axially past the injection conduit.

In one embodiment, the guard extends further distally in a locked position than in an initial position. In one embodiment, the nut is rotatable relative to the latch. In one embodiment, the nut is configured to couple to the latch in one of a plurality of positions along an axial length of the nut, each of the plurality of positions along the axial length of the nut corresponding to one of the plurality of volumes of medicament for the firing mechanism to expel. In one embodiment, the volume setting mechanism includes a ram extension threadably coupled to the ram, the ram extension configured to extend the length of the ram to one of a plurality of positions corresponding to one of the plurality of volumes of medicament for the firing mechanism to expel. In one embodiment, the ram is rotatably fixed and axially moveable relative to the dose setting mechanism.

In one embodiment, the latch includes a latch arm releaseably retaining the nut in the initial position and a stop engaging the nut in a fired position, a distance between the latch arm and the stop being fixed. In one embodiment, the volume setting mechanism includes a retainer and a latch and the firing mechanism includes a ram and a biasing member, the latch being coupled between the biasing member and the ram, the latch being retained against a force of the biasing member in an initial position by the retainer. In a further embodiment, the injection device comprises a stop having a plurality of axially extending and radially projecting slots each extending a different axial depth, wherein the ram includes a wing extending radially from the ram and configured to engage one of the plurality of slots in a fired position.

In one embodiment, the stop and the retainer are integrally connected. In one embodiment, the dose setting mechanism is rotatably coupled to the ram to radially align the wing with one of the plurality of slots in the initial position. In one embodiment, the ram includes a prime screw threadably coupled to the end of the ram, the prime screw configured to couple the ram to a piston. In one embodiment, the ram remains in contact with the piston independent of the position of the dose setting mechanism. In one embodiment, the latch includes a plurality of axially spaced indentations each configured to engage with a projection of the retainer. In a further embodiment, the injection device comprises a guard that is slideably coupled to the housing, wherein the guard includes a sidewall configured to prevent radial motion of the retainer in the initial position and an aperture in the sidewall configured to allow radial motion of the retainer in a retracted position.

In one embodiment, the ram is rotatably fixed and axially moveable relative to the dose setting mechanism. In one embodiment, the dose setting mechanism includes a shaft extending partially into and radially keyed with an inner shaft of the ram in the initial position and a fired position. In one embodiment, the latch is axially fixed and rotatably moveable relative to the ram. In one embodiment, the firing mechanism includes a spring and the position of the spring being independent from the position of the dose setting mechanism. In one embodiment, the dose setting mechanism includes a knob rotatably coupled to the housing. In a further embodiment, the injection device comprises a guard slideably coupled to the housing and configured to extend axially past the injection conduit and lock relative to the housing after removing the injection conduit from the patient.

In one embodiment, the injection conduit comprises a needle. In a further embodiment, the injection device comprises a syringe containing the fluid reservoir, wherein the needle is fixed to the syringe. In one embodiment, the injection device is configured to prevent resetting after the firing mechanism is actuated so as to prevent a subsequent injection of the medicament by the injection device, thereby configuring the injection device as a single-use injector. In a further embodiment, the injection device comprises a safety cap coupled to a distal end of the housing, the safety cap being coupled to the firing mechanism such that decoupling the safety cap from the housing allows the firing mechanism to advance a predetermined distance relative to the fluid reservoir to prime the fluid reservoir. In one embodiment, actuating the dose setting mechanism advances the firing mechanism a predetermined distance relative to the fluid reservoir to prime the fluid reservoir. In one embodiment, the firing mechanism is configured to deliver each of the selected fraction of the one of the plurality of volumes of medicament over a generally equal amount of time as compared to one another. In one embodiment, the fraction is only greater than or equal to 0.5. In one embodiment, the selected fraction results in a residual volume remaining in the fluid reservoir after delivery of 0.18 ml or less.

In another embodiment, there is an injection device for injecting medicament in a patient comprising: a firing mechanism having an actuator and configured to be selectively preset during assembly to one of a plurality of positions based on a maximum volume of medicament to be delivered to the patient; and a dose setting mechanism configured to be selectably adjusted upon use, independent of the preset of the firing mechanism, to select a fraction of the maximum volume of medicament to be delivered to the patient.

In another embodiment there is an injection device for injecting medicament in a patient comprising: a housing configured to house a fluid container having a piston and a fluid reservoir having one of a plurality of volumes of medicament, the fluid container including an injection conduit fluidly coupled to the fluid reservoir defining a fluid pathway from the fluid reservoir to the patient; a ram coupled to the piston and configured to expel the medicament from the fluid reservoir through the injection conduit; a spring biasing the ram toward the fluid container in an initial position; a nut threadably coupled to the ram, the nut having a plurality of ring shaped grooves or projections; a latch fixed relative to the housing and engaging a predetermined one of the plurality of ring shaped grooves or projections to retain the ram in one of a plurality of axial positions against a force of the spring in the initial position, the nut being rotatable relative to the latch in the initial position; and a dose setting knob rotatably coupled to the housing and rotatably fixed and axially moveable relative to the ram in the initial position.

In another embodiment there is an injection device for injecting medicament in a patient comprising: a housing configured to house a fluid container having a piston and a fluid reservoir having one of a plurality of volumes of medicament, the fluid container including an injection conduit fluidly coupled to the fluid reservoir defining a fluid pathway from the fluid reservoir to the patient; a ram coupled to the piston and configured to expel the medicament from the fluid reservoir through the injection conduit, the ram having a radially extending wing; a latch axially fixed and rotatably moveable relative to the ram, the ram having a plurality of radial features; a spring biasing the latch toward the fluid container in an initial position; a retainer fixed relative to the housing and engaging a predetermined one of the plurality of radial features to retain the ram in one of a plurality of axial positions against a force of the spring in the initial position; a stop having a plurality of axially extending and radially projecting slots each extending a different axial depth, the ram being rotatable to align the wing with one of the plurality of slots in the initial position and the wing configured to engage the one of the plurality of slots in a fired position; and a dose setting knob rotatably coupled to the housing, the ram being rotatably fixed and axially moveable relative to the dose setting knob.

In another embodiment there is a method for assembling an injection device comprising: inserting a fluid container having a fluid reservoir including one of a plurality of volumes of medicament into a housing, the fluid container including an injection conduit fluidly coupled to the fluid reservoir defining a fluid pathway from the fluid reservoir to the patient; setting a volume setting mechanism based on a size of the one of the plurality of volumes of the medicament; coupling the volume setting mechanism to a firing mechanism; and coupling the firing mechanism to the fluid reservoir, the firing mechanism configured to expel the medicament from the fluid reservoir through the injection conduit, the firing mechanism being coupled to a dose setting mechanism configured to select all or a fraction of the one of the plurality of volumes of medicament that is injected from the injection conduit when the firing mechanism is actuated.

In another embodiment there is an injection device for injecting medicament in a patient comprising: a housing configured to house a fluid reservoir; an injection conduit fluidly coupled to the fluid reservoir defining a fluid pathway from the fluid reservoir to the patient; a firing mechanism coupled to the fluid reservoir and configured to expel the medicament from the fluid reservoir through the injection conduit; and a safety cap coupled to a distal end of the housing, the safety cap being coupled to the firing mechanism such that decoupling the safety cap from the housing allows the firing mechanism to advance a predetermined distance relative to the fluid reservoir to prime the fluid reservoir.

BRIEF DESCRIPTION OF THE SEVERAL VIEWS OF THE DRAWINGS

The following detailed description of embodiments of the injection device having variable dosing will be better understood when read in conjunction with the appended drawings of exemplary embodiments. It should be understood, however, that the invention is not limited to the precise arrangements and instrumentalities shown.

In the drawings:

FIG. 3A is a first side view of the injection device of FIG. 1;

FIG. 3B is a cross sectional side view of the injection device shown in FIG. 3A taken along a plane indicated by line A-A;

FIG. 3C is a second side view of the injection device of FIG. 1 turned 90 degrees from the view shown in FIG. 3A;

FIG. 3D is a cross sectional side view of the injection device shown in FIG. 3C taken along a plane indicated by line B-B;

FIG. 3E is a cross sectional top view of the injection device shown in FIG. 3C taken along a plane indicated by line 3E-3E;

FIG. 4A is a second side view of the injection device of FIG. 1;

FIG. 4B is a cross sectional side view of the injection device shown in FIG. 4A taken along a plane indicated by line B-B;

FIG. 4C is an enlarged cross sectional side view of a portion of the injection device shown in FIG. 4B within the circled area;

FIG. 4D is an enlarged cross sectional side view of a portion of the injection device shown in FIG. 4C within the circled area;

FIG. 5D is a second side view of the injection device of FIG. 1 shown in the primed position;

FIG. 5E is a cross sectional side view of the injection device shown in FIG. 5D taken along a plane indicated by line C-C;

FIG. 5F is a top view of the injection device shown in FIG. 5D;

FIG. 6A is a side view of the injection device of FIG. 1 shown in the initial position;

FIG. 6B is a cross sectional side view of the injection device shown in FIG. 6A taken along a plane indicated by line I-I;

FIG. 7A is a side view of the injection device of FIG. 1 shown in the minimum dose position;

FIG. 7B is a cross sectional side view of the injection device shown in FIG. 7A taken along a plane indicated by line A-A;

FIG. 8A is a side view of the injection device of FIG. 1 shown in the insertion position;

FIG. 8B is a cross sectional side view of the injection device shown in FIG. 8A taken along a plane indicated by line J-J;

FIG. 9A is a side view of the injection device of FIG. 1 shown in the released position;

FIG. 9B is a cross sectional side view of the injection device shown in FIG. 9A taken along a plane indicated by line K-K;

FIG. 10A is a side view of the injection device of FIG. 1 shown in the fired position;

FIG. 10B is a cross sectional side view of the injection device shown in FIG. 10A taken along a plane indicated by line L-L;

FIG. 12A is a side view of the injection device of FIG. 1 shown in the locked out position;

FIG. 12B is a cross sectional side view of the injection device shown in FIG. 12A taken along a plane indicated by line N-N;

FIGS. 16A-16C are views of the injection device of FIG. 1 in the fired position with the housing removed;

FIGS. 18A-18D are various views of a ram of the injection device of FIG. 1;

FIG. 23 includes various views of the ram and the ram and dose knob assembly of the injection device of FIG. 19A;

FIGS. 26A-26D are various side and perspective views of the injection device of FIG. 19A with the housing and other components removed in the triggered position;

FIGS. 27A-27D are various side and perspective views of the injection device of FIG. 19A with the housing and other components removed in the locked out position;

FIGS. 28A-28C are various views of the ram and slot stop of the injection device of FIG. 19A shown in the minimum dose setting before the dose is delivered;

FIG. 29 is a perspective view of the ram and slot stop of FIGS. 28-28C shown after the dose is delivered;

FIGS. 30A-30C are various views of the ram and slot stop of the injection device of FIG. 19A shown in the maximum dose setting before the dose is delivered;

FIGS. 31A-31B are side and side cross-sectional views respectively of the ram and slot stop of FIGS. 30A-30C shown after the dose is delivered;

FIG. 32 is a perspective view of a safety cap having a spacer for use with the injection device of FIG. 19A;

FIGS. 33A-33D are cross sectional side views of the injection device of FIG. 19A having the safety cap shown in FIG. 32;

FIGS. 34A and 34B are cross sectional side views of on the injection device of FIG. 19A having a priming release pin;

FIGS. 38A and 38B are side views of a lock-out system for an injection device in accordance with an exemplary embodiment of the present invention with the outer housing removed and shown in an initial position;

FIGS. 39A and 39B are side views a guard of the injection device of FIGS. 38A and 38B;

DETAILED DESCRIPTION OF THE INVENTION

Figure 1:
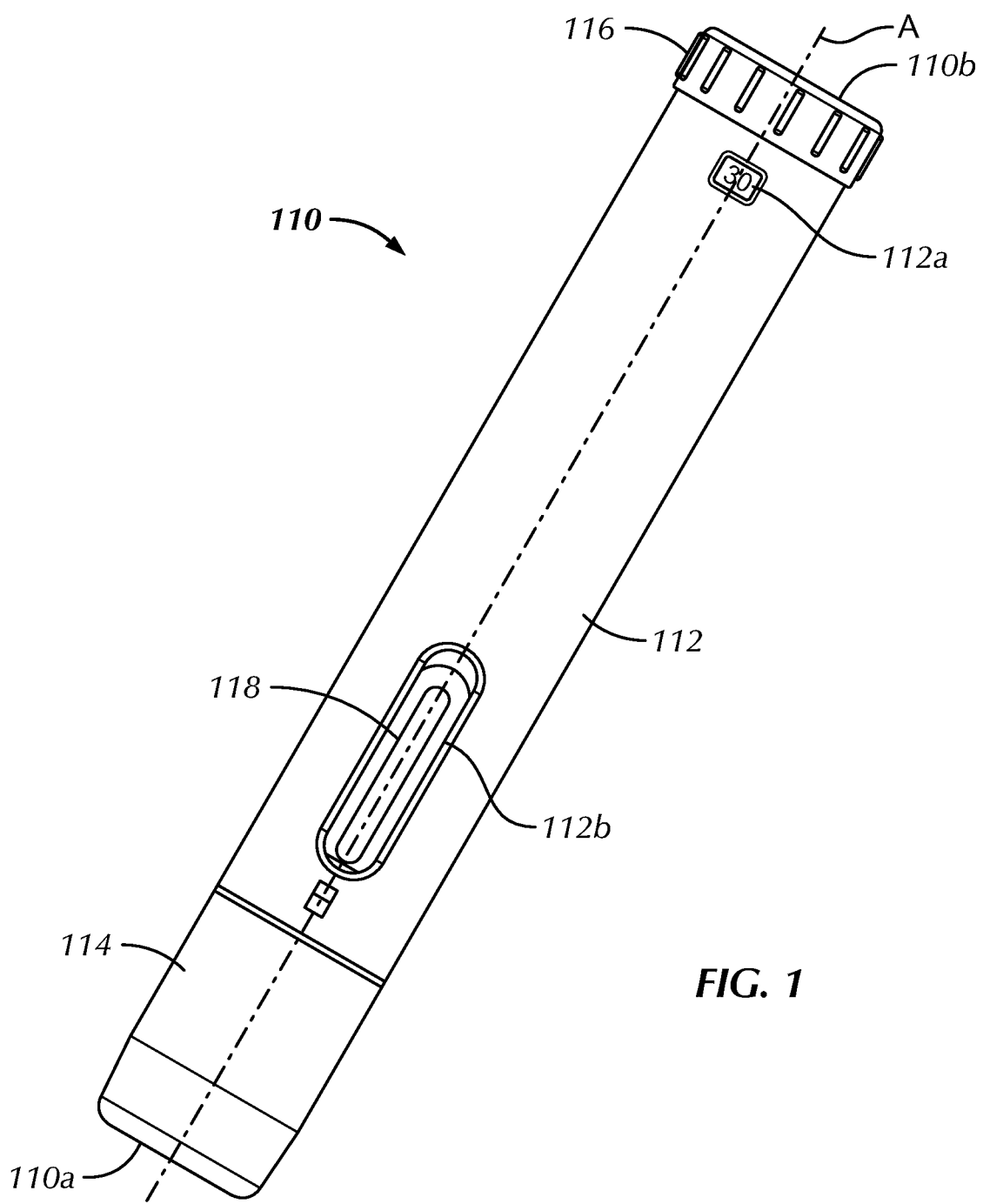
FIG. 1 is a side view of an injection device in accordance with an exemplary embodiment of the present invention.

Referring to the drawings in detail, wherein like reference numerals indicate like elements throughout, there is shown in FIGS. 1-18D an injection device, generally designated 110, a first exemplary embodiment of the present invention. Various embodiments of the injection device 110 are described in further detail below in reference to the exemplary embodiment shown in the figures.

The injection device 110 is configured to deliver a selected amount of one of a plurality of predetermined volumes of medicament to a patient. The injection device 110 is assembled using one of a plurality of fluid reservoirs and the dose that is ultimately delivered to the patient is equal to or less than the full amount contained in the injection device 110. This allows for the injection device 110 to accept fluid cartridges, prefilled syringes or similar containers being filled to different volumes and/or multiples sizes of fluid containers and then allows for the user to select how much of the fluid in the fluid container to deliver. Such flexibility allows for one device to be adapted for multiple medicament volumes and ultimately reduces the amount of wasted medicament.

For example, a typical injection device may have a volume of 1.0 ml to encompass the range of potential dosages needed. A patient who is provided a 1.0 ml device but only needs a dosage of 0.5 ml, would leave a residual volume of 0.5 ml in the discarded device. Instead, the patient, requiring a dosage of 0.5 ml, can be provided a 1.0 ml injection device 110 containing 0.6 ml of fluid, resulting in a residual volume of only 0.1 ml in the discarded device. By allowing adjustment of the volume, the manufacturer can easily set the injection device 110 to one of a plurality of volumes to divide up the range of dosages selectable by a patient and reduce the amount of residual fluid left in the discarded device.

The injection device 110 includes an actuator for driving fluid from the injection device 110 into the patient. In some embodiments, the actuator is automatically actuated as a result of positioning the injection device 110 relative to the skin surface, also referred to as an auto-injection device. The injection device 110 may include a needle. In other embodiments, the injection device does not include a needle and the injection port of the fluid chamber preferably defines a fluid pathway in fluid communication with the fluid chamber for injecting medicament as a jet from the chamber through the port to the injection location. An example of a suitable needle-free jet nozzle arrangement is disclosed in U.S. Pat. No. 6,309,371, which is incorporated by reference in its entirety.

As disclosed in further detail below, in some embodiments, the injection device 110 includes a firing mechanism having an actuator, a volume setting mechanism configured to be selectively preset during assembly to one of a plurality of positions based on a maximum volume of medicament to be delivered to the patient (e.g., one of a 0.4 ml, 0.6 ml, 0.8 ml or 1.0 ml prefilled syringe) and a dose setting mechanism configured to be selectably adjusted upon use, independent of the preset of the volume setting mechanism, to select a fraction of the maximum volume of medicament to be delivered to the patient (e.g., a 0.2 ml to 0.4 ml dose for a 0.4 ml syringe).

Referring to FIG. 1, the injection device 110 may include a housing 112. The housing 112 extends along a longitudinal axis A and is configured to be held in one hand of a patient or caregiver to deliver the dose of medicament to the patient. In one embodiment, the housing 112 is cylindrical. In other embodiments, the cross sectional shape of the housing 112 is elliptical, triangular, square or any other desired shape. The housing 112 may include one or more windows 112a, 112b for viewing components of the injection device 110 contained within the housing 112. The windows 112a, 112b may be covered with a transparent material. Windows 112a, 112b may allow the viewing of the fluid reservoir 118 within the housing 112. The window 112a, 112b may also allow viewing of the preset volume that has been chosen. In another embodiment, the window 112a, 112b allows viewing that the injection device 110 is ready for use. In another embodiment, the window 112a, 112b allows viewing that the injection is complete. Other uses of a window to allow viewing internal aspects of the injection device are anticipated. In an embodiment, the window 112a, 112b allows viewing of injection device internal components that assist in administering an injection. In one embodiment, the housing 112 is comprised partially or entirely of a transparent material.

Referring to FIG. 3B, the housing 112 is configured to house a fluid reservoir 118 having one of a plurality of volumes of medicament. The desired volume of the fluid reservoir 118 is selected before assembling the injection device 110. In one embodiment, the desired volume of the fluid reservoir 118 is based on the desired maximum dose that the patient will be able to inject. In one embodiment, the injection device 110 is configured to receive one sized container or syringe having a fluid reservoir 118 configured to accommodate a plurality (e.g., four) different maximum volumes for injection. In other embodiments, the injection device 110 is configured to receive a fluid reservoir configured to accommodate two, three, or five or more different maximum volumes for injection. In other embodiments, the injection device 110 is configured to receive one of four differently sized containers having a fluid reservoir 118. In other embodiments, the injection device 110 is configured to receive one of two, three, five or more differently sized containers having fluid reservoirs 118. In one embodiment, the fluid reservoir 118 contains one of 0.4 ml, 0.6 ml, 0.8 ml, or 1.0 ml of medicament. In other embodiments, the fluid reservoir 118 contains other amounts of medicament such as one or more of the following amounts: 0.04 ml, 0.05 ml, 0.06 ml, 0.07 ml, 0.08 ml, 0.09 ml, 0.1 ml, 0.2 ml, 0.3 ml, 0.4 ml, 0.5 ml, 0.6 ml, 0.7 ml, 0.8 ml 0.9 ml, 1.0 ml, 1.1 ml, 1.2 ml, 1.3 ml, 1.4 ml, 1.5 ml, 1.6 ml, 1.7 ml, 1.8 ml, 1.9 ml, 2.0 ml, greater than 2.0 ml, less than 0.010 ml and any amount between these numbers. In one embodiment, the fluid reservoir 118 includes a prefilled syringe having a piston 120 forming a sliding seal at a proximal end. An injection conduit 122 is fluidly coupled to the fluid reservoir defining a fluid pathway from the fluid reservoir to the patient. In one embodiment, the injection conduit 122 is a needle. The needle 122 may be staked to the prefilled syringe.

Referring to FIG. 3B, the needle 122 may be covered by a needle cap 124 in the stowed or initial position. The needle cap 124 may include an elastomeric material for sealing and protecting the needle 122 in the initial position. Referring to FIG. 1, the injection device 110 may further or alternatively include a safety cap 114 that is releaseably coupled to a distal end 110a of the injection device 110. The safety cap 114 covers the injection conduit 118 in the initial position to prevent contamination and accidental needle sticks or actuation of the actuator. The safety cap 114 may be coupled to the needle cap 124 such that removing the safety cap 114 from the housing 112 also strips the needle cap 124 from the needle 122 and exposes the needle 122.

The injection device 110 may include a firing mechanism coupled to the fluid reservoir 118 and configured to expel the medicament from the fluid reservoir 118 through the injection conduit 122 (see FIG. 3B). The firing mechanism may include an actuator such as a biasing member 126. In one embodiment, the biasing member 126 includes a compression spring. In another embodiment, the actuator is pneumatically driven. The biasing member 126 may be operatively associated with a ram 128 extending along the longitudinal axis A. The ram 128 may include a keyed proximal end 128a and one or more male or female threads 128b. The ram 128 may include a pair of diametrically opposed threadless portions 128e extending along the length of the ram 128 (see FIGS. 18A-18D). In one embodiment the threadless portion 128e may serve as a keyed feature to transfer torque or provide location to an adjacent component. The threadless portions 128e may be recessed relative to the threads 128b to allow for a flash or other manufacturing artifact to exist on the threadless portion 128e without interfering with the use of the threads 128b. The ram 128 may be coupled to the fluid reservoir 118 such that the biasing member 126 urges the ram 128 to compress the fluid reservoir 118 and deliver the medicament to the patient through the injection conduit 122. In one embodiment, the ram 128 is coupled to the piston 120. The ram 128 may include a projection 128c extending distally for supporting the engagement between the ram 128 and the piston 120 (see FIG. 3B).

Referring to FIGS. 4A-4D, the volume setting mechanism may be set to provide the one of the plurality of volumes of medicament. The volume setting mechanism may include a nut 130 that is releaseably retained in the axial direction against a force of the biasing member 126 in an initial position by a latch 132 (see FIG. 3B). The latch 132 may include a projection 132a that engages a corresponding indent 130a in the nut 130 to prevent axial movement of the nut 130 in the initial position.

The nut 130 may include a plurality of indentations 130a each configured to engage with the projection 132a of the latch. Each of the plurality of indentations may be axially spaced from one another. Each of the plurality of indentations 130a of the nut 130 may include a ring shaped groove extending circumferentially around the nut 130. The nut 130 may be rotatable relative to the latch 132. In some embodiments, providing ring shaped grooves and allowing the nut 130 to rotate relative to the latch 132 allows for the dose setting mechanism 116 to rotate the ram 128 relative to the nut 130 and therefore axially move the ram 128 as discussed further below. During assembly of the injection device 110, the nut 130 is configured to couple to the latch 132 in one of a plurality of positions along an axial length of the nut 130, each of the plurality of positions along the axial length of the nut 130 corresponding to one of the plurality of volumes of medicament for the firing mechanism to expel.

The nut 130 may be configured to engage a stop fixed relative to the fluid delivery device 110 at the end of the delivery stroke as discussed below. As a result, the distance the ram 128 extends distally from the nut 130, in some embodiments, is set to correspond to the volume of the fluid reservoir 118 (e.g., the axial distance between the piston 120 and the nut 130). For example, the position of the latch 132 relative to the nut 130 in the position illustrated in FIGS. 4B-4D corresponds to a volume of a 0.6 ml fluid reservoir 118. If a 0.4 ml fluid reservoir 118 is used, then the nut 130 may be rotated distally down the ram 128 until the next higher indent 130a of the nut 130 aligns with the projection 132a of the latch 132. If a 0.8 ml fluid reservoir 118 is used, then the nut 130 may be rotated proximally up the ram 128 until the next lower indent 130a of the nut 130 aligns with the projection 132a of the latch 132.

The latch 132 may include a sleeve 132d surrounding the nut 130 and axially fixed relative to the fluid reservoir 118. The latch 132 may include a pivot arm 132c that is pivotably connected to the sleeve 132d and configured to radially move the projection 132a out of the axial path of the nut 130 in the firing or released position (see FIG. 9B). In one embodiment, the pivot arm 132c is prevented from pivoting in an initial position by a radial stop 140e (see FIG. 2). The latch 132 may include a slanted surface 132b that engages with a corresponding slanted surface 140d in the released position (see also FIG. 17). Once the latch 132 is disengaged from the nut 130, the nut 130 and the threadably engaged ram 128 are released axially and fired distally by the biasing member 126. In other embodiments, the latch 132 and nut 130 have the reverse mating relationship described above such that the latch 132 includes a feature that engages with one of a plurality of projections from the nut 130.

Referring to FIG. 4B, the direct force of the biasing member 126 upon triggering may be borne by the latch 132. In an embodiment, the latch 132 includes a stop 132e to attenuate the shock resulting from the stoppage of the firing mechanism at the termination of the injection stroke. The stop 132e may be a radially inwardly extending flange. At the end of delivery stroke (see FIGS. 9B and 10B) the nut 130 may engage the stop 132e. In one embodiment, the stop 132e includes a resilient feature. In one embodiment, the resilient feature of the stop 132e includes a spring. In another embodiment, the resilient feature of the stop 132e includes an elastomeric washer.

In one embodiment, setting the volume by coupling the nut 130 to the latch 132 at one of a plurality of locations results in an adjustment of the spring force by biasing member 126. By moving the nut 130 axially relative to the latch 132 to set the volume, the biasing member 126 may be more compressed for the larger volumes and less compressed for the smaller volumes. The rate of delivery for a larger dose may therefore be higher than the rate of delivery for a smaller dose resulting in a generally equal amount of time to deliver each dose. In some embodiments, the delivery time is not equal for each dose but closer to being equal than if the rate of delivery was instead constant. Referring to Table 1 below for example, a dose of 1.0 ml may be delivered in approximately 7-10 seconds and a dose of 0.6 ml may be delivered in approximately 6-9 seconds. Such a configuration, where the variability between delivery times for each dose is minimized, may be desirable for compliance. For example, a patient who starts a treatment at a lower volume may be accustomed to waiting a certain amount of time to deliver a dose and be inclined to wait the same amount of time even if the treatment is adjusted to a higher volume. An amount of spring decay may be selected such that any differences in injection time between volumes do not result in improper use of the device.

TABLE 1

Range of delivery times

| Delivered Vol. (ml) | Injection time range (sec) |
|---|---|
| 1.0 | 7-10 |
| 0.8 | 7-9 |
| 0.6 | 6-8 |
| 0.4 | 5-8 |
| 0.2 | 4-7 |

It may be desirable to provide a spring with a spring force decay curve where such that the difference in injection time between the volumes is such that the user does not perceive a significant difference.

In another embodiment, rather than or in addition to the nut 130 having a plurality of predetermined positions, the volume setting mechanism includes a ram extension (not shown) threadably coupled to the ram 128. The ram extension may be configured to extend the length of the ram 128 to a plurality of axial positions during assembly corresponding to one of the plurality of volumes of medicament for the firing mechanism to expel.

Figure 2:
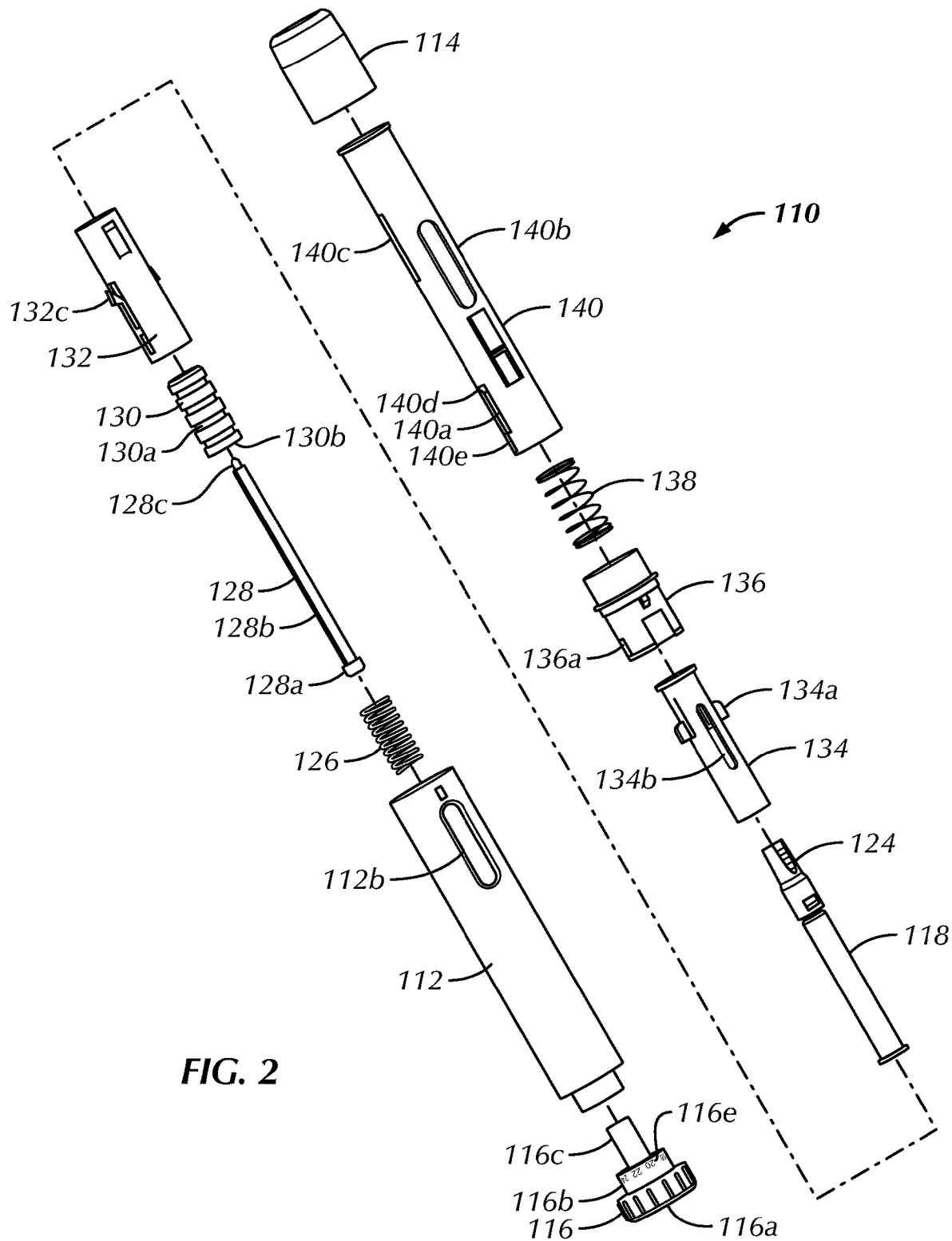
FIG. 2 is an exploded perspective view of the injection device of FIG. 1.
Figure 5A:
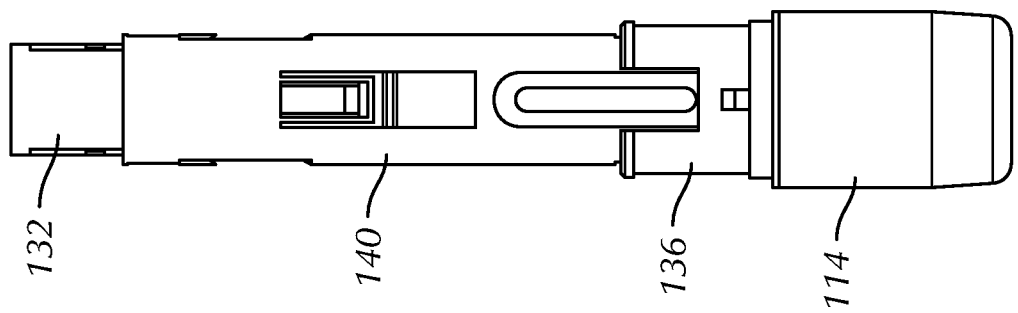
FIG. 5A is a first side view of the injection device of FIG. 1 shown with the housing removed and in the un-primed position.
Figure 5B:
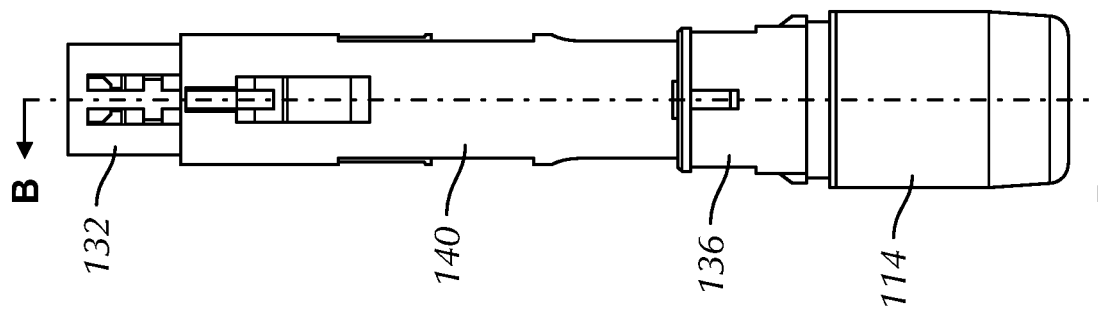
FIG. 5B is a second side view of the injection device of FIG. 1 shown with the housing removed, turned 90 degrees from the first side view shown in FIG. 5A and shown in the un-primed position.
Figure 5C:
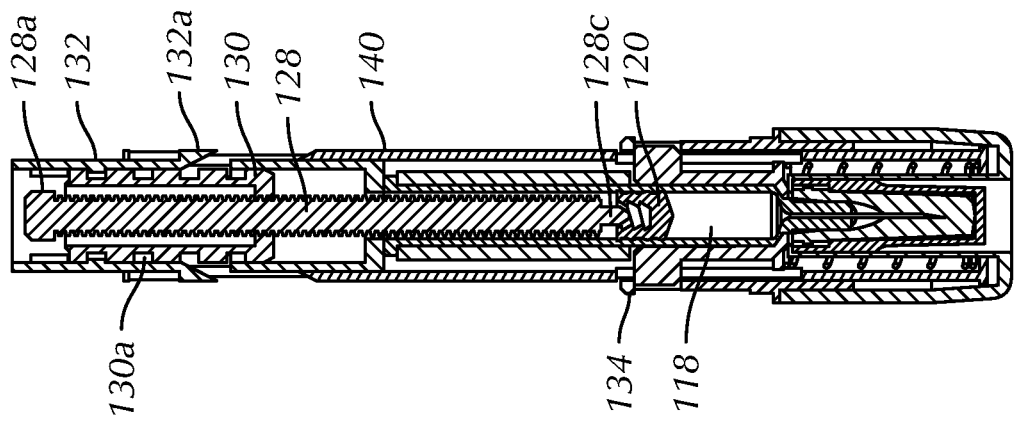
FIG. 5C is a cross sectional side view of the injection device shown in FIG. 5B taken along a plane indicated by line B-B.
Figures 11A, 11B:
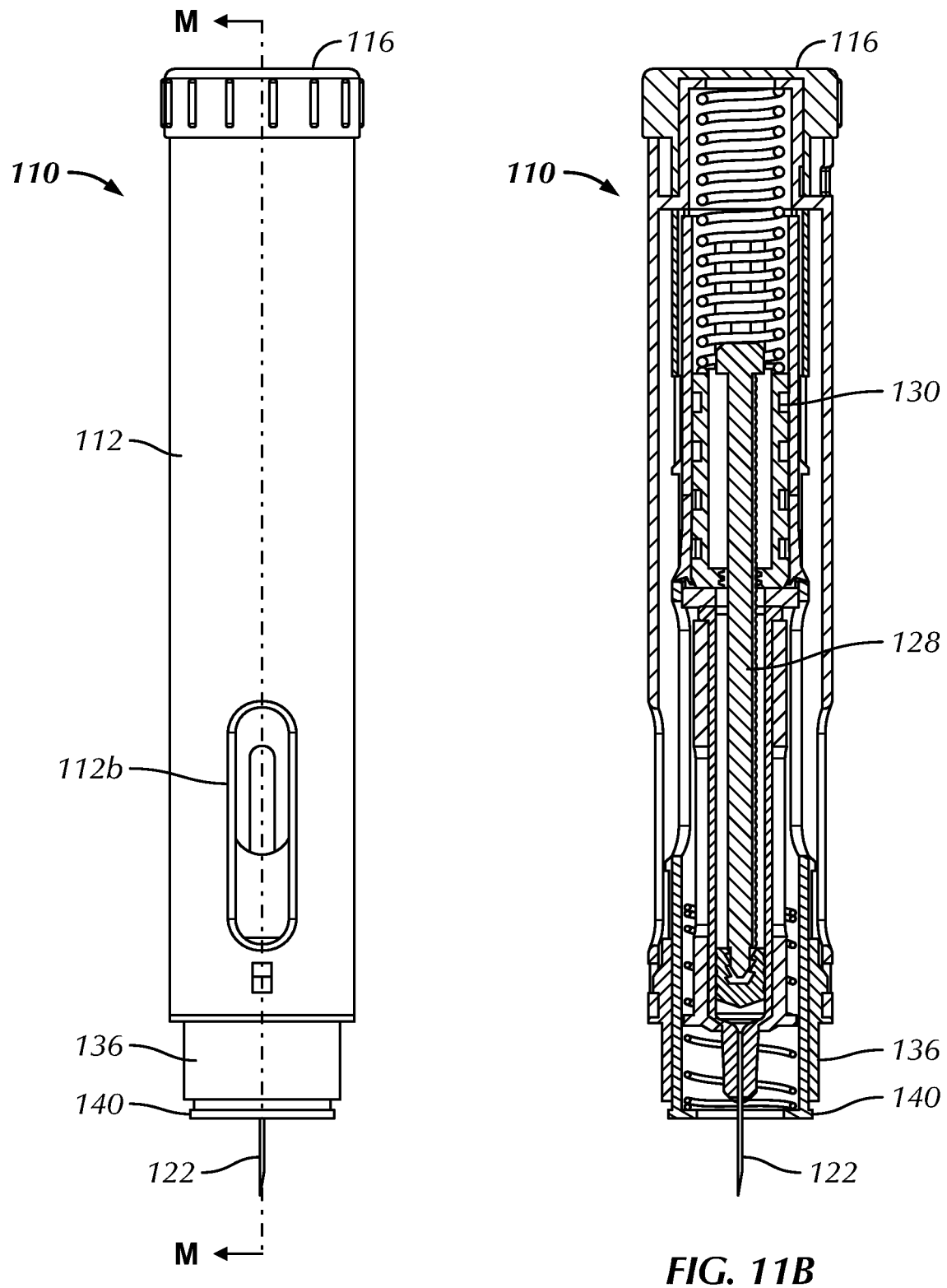
FIG. 11A is a side view of the injection device of FIG. 1 turned 90 degrees from the side view of FIG. 10A.
FIG. 11B is a cross sectional side view of the injection device shown in FIG. 11A taken along a plane indicated by line M-M.
Figure 13A:
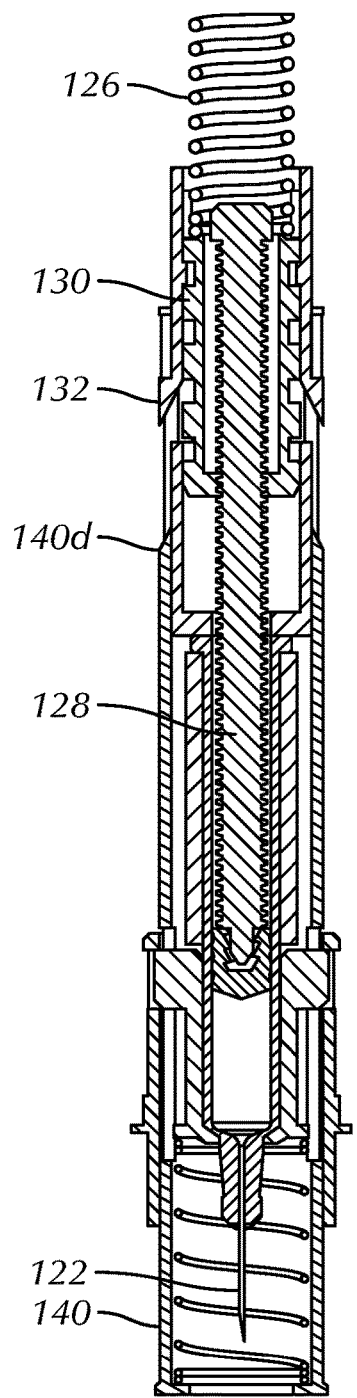
FIGS. 13A-13C are views of the injection device of FIG. 1 shown in the initial position with the housing removed.
Figure 13B:
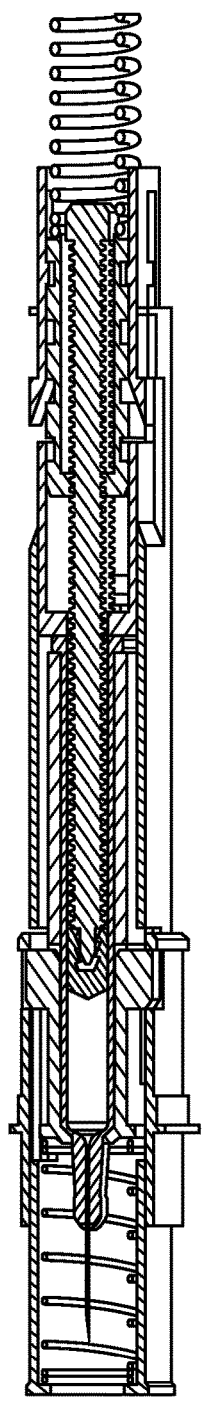
Figure 13C:
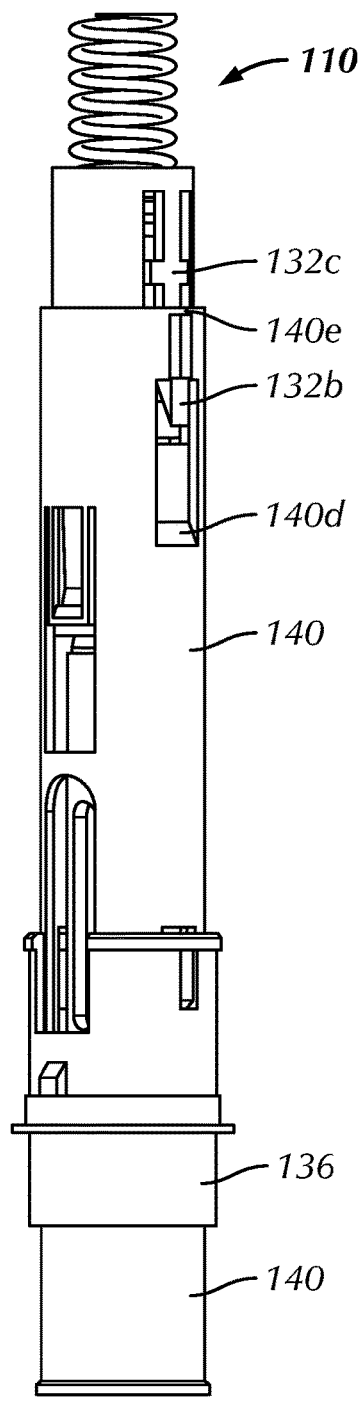
Figure 14A:
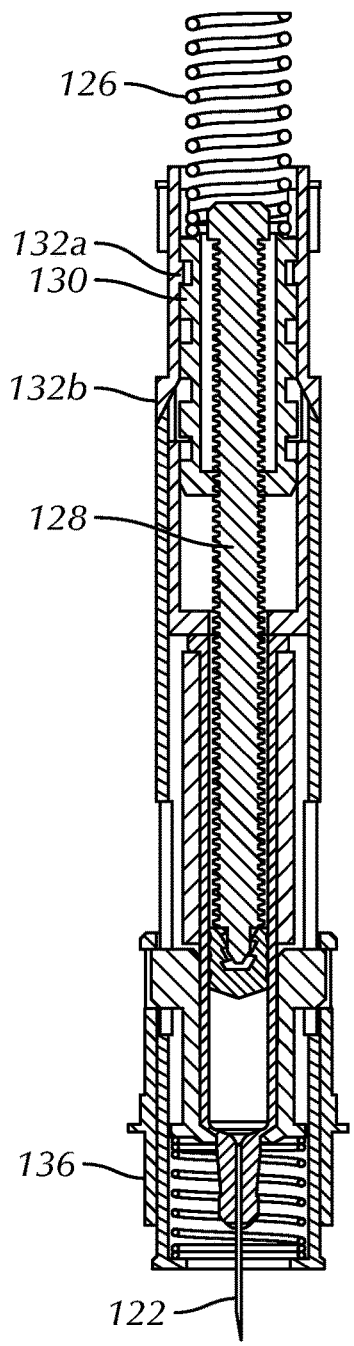
FIGS. 14A-14C are views of the injection device of FIG. 1 shown in the insertion position with the housing removed.
Figure 14B:
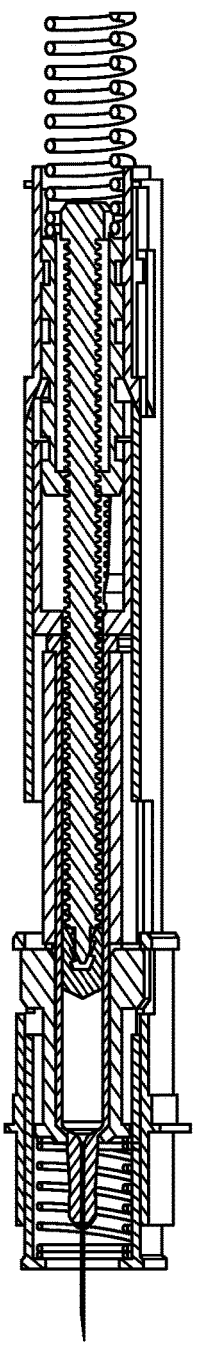
Figure 14C:
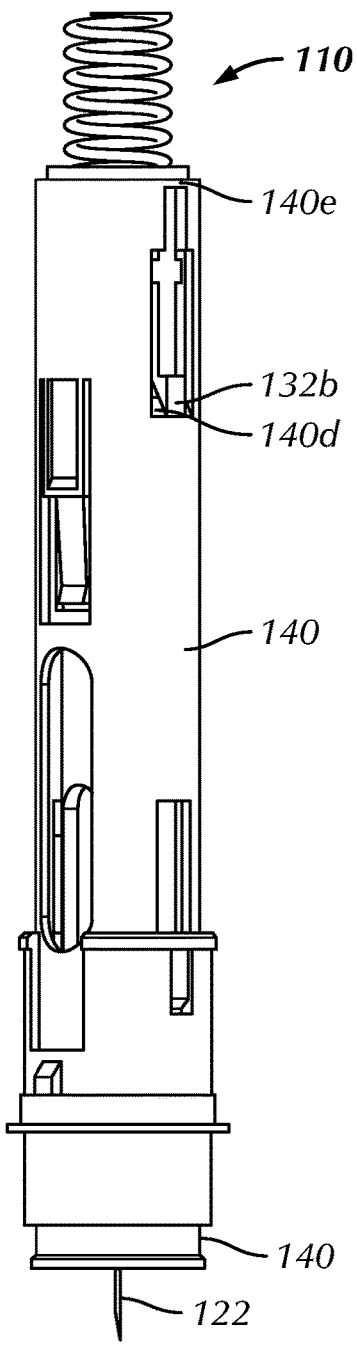
Figure 15A:
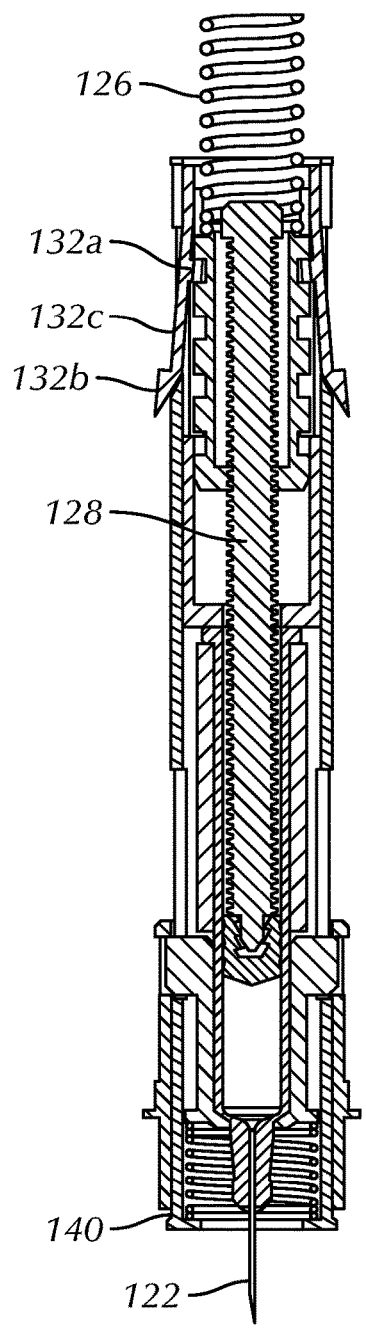
FIGS. 15A-15C are views of the injection device of FIG. 1 shown in the released position with the housing removed.
Figure 15B:
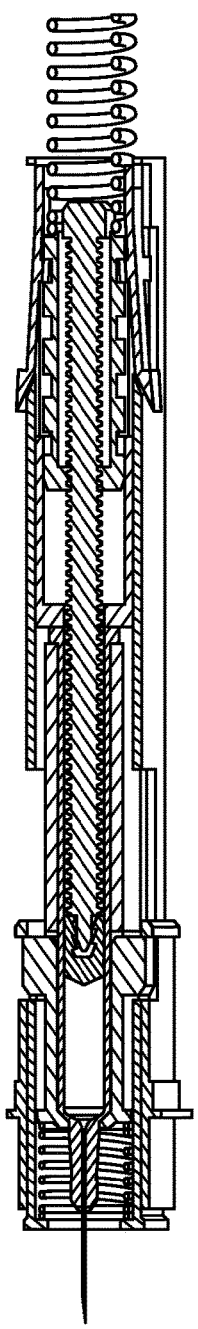
Figure 15C:
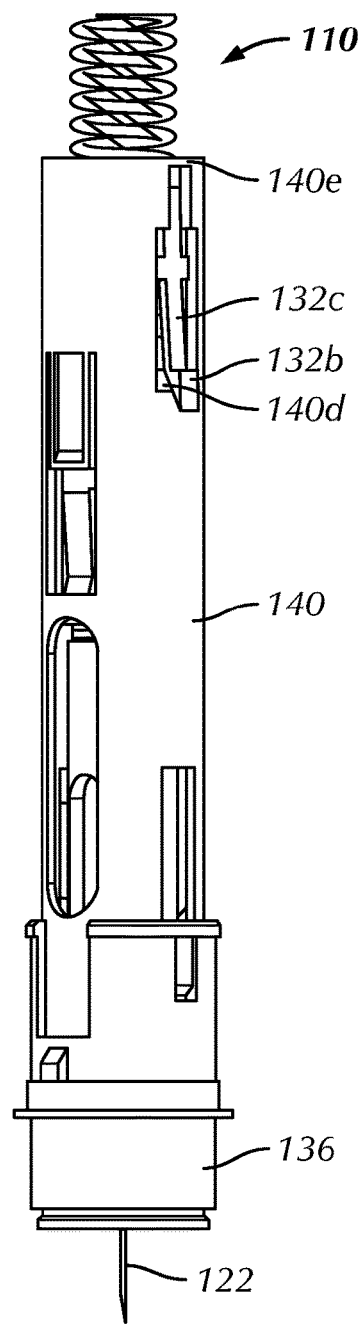
Figure 17:
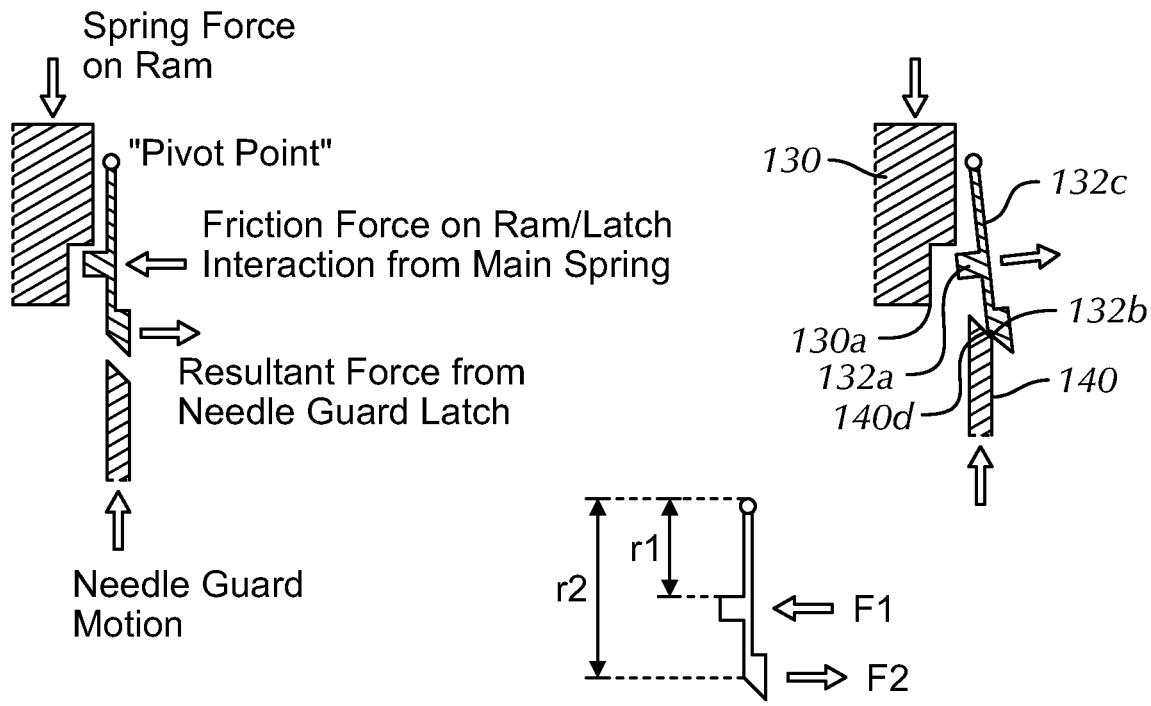
FIG. 17 is an illustration of the mechanical advantage of the latch of the injection device of FIG. 1.

Referring to FIG. 2, the injection device 110 may include a dose setting mechanism 116 configured to select a fraction of the one of the plurality of volumes of medicament that is injected from the injection conduit 122 when the firing mechanism is actuated. The dose setting mechanism 116 may include a knob rotatably coupled to the housing. In one embodiment, the dose setting mechanism 116 caps the proximal end of the housing 112. The dose setting mechanism 116 may include a grip portion 116a for grasping by the patient. The grip portion 116a may include one or more features such as axially extending ribs 116a for increasing the frictional force between the dose setting mechanism 116 and a user's hand during use. The dose setting mechanism 116 may include a dosage level portion 116b having a plurality of dosage indicia 116e. The dose setting mechanism 116 may include a shaft 116c for coupling to the ram 128.

Referring to FIGS. 3A-3D, the dose setting mechanism 116 is rotatably moveable relative to the housing 112. In one embodiment, the dose setting mechanism 116 is fixed axially relative to the housing 112. The dose setting mechanism 116 may be rotatably fixed and axially moveable relative to the ram 128. The proximal end 128a of the ram 128 may have a keyed shape that corresponds to the shape of the inside surface 116d of shaft 116c of the dose setting mechanism 116 such that rotating the dose setting mechanism 116 rotates the ram 128, and due to the threaded connection between the ram 128 and the axially retained nut 130, moves the ram 128 distally and proximally depending on the direction of rotation. When the dose setting mechanism 116 is rotated, indicia 116e corresponding to the position of the ram 128 may align with the window 112a in the housing 112 to display the selected dosage to the patient. In one embodiment, rotating the dose setting mechanism 116 to move the ram 128 does not impact the position and force on the biasing member 126. In some embodiments, the dose setting mechanism 116 includes a resistance and/or an audible click between selected dosages.

Referring to FIG. 6B, the biasing member 126 such as a spring may be uniform and configured to not buckle. In one embodiment, there is no direct spring load on the ram 128 from the biasing member 126 in the initial position. This allows for the ram 128 to be axially positioned during dose setting without impacting the spring force allowing for the spring force to be the same for each different volume of medicament.

Referring to FIG. 2, the injection device 110 may configured to prevent resetting after the firing mechanism is actuated so as to prevent a subsequent injection of the medicament by the injector, thereby configuring the injection device 110 as a single-use injector. In one embodiment, the injection device 110 includes a guard 140 that is slideably coupled to the housing 112. The injection device 110 may include a biasing member 138 coupled to the guard and configured to bias the guard 140 toward a distal end 110a of the injection device 110. The guard 140 may be configured to extend axially past the injection conduit 122. In one embodiment, the guard 140 is configured to extend axially past the injection conduit 122 and lock axially relative to the housing 112 after removing the injection conduit 122 from the patient.

A sleeve 134 may be coupled to the fluid reservoir 118. The sleeve 134 may include a pair of diametrically opposed tabs 134a extending outwardly in the radial direction. The housing 112 may include a front retainer 136 coupled to the distal end of the housing 112. The front retainer 136 may include a pair of axially extending slots configured to receive the tabs 134a of the sleeve 134. The safety cap 114 may releaseably couple to the front retainer 136. The biasing member 138 may be positioned within the front retainer 136 and engage the distal end of the sleeve 134. The other end of the biasing member 138 may be configured to engage a flange proximate the distal end of the guard 140. The guard 140 may include a pair of diametrically opposed and axially extending slots 140c for receiving the tabs 134a. The axial range of motion of the guard 140 may be dictated by the ends of the slots 140c of the guard 140 engaging the tabs 134a of the sleeve 134. The guard 140 and the sleeve 134 may include one or more openings 140b, 134b respectively for aligning with a window 112a of the housing 112 to reveal the level of medicament in the fluid reservoir 118. The fluid reservoir 118 may include indicia that are visible through the window 112a so that the patient can verify that the appropriate volume of medicament is included in the injection device 110.

Referring to FIG. 8B, the firing mechanism may be automatically released based on the position of the injection conduit 122 relative to the patient. In one embodiment, retracting the guard 140 relative to the injection conduit 122 releases the firing mechanism. In other embodiments, the patient must actuate a button or another feature before or after retracting the guard 140, or in an embodiment not including a guard 140, in order to release the firing mechanism.

The injection device 110 may accommodate two injection volume adjustments. This may help to minimize the amount of unused drug. The first adjustment is set during assembly and sets the range of volume to be delivered (e.g., the dosing range). The dosing range may vary depending on the fill volume in the fluid reservoir 118. This amount may be set as part of the assembly process. In one embodiment, there are four configurations or SKUs. Each SKU will represent a maximum volume of fill to allow delivery of the maximum dose within that SKU (e.g., 0.8 to 1.0 ml volume delivery to the patient; 0.6 to 0.8 ml volume delivery to the patient; 0.4 to 0.6 ml volume delivery to the patient; and 0.2 to 0.4 ml volume delivery to the patient). The second adjustment is set by the user prior to injecting the medicament. The second volume adjustment sets the dose, a fraction of the volume in the fluid reservoir 118, and this dose to be delivered within the range allowed by the injection device 110. In one embodiment, the user may adjust the dose, up and down, until the injection is delivered.

Referring to FIGS. 5C-5F, the injection device 110 may be pre-primed for the user. In one embodiment, priming the injection device 110 allows for placing the ram 128 in a known position relative to the piston 120. Priming may be used to reduce an initial gap between the ram 128 and the piston 120 and/or compression in the piston 120 to allow for tight control of the dose expelled during triggering. Since the ram 128 moves a fixed (controlled based on the dose selected) displacement, minimizing the variability associated with the starting position of the ram 128 and controlling the end position of the ram 128 allows for greater accuracy of the delivered dose. Also, by providing a device that is already primed, there may be greater assurance that the patient will get the correct dosing by eliminating a step that the user might have to do and therefore eliminate an opportunity for the user to get this wrong.

The injection device 110 may be designed for assembly that eliminates the priming step. A filling process may be utilized to minimize air bubble in the fluid reservoir 118. Once the fluid reservoir 118 is inserted into a front assembly, including the safety cap 114, the front retainer 136, the guard 140 and the sleeve 134, is coupled with a middle assembly including the ram 128, the nut 130 and the latch 132. The connection between the distal end 128c of the ram and the piston 120 may be fully secured by rotating the nut 130 relative to the ram 128. The nut 130 may include one or more keyed features 130b (see FIG. 103b) such as a radially extending slot for coupling to a tool. Once the ram 128 and stopper 120 are sufficiently coupled, a rear assembly including the housing 114 may be positioned over the middle assembly and coupled to the front assembly and the dose mechanism 116 and biasing member 126 may be coupled to the middle assembly and the housing.

In some embodiments, the injection device 110 is primed by the user. Syringes are commonly supplied to autoinjector manufacturers in a 'drug-prefilled' state. The prefilling process fills the syringe with drug, and may use various methods including a vacuum process that attempts to remove as much air as possible inside the syringe chamber before a plug/stopper is placed, sealing the syringe. Bubble priming, whereby all or most of the air is expelled from the syringe chamber through the needle prior to injection, is extremely common in manual injections: a bubble in an intravenous injection can cause an air embolism in a patient. Unfortunately, bubble priming is not as simple in an auto-injector and the presence of an air bubble is detrimental to the accuracy & precision of an autoinjector's drug delivery mechanism, which commonly relies upon advancing a ram abutted to the piston a tightly controlled travel distance. The bubble cannot be removed (primed) from the syringe without removing the needle cap resulting in a breach of the sterile barrier.

When an appreciable force is applied to a syringe piston during an injection, any bubbles remaining trapped within the syringe will compress, or displace ejected fluid decreasing the injected volume. This is due to pressure induced by the ram, the incompressible nature of liquids, and compressibility of gas. A steady-state pressure equilibrium is then reached while the liquid drug is ejected until the ram reaches the end of its stroke. At the end of the ram stroke, any previously compressed gasses will expand to equilibrium with the ambient. The rate upon which the gas expands is variable and dependent upon the ram force, the viscosity of the liquid, bubble size, needle lumen size and length, and the ambient pressure. As the bubble pressure approaches ambient, the rate of fluid expulsion decays, increasing injection time (e.g., preferably less than 10 seconds) for injectors with combined viscous drug liquid and small needle lumens. As delivered volume is related to the travel of the syringe plunger, the amount of liquid drug that is encompassed within this travel distance is required to be constant to allow accurate dispensing of drug.

In order to bubble prime the injection device 110, the injection device 110 may be configured to be primed by the user by pointing the distal end 110a upward and advancing the ram 128 relative to the fluid reservoir 118. By pointing the distal end 110a of the injection device 110 upward, buoyancy of the bubble positions it directly adjacent to the proximal end of the needle 122. Depending upon the viscosity of the liquid, a slight tapping of the injection device 110 may be required. In some embodiments, the bubble may be observed through the window 112b in the housing 112.

In one embodiment, the injection device 110 is configured such that removing the safety cap 114 causes the ram 128 to advance a nominal predetermined distance, expelling the bubble and potentially a small amount of liquid from the needle 122. For example, a spacer may be provided between the latch 132 and the proximal flanged end of the fluid reservoir 118.

Figure 36:
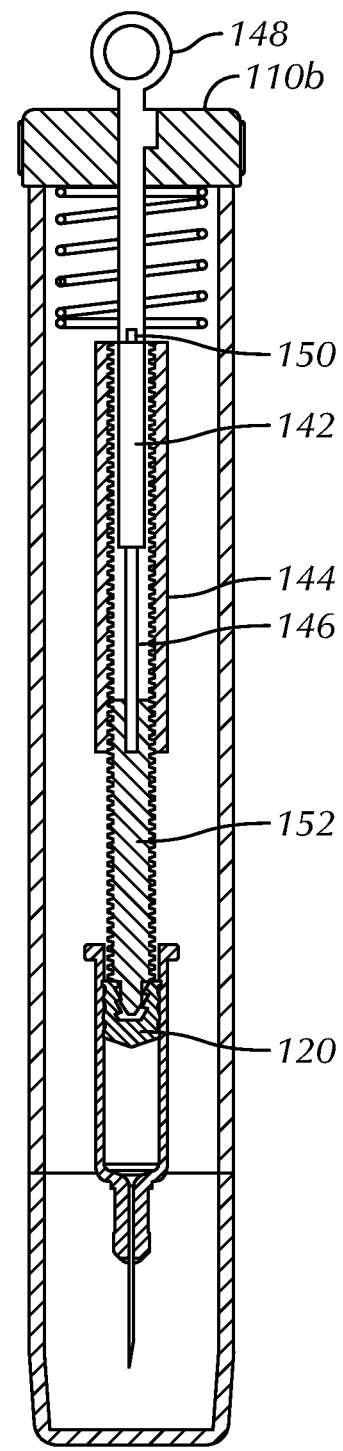
FIG. 36 is a side cross sectional sketch of the injection device of FIG. 19A having an expandable ram for priming.

Referring to FIG. 36, in some embodiments, the ram 128 is expanded to preload the piston 120. In one embodiment, the ram 128 includes two or more nesting elements. In one embodiment, a torsional spring 142 is nested in an outer ram 144. The torsional spring 142 may have a keyed rod 146 passing completely through the torsional spring, and rotationally constrained to the torsional spring. The keyed rod 146 may be locked by a removable release pin 148 extending from the distal end 110b of the injection device 110 and inserted into a keyed slot 150 of an inner ram 152 on the other end. The release pin may constrain the torsional spring until use. Upon removal, the torsional spring will rotate the inner ram relative to the outer ram, extending the inner ram to release the bubble (or provide a preload immediately prior to bubble expulsion).

Annular or partially annular teeth in the nested ram elements may interlock, (e.g., internal teeth on the outer cylinder/external teeth or slots on the inner cylinder) allowing only one way relative movement of the nested ram elements, inducing the ram 128 to extend and preload the piston 120. In one embodiment, instead of teeth, the nested ram elements are internally/externally threaded, allowing preload from rotation of a device element. In one embodiment, the ram 128 includes a three part ram 128 comprised of both one way-tooth interaction and threaded interactions.

The spacer or ram 128 may be coupled to the safety cap 114 such that removing the safety cap 114 removes the spacer or expands the ram 128 and preloading a force onto the piston 120. In other embodiments, the user actuates a trigger such as by pulling a pin, flipping a switch, pushing a button, that pulls the spacer out of the loading stack or device entirely or expands the ram 128. In one embodiment, setting the dose setting mechanism 116 automatically preloads piston 120. For example, instructions or indication to twist the dose setting mechanism 116 may be visible through window 112a even to set the injection device 110 to the maximum dose. This initial twist of the dose setting mechanism 116 may be used to extend the ram 128 to prime the injection device 110. The dosage indicia 116e may be oriented (rotated 180 degrees from example shown in FIG. 1) such that the number is readable when the distal end 110a of the injection device 110 is pointed up.

In one embodiment, removal of the safety cap 114 allows the guard 140, under spring load, to extend a predetermined distance. This movement allows a second spring loaded assembly connected to the ram to advance a nominal distance to a predetermined set-point, inducing an axial preload on the piston 120 (see FIGS. 32a and 32b as discussed further below). In one embodiment, the guard 140 is under a lower spring force than the firing mechanism such that coupling the priming of the injection device 110 to the guard 140 allows for the priming force to be controlled more precisely.

Once the safety cap 114 is removed, the fluid reservoir 118 may be bubble primed and ready for injection. A liquid receiver, such as a piece of absorbent material, may be positioned adjacent to the needle 122 toward the distal end 110a of the injection device 110 to capture any expelled liquid drug during priming. The liquid receiver may be in circumferential association with the needle 122 and may be attached to the housing 112, safety cap 114 or both (e.g., 2 pieces of absorbent material).

Following assembly, the injection device 110 is ready for use. Referring to FIG. 6B, during use of an exemplary embodiment, the user is aware what volume of medicament is provided in the injection device 110 and may verify by looking at the fluid reservoir 118 through the window 112b in the housing (see FIG. 1). The user then selects the desired dose to be delivered, either all or a fraction of the volume of the fluid reservoir 118, by rotating the dose setting mechanism 116 relative to the housing 112. The user may verify that the appropriate dosage is selecting by viewing the dosage amount indicated by the indicia visible through window 112a in the housing (see FIG. 1). FIG. 7B shows the injection device in a minimum dosage selection such that the ram 128 is pulled back from piston 120. The distance between the piston 120 and the ram 128 is the distance that will remain between the piston 120 and the distal end of the fluid reservoir 118. The medicament remaining in the fluid reservoir following the injection is not delivered and may be discarded.

Referring to FIG. 8B, once the dosage is set, the user removes the safety cap 114 (see FIG. 7B) from the front retainer 136 by pulling or twisting the safety cap 114 relative to the front retainer 136. Any priming is conducted if necessary, and the injection device 110 is ready for injection. The patient may then press the distal end of the guard 140 against their skin, retracting the guard 140 proximally until the needle 122 penetrates the skin surface and the proximal end 140d of the guard 140 contacts the slanted surface 132b of the latch 132.

Referring to FIG. 9B, once the proximal end 140d of the guard contacts the slanted surface 132b of the latch 132, the guard is further retracted to its fully retracted position, moving the stop 140e off of the pivot arm 132c of the latch and the proximal end 140d of the guard forces against the slanted surface 132b to pivot the pivot arm 132c and release the projection 132a of the latch 132 from the indentation 130a of the nut 130.

Referring to FIG. 10B, with the latch 132 released from the nut 130, the biasing member 126 is no longer restrained and the ram 128 and nut 130 are fired toward the distal end, urging the piston 120 distally and delivering the dose of medicament to the patient through the injection conduit 122.

Referring to FIGS. 12a and 12b, after the dose is delivered, the housing 112 is pulled away from the patient, pulling the needle 122 from the patient and allowing the biasing member 138 to urge the guard 140 distally past the end of the needle 122. A retaining member retains the guard 122 to lock the guard 140 relative to the needle 122 preventing further use of the injection device 110. The injection device 110 may then be safely discarded.

Referring to the drawings in detail, wherein like reference numerals indicate like elements throughout, there is shown in FIGS. 19A-35B an injection device, generally designated 210, a second exemplary embodiment of the present invention. Various embodiments of the injection device 210 are described in further detail below in reference to the exemplary embodiment shown in the figures. One or more of the embodiments discussed in reference to the injection device 210 described below may be combined with one or more desirable features of the embodiments discussed in reference to the injection device 110 described above.

The injection device 210 is configured to deliver a selected amount of one of a plurality of predetermined volumes of medicament to a patient. The injection device 210 is assembled using one of a plurality of fluid reservoirs 218 and the dose that is ultimately delivered to the patient is equal to or less than the full amount contained in the injection device 210. This allows for the injection device 210 to accept a fluid cartridge, prefilled syringe or similar container filled to different volumes and/or accept multiples sizes of containers and allow for the user to select how much of the fluid in the fluid container to deliver. Such flexibility allows for one device to be adapted for multiple medicament volumes and ultimately reduces the amount of wasted medicament.

For example, a typical injection device may have a volume of 1.0 ml to encompass the range of potential dosages needed. A patient who is provided a 1.0 ml device but only needs a dosage of 0.5 ml, would leave a residual volume of 0.5 ml in the discarded device. Instead, the patient, requiring a dosage of 0.5 ml, can be provided a 1.0 ml injection device 210 containing 0.6 ml of fluid, resulting in a residual volume of only 0.1 ml in the discarded device. By allowing adjustment of the volume, the manufacturer can easily set the injection device 210 to one of a plurality of volumes to divide up the range of dosages selectable by a patient and reduce the amount of residual fluid left in the discarded device.

The injection device 210 includes an actuator for driving fluid from the injection device 210 into the patient. In some embodiments, the actuator is automatically actuated as a result of positioning the injection device 210 relative to the skin surface, also referred to as an auto-injection device. The injection device 210 may include a needle. In other embodiments, the injection device does not include a needle and the injection port of the fluid chamber preferably defines a fluid pathway in fluid communication with the fluid chamber for injecting medicament as a jet from the chamber through the port to the injection location. An example of a suitable needle-free jet nozzle arrangement is disclosed in U.S. Pat. No. 6,309,371, which is incorporated by reference in its entirety.

As disclosed in further detail below, in some embodiments, the injection device 210 includes a firing mechanism having an actuator, a volume setting mechanism configured to be selectively preset during assembly to one of a plurality of positions based on a maximum volume of medicament to be delivered to the patient (e.g., one of a 0.4 ml, 0.6 ml, 0.8 ml or 1.0 ml prefilled syringe) and a dose setting mechanism configured to be selectably adjusted upon use, independent of the preset of the volume setting mechanism, to select a fraction of the maximum volume of medicament to be delivered to the patient (e.g., a 0.2 ml to 0.4 ml dose for a 0.4 ml syringe).

Figure 19A:
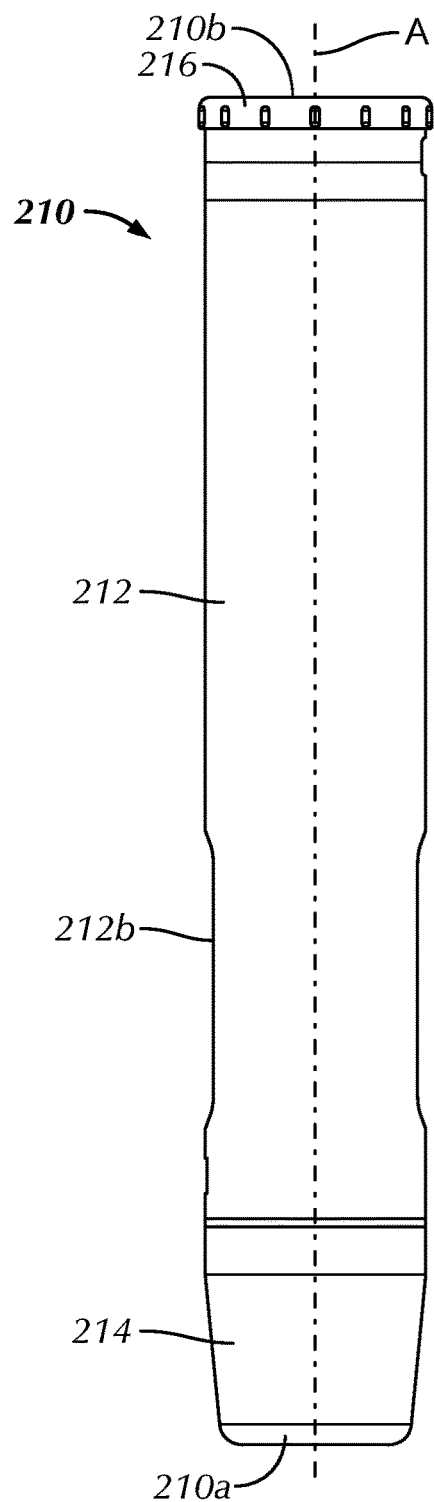
FIGS. 19A and 19B are side views of an injection device in accordance with an exemplary embodiment of the present invention.
Figure 19B:
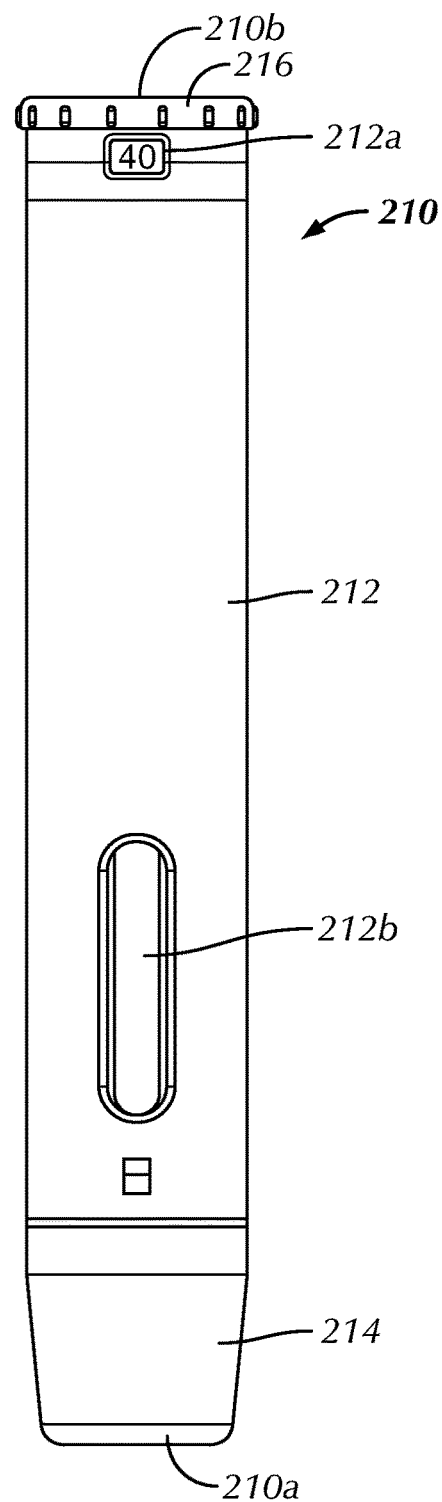

Referring to FIGS. 19A-19B, the injection device 210 may include a housing 212. The housing 212 extends along a longitudinal axis A and is configured to be held in one hand of a patient or caregiver to deliver the dose of medicament to the patient. In one embodiment, the housing 212 is cylindrical. In other embodiments, the cross sectional shape of the housing 212 is elliptical, triangular, square or any other desired shape. The housing 212 may include one or more windows 212a, 212b for viewing components of the injection device 210 contained within the housing 212. The windows 212a, 212b may be covered with a transparent material. Windows 212a, 212b may allow the viewing of the fluid reservoir within the housing 212. The window 212a, 212b may also allow viewing of the preset volume that has been chosen. In another embodiment, the window 212a, 212b allows viewing that the device is ready for use. In another embodiment, the window 212a, 212b allows the viewing the injection is complete. Other uses of a window to allow viewing internal aspects of the injection device are anticipated. In an embodiment, the window 212a, 212b allows viewing of injection device internal components that assist in administering an injection. In one embodiment, the housing 212 is comprised partially or entirely of a transparent material.

Figure 19C:
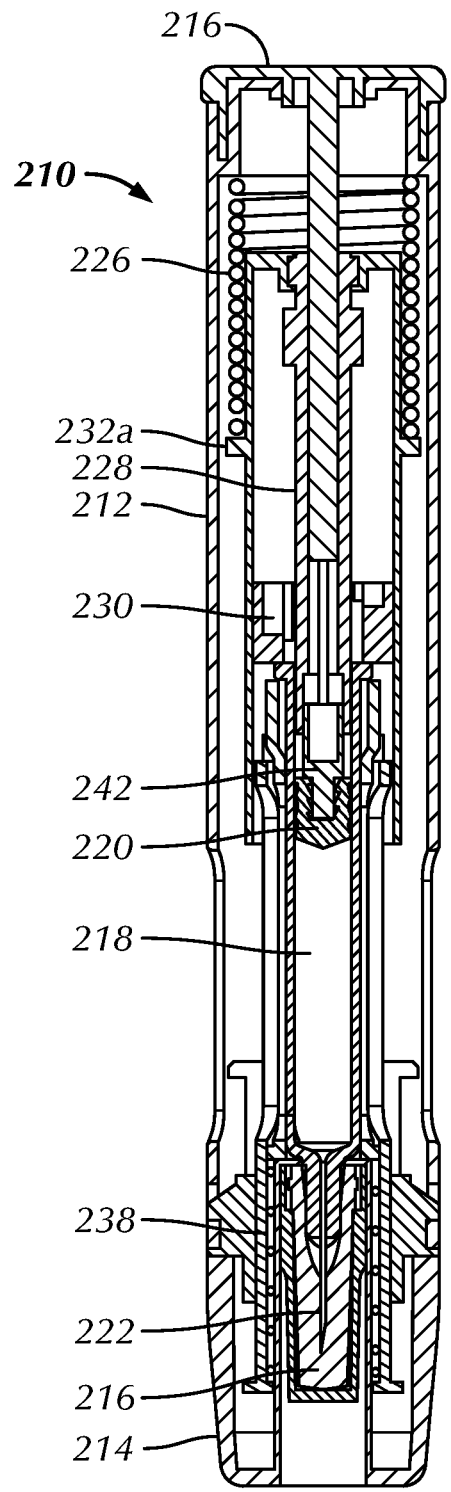
FIGS. 19C and 19D are side cross sectional views of the injection device of FIGS. 19A and 19B respectively.
Figure 19D:
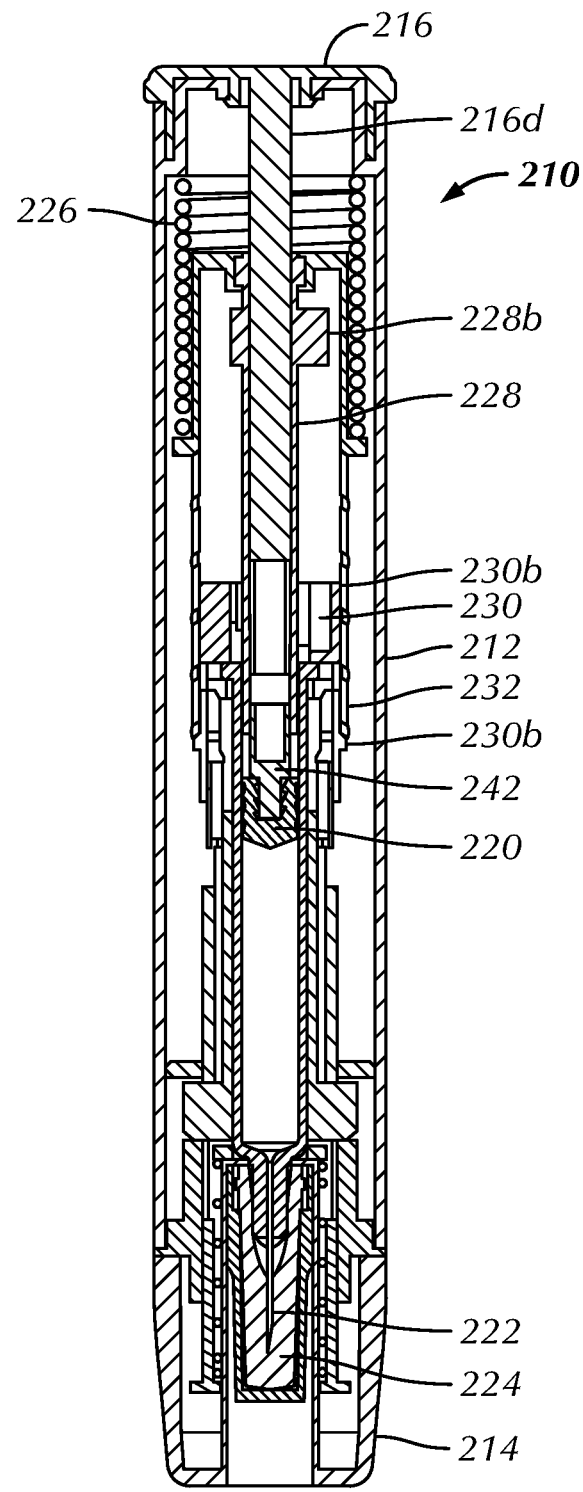

Referring to FIGS. 19C-19D, the housing 212 is configured to house a fluid reservoir 218 having one of a plurality of volumes of medicament. The volume of the fluid reservoir 218 is selected before assembling the injection device 210. In one embodiment, the volume of the selected fluid reservoir 218 is based on the desired maximum dose that the patient can inject. In one embodiment, the injection device 210 is configured to receive one sized container or syringe having a fluid reservoir 218 to accommodate a plurality (e.g., six) different maximum volumes for injection. In other embodiments, the injection device 210 is configured to receive a container having two, three, four, five, seven or more different maximum volumes for injection. In other embodiments, the injection device 210 is configured to receive six differently sized containers having fluid reservoirs 118. In other embodiments, the injection device 210 is configured to receive two, three, four, five, six, seven or more differently sized containers having fluid reservoirs 218. In one embodiment, the fluid reservoir 218 contains one of 0.4 ml, 0.6 ml, 0.8 ml, or 1.0 ml of medicament. In other embodiments, the fluid reservoir 218 contains other amounts of medicament such as one or more of the following amounts: 0.04 ml, 0.05 ml, 0.06 ml, 0.07 ml, 0.08 ml, 0.09 ml, 0.1 ml, 0.2 ml, 0.3 ml, 0.4 ml, 0.5 ml, 0.6 ml, 0.7 ml, 0.8 ml 0.9 ml, 1.0 ml, 1.1 ml, 1.2 ml, 1.3 ml, 1.4 ml, 1.5 ml, 1.6 ml, 1.7 ml, 1.8 ml, 1.9 ml, 2.0 ml, greater than 2.0 ml, less than 0.010 ml and any amount between these numbers. In one embodiment, the fluid reservoir 218 includes a prefilled syringe having a piston 220 forming a sliding seal at a proximal end. An injection conduit 222 is fluidly coupled to the fluid reservoir 218 defining a fluid pathway from the fluid reservoir 218 to the patient. In one embodiment, the injection conduit 222 is a needle. The needle 222 may be staked to the prefilled syringe.

The needle 222 may be covered by a needle cap 224 in the stowed or initial position. The needle cap 224 may include an elastomeric material for sealing and protecting the needle 222 in the initial position. The injection device 210 may further or alternatively include a safety cap 214 that is releaseably coupled to a distal end 210a of the injection device 210. The safety cap 214 covers the injection conduit 218 in the initial position to prevent contamination and accidental needle sticks or actuation of the actuator. The safety cap 214 may be coupled to the needle cap 224 such that removing the safety cap 214 from the housing 212 also strips the needle cap 224 from the needle 222 and exposes the needle 222.

The injection device 210 may include a firing mechanism coupled to the fluid reservoir 218 and configured to expel the medicament from the fluid reservoir 218 through the injection conduit 222. The injection device 210 may include an actuator such as a biasing member 226. In one embodiment, the biasing member 226 includes a compression spring. In another embodiment, the actuator is pneumatically driven. The biasing member 226 may be operatively associated with a ram 228 extending along the longitudinal axis A. The ram 228 may include a keyed shaft 228c (see FIG. 21B). The ram 228 may be coupled to the fluid reservoir 218 such that the biasing member 226 urges the ram 228 to compress the fluid reservoir 218 and deliver the medicament to the patient through the injection conduit 222. In one embodiment, the ram 228 is coupled to the piston 220. The ram 228 may include a prime screw 242 extending distally from the end of the ram 228 at selectively adjustable distances to maintain contact between the ram 228 and the piston 220 for priming purposes as discussed in further detail below.

Referring to FIGS. 21A-21C and 22A-22F, the volume setting mechanism may be set or configured during assembly of the injection device 210 to properly deliver the one of the plurality of volumes of medicament selected as the fluid reservoir 218. The volume setting mechanism may include a latch 232, a slot stop or stop 230 and a retainer 230a. The retainer 230a may be configured to retain the latch 232 relative to the slot stop 230. In one embodiment, the latch 232 is releaseably retained in the axial direction against a force of the biasing member 226 in an initial position by the retainer 230a. The latch 232 may include a radial projection such as a flange 232a configured to engage the end of the biasing member 226 (see FIG. 19C). The latch 232 may be axially fixed and rotatably coupled to the ram 228. The proximal end of the ram 228 may include a collar 228d that is rotatably received in a corresponding ring shaped groove in the latch 232. The slot stop 230 may be axially and rotatably fixed relative to the fluid reservoir 218. The ram 228 may include a radially extending wing 228b fixed to the ram 228. In other embodiments, the ram 228 includes two or more radially extending wings. As discussed further below, the slot stop 230 may be configured to set the axial position of the ram 228 relative to the fluid reservoir 218 and limit how far the ram 228 is permitted to travel relative to the fluid reservoir 218.

Figure 21A:
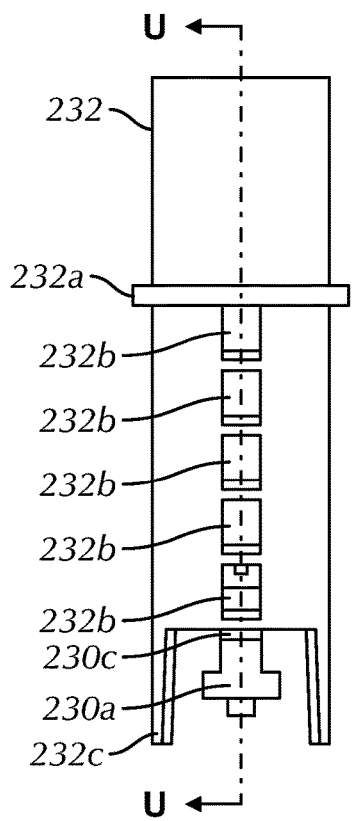
FIGS. 21A-21C are various side views of the latch, ram and slot stop of the injection device of FIG. 19A.
Figure 21B:
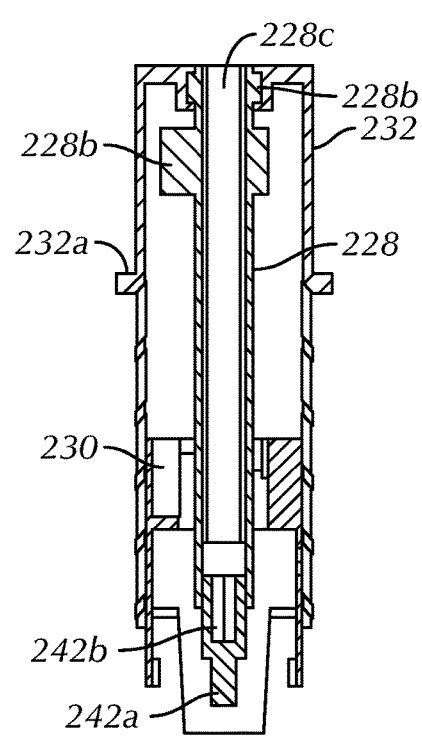
Figure 21C:
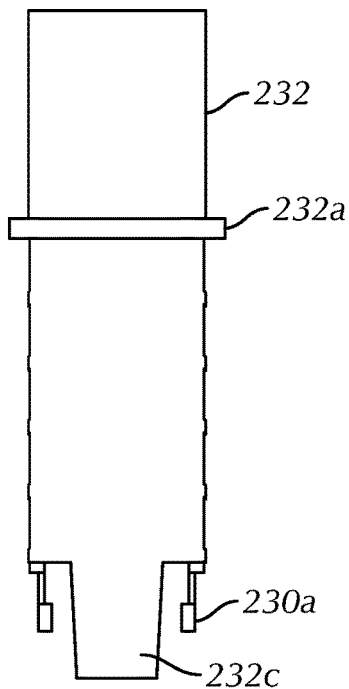
Figure 22A:
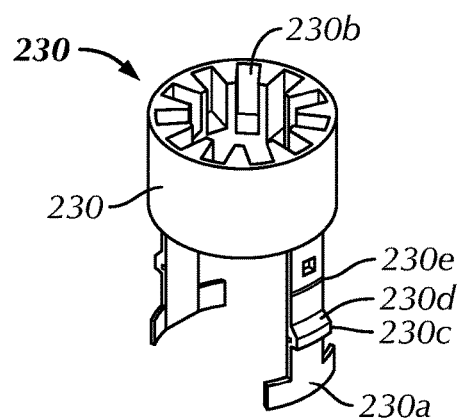
FIGS. 22A-22F are various views of the slot stop of the injection device of FIG. 19A.
Figures 22B, 22C, 22E:
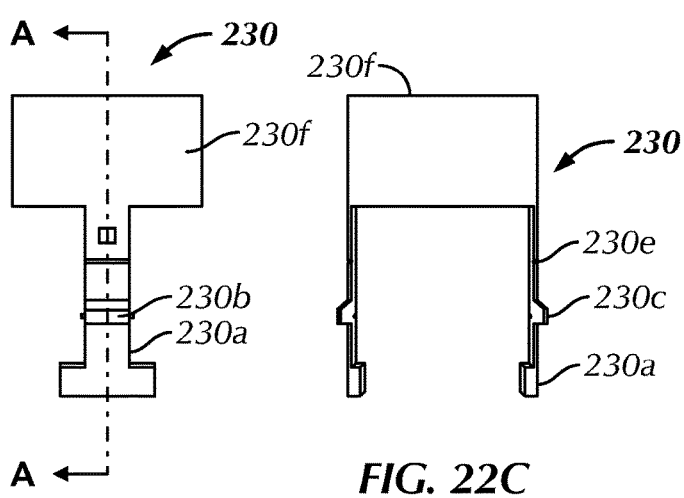
Figure 22D:
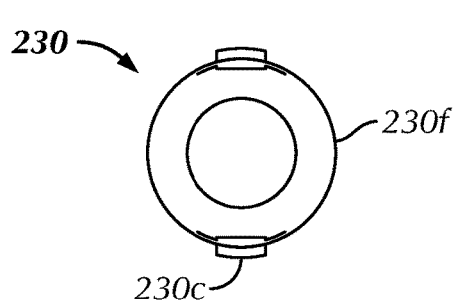
Figure 22F:
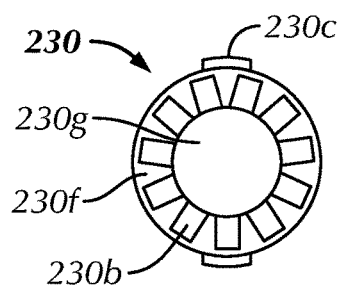
Figure 24A:
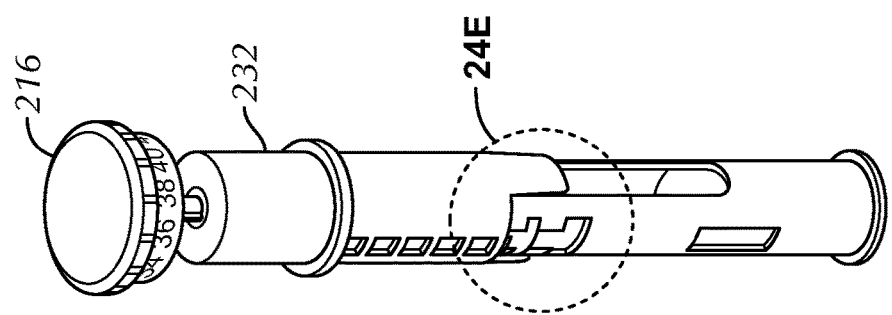
FIGS. 24A-24E are various side and perspective views of the injection device of FIG. 19A with the housing and other components removed in the initial, untriggered position.
Figure 24B:
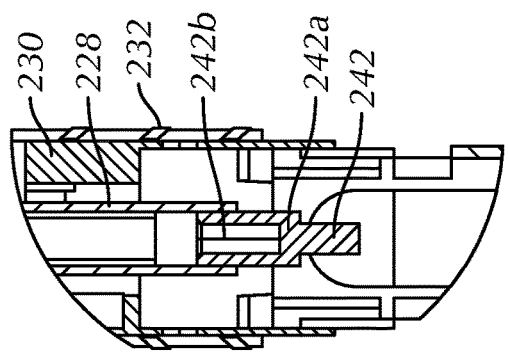
Figure 24C:
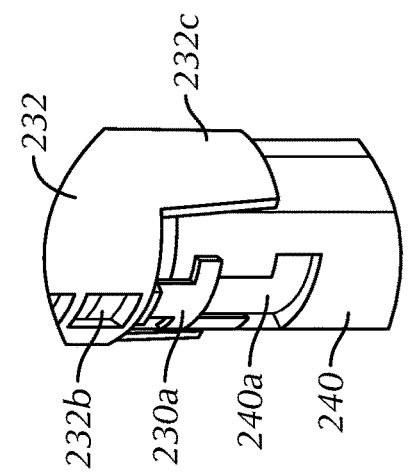
Figure 24D:
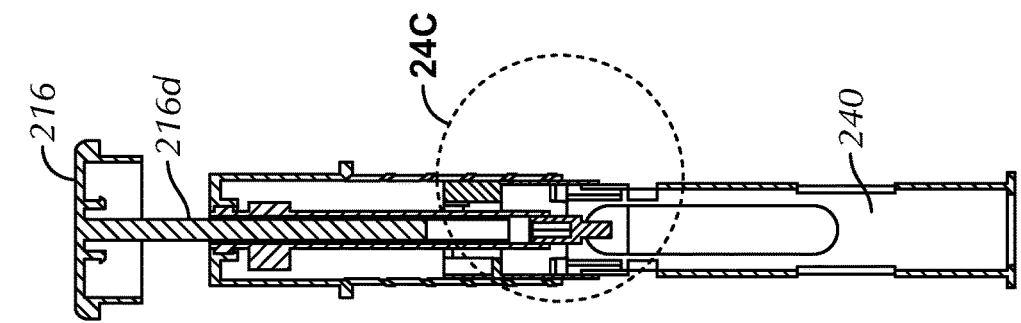
Figure 24E:
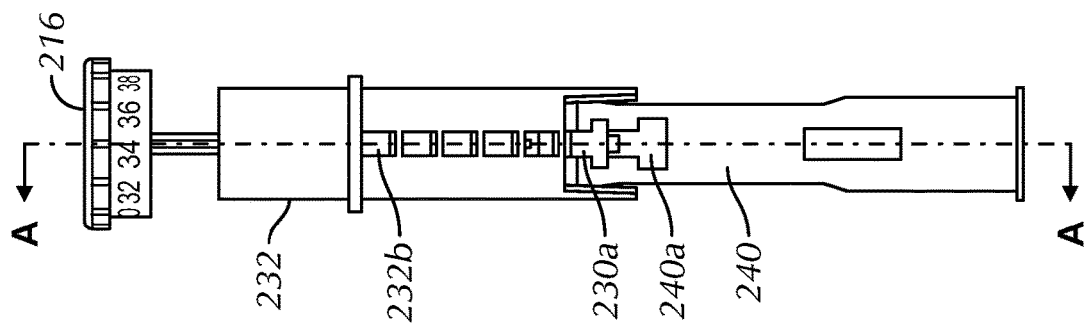
Figure 25D:
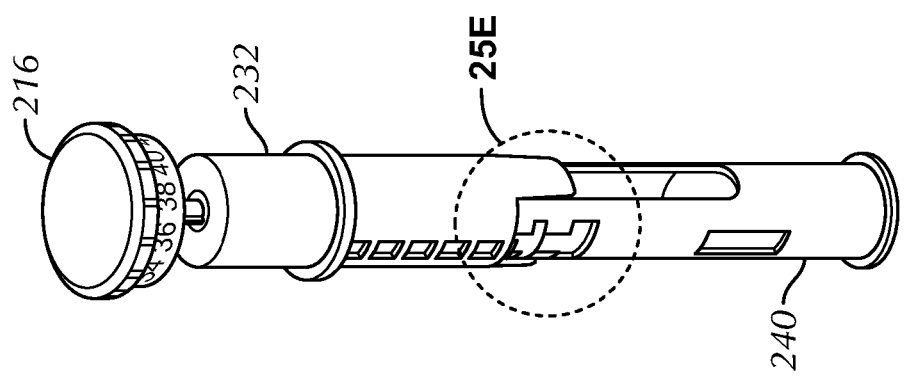
FIGS. 25A-25E are various side and perspective views of the injection device of FIG. 19A with the housing and other components removed in the insertion or retraction position.
Figure 25C:
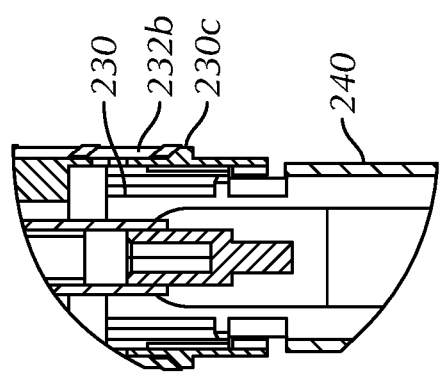
Figure 25E:
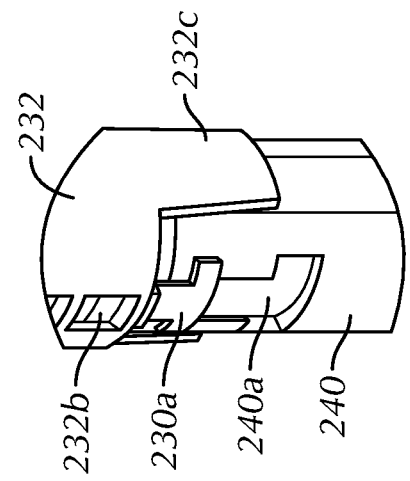
Figure 25B:
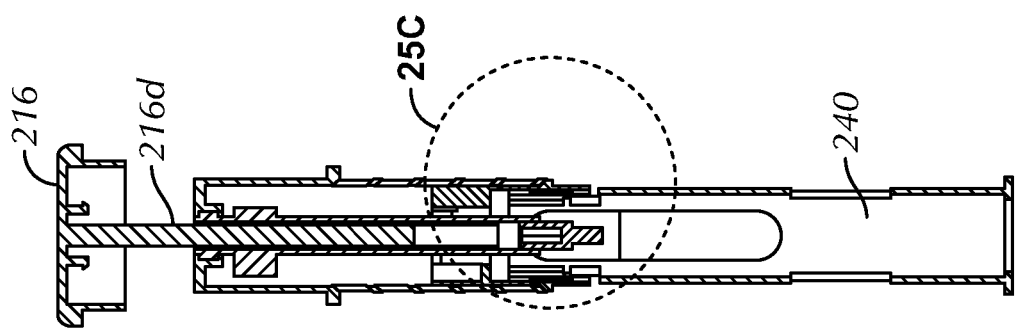
Figure 25A:
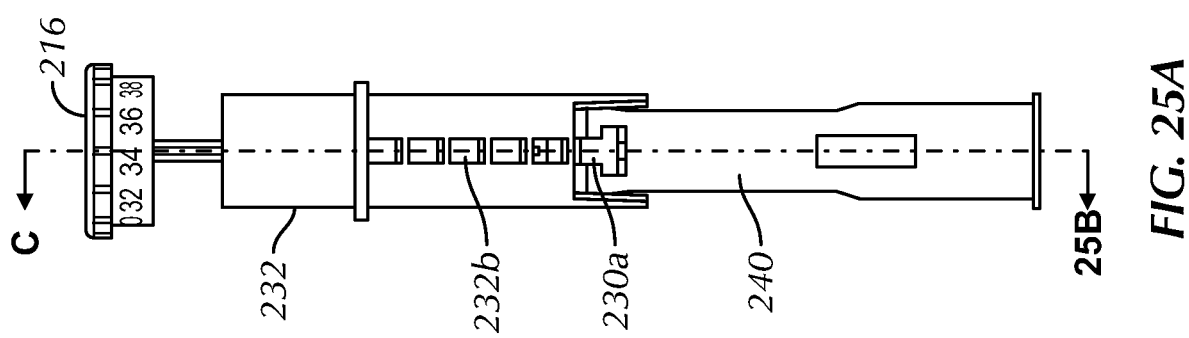

Referring to FIGS. 21A-21C, the latch 232 may include a plurality of radially extending features 232b, such as apertures, indents and/or projections, each configured to engage with the retainer 230a. Each of the plurality of radially extending features 232b may be axially spaced from one another. In one embodiment, such a configuration positions the distal end of the ram 228 relative to the fluid reservoir 218. During assembly of the injection device 210, the retainer 230a is configured to couple to the latch 232 in one of a plurality of positions along an axial length of the latch 232, each of the plurality of positions along the axial length of the latch 232 corresponding to one of the plurality of volumes of medicament of the fluid reservoir 218 for the firing mechanism to expel. In one embodiment, the latch 232 includes an additional set of radially extending features 232b closest to the proximal end to retain the latch 232 relative to the slot stop 230 at the end of delivery.

Figure 37:
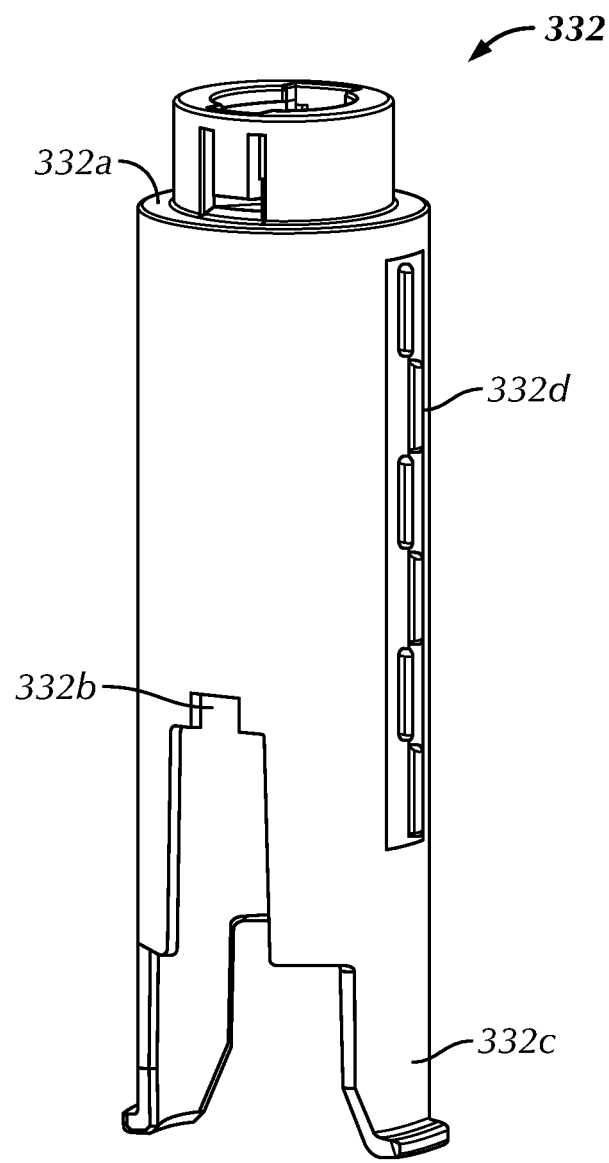
FIG. 37 is a perspective view of a latch for an injection device in accordance with an exemplary embodiment of the present invention.

Referring to FIG. 37, another embodiment of the latch 332 is shown. The latch 332 may include a single, radially extending feature 332b configured to engage with the retainer 230a. In one embodiment, the radially extending feature 332b is a window or cut-out. The axial depth or height of the radially extending feature 332b may be predetermined, and one of a plurality of latches 332 is selected based on the axial depth or height of its radially extending feature 332b. The latch 332 that is selected will depend on the desired one of the plurality of volumes of medicament of the fluid reservoir 218 for the firing mechanism to expel. The latch 332 may include one or more alignment features 332d that engage a corresponding feature of the housing to prevent the latch 332 from rotating relative to the housing during firing. In one embodiment, the alignment features 332d include a plurality of opposed and axially spaced projections that are configured to engage a rib extending axially and projecting radially inward from the housing.

Referring to FIGS. 21A-21C, the wing 228b of the ram 228 may be configured to engage a stop fixed relative to the fluid delivery device 210 at the end of the delivery stroke as discussed below. As a result, the distance the ram 228 extends distally from a bottom surface 230h of the slot stop 230, in some embodiments, is set to correspond to the volume of the fluid reservoir 218 (e.g., the axial distance between the piston 220 and the bottom surface 230h of the slot stop 230). For example, the position of the latch 232 relative to the slot stop 230 in the maximum position illustrated in FIGS. 21A-21C corresponds to a volume of a 1.0 ml fluid reservoir 218. If a 0.8 ml fluid reservoir 218 is used for example, then the slot stop 230 may be move proximally relative to the latch 232 to engage the projection 230c of the retainer 230a with the next proximal radially extending feature 232b of the latch 232 and extend the ram 228 further toward the distal end 210a of the injection device 210.

Referring to FIGS. 22A-22F, the retainer 230a may be integrally formed with the slot stop 230. In other embodiments, the retainer 230a is a separate component from slot stop 230. The retainer 230a may be a cantilever arm. In one embodiment the retainer 230a has one or more circumferentially extending protections to form an upside down capital letter T or Y shape. In one embodiment, two or more retainers 230a are provided. In one embodiment, two diametrically opposed retainers 230a are provided. The retainer 230a may be configured to radially deflect inward about an inflection point 230e. In one embodiment, inflection point 230e includes a groove or recess to help facility bending of the material. The retainer 230a may include a projection 230c that engages a corresponding radially extending feature 232b (see FIG. 21A) to prevent axial movement of the latch 232 in the initial position. The projection 230c may include a sloped top surface 230d to help facilitate translating the axial force exerted on the retainer 230a into a radial deflection of the retainer 230a to move the projection 230c from interfering with axial motion of the latch 232 in the triggered or released position.

Once the latch retainer 230a is disengaged from the latch 232, the latch 232 and ram 228 are released axially and fired distally by the biasing member 226. In other embodiments, the latch 232 and retainer 230a have the reverse mating relationship to the configuration described above such that the radially extending features 232b are protrusions that are engageable by an indent or aperture in the retainer 230a.

In one embodiment, setting the volume by coupling the slot stop 230 to the latch 232 at one of a plurality of locations results in an adjustment of the spring force by biasing member 226. By moving the slot stop 230 axially relative to the latch 232 to set the volume, the biasing member 226 may be more compressed for the larger volumes and less compressed for the smaller volumes. The rate of delivery for a larger dose may therefore be higher than the rate of delivery for a smaller dose resulting in a generally equal amount of time to deliver each dose. In some embodiments, the delivery time is not equal for each dose but closer to being equal than if the rate of delivery was instead constant. Referring to FIG. 2 for example, a dose of 1.0 ml may be delivered in approximately 7-10 seconds and a dose of 0.6 ml may be delivered in approximately 6-9 seconds. Such a configuration, where the variability between delivery times for each dose is minimized, may be desirable for compliance. For example, a patient who starts a treatment at a lower volume may be accustomed to waiting a certain amount of time to deliver a dose and be inclined to wait the same amount of time even if the treatment is adjusted to a higher volume. An amount of spring decay may be selected such that any differences in injection time between volumes do not result in improper use of the device.

TABLE 2

| Range of delivery times | |
| --- | --- |
| Delivered Vol. (ml) | Injection time range (sec) |
| 1.0 | 7-10 |
| 0.8 | 7-9 |
| 0.6 | 6-8 |
| 0.4 | 5-8 |
| 0.2 | 4-7 |

It may be desirable to provide a spring with a spring force decay curve where such that the difference in injection time between the volumes is such that the user does not perceive a significant difference.

Referring to FIGS. 19C-20B, the injection device 210 may include a dose setting mechanism 216 configured to select a fraction of the one of the plurality of volumes of medicament that is injected from the injection conduit 222 when the firing mechanism is actuated. The dose setting mechanism 216 may include a knob rotatably coupled to the housing. In one embodiment, the dose setting mechanism 216 caps the proximal end of the housing 212. The dose setting mechanism 216 may include a grip portion 216a for grasping by the patient. The grip portion 216a may include one or more features such as axially extending and radially projecting ribs 216a for increasing the frictional force between the dose setting mechanism 216 and a user's hand during use. The dose setting mechanism 216 may include a dosage level portion 216b having a plurality of dosage indicia 216e. The dose setting mechanism 216 may include a shaft 216d for coupling to the ram 228.

Referring to FIGS. 19C-19D and 24A-24E, the dose setting mechanism 216 may be rotatably moveable relative to the housing 212. In one embodiment, the dose setting mechanism 216 is fixed axially relative to the housing 212. The dose setting mechanism 216 may be rotatably fixed and axially moveable relative to the ram 228. The interior shaft 228c (see FIGS. 21B and 23) of the ram 228 may have a keyed shape that corresponds to the shape (such as projections 216f) of the shaft 216d of the dose setting mechanism 216 such that rotating the dose setting mechanism 216 rotates the ram 228, and rotates the wing 228b relative to the slot stop 230 (see FIG. 28C). When the dose setting mechanism 216 is rotated, indicia 216e corresponding to the radial position of the wing 228b may align with the window 212a in the housing 212 to display the selected dosage to the patient. In one embodiment, rotating the dose setting mechanism 216 to rotate the ram 228 does not impact the position and force on the biasing member 226. In some embodiments, the dose setting mechanism 216 includes a resistance and/or an audible click between selected dosages.

Referring to FIGS. 22A-22F, the slot stop 230 may include a body 230f. The body 230f may be held stationary with respect to the fluid reservoir 218. In one embodiment, the body 230f includes a hole 230g extending there through to allow the ram 228 to pass through the slot stop 230 (see FIG. 21B). The slot stop 230 may include a plurality of axially extending and radially projecting slots 230b. In one embodiment, the slots 230b are open toward the hole 230g. The slots 230b may be sized and configured to receive the wing 228b in the fired position. The slots 230b may have different axial depths such that the wing 228b is stopped different distances from a bottom surface 230h of the body 230f and therefore stops the distal end of the piston at different distances relative to the fluid reservoir 218. The wing 228b may include a pointed bottom edge 228c and/or the slot stop 230 may include pointed spaces between each of the slots 230b to help ensure that the wing 228b is guided into the appropriate slot 230b. In one embodiment, the slots 230b have an increasing axial depth from one slot 230b to an adjacent slot 230b moving around the hole 230g. In other embodiments, every other slot 230b has an increasing axial depth if two diametrically opposed wings 228b are provided, for example.

Referring to FIGS. 19C-21C, the injection device 210 may be pre-primed for the user. In one embodiment, priming the injection device 210 allows for placing the ram 228 in a known position relative to the piston 220. Priming may be used to reduce an initial gap between the ram 228 and the piston 220 and/or compression in the piston 220 to allow for tight control of the dose expelled during triggering. Since the ram 228 moves a fixed (controlled based on the dose selected) displacement, minimizing the variability associated with the starting position of the ram 228 and controlling the end position of the ram 228 allows for greater accuracy of the delivered dose. Also, by providing a device that is already primed, there may be greater assurance that the patient will get the correct dosing by eliminating a step that the user might have to do and therefore eliminate an opportunity for the user to get this wrong. The injection device 210 may be designed for assembly that eliminates the priming step. A filling process may be utilized to minimize air bubble in the fluid reservoir 218. Once the fluid reservoir 218 is inserted into a front assembly, including the safety cap 214, the front retainer 236, the guard 240 and the sleeve 234, is coupled with a middle assembly including the ram 228, the latch 232 and the slot stop 230 (selectively coupled to the desired axial position on the latch 232) which is then coupled with a rear assembly including the biasing member 226, the housing 212 and the dose setting mechanism 216.

After setting the volume setting mechanism and before attaching or sealing off the dose setting mechanism, the ram 228 may be primed. In one embodiment, the ram 228 is primed using a prime screw 242. The prime screw 242 may be threadably attached to the ram 228 to adjust how far axially the prime screw 242 extends from the ram 228. The prime screw 242 may include a keyed feature 242b such that a corresponding tool may be inserted through the shaft 228c of the ram 228 to rotate the prime screw 242 and adjust the position of the distal end 242a of the prime screw 242 relative to the piston 220. In one embodiment, the distal end 242a is configured to be in contact with the piston 220 in the initial position independent of the position of the dose mechanism 216.

In one embodiment, the distal end 242a of the prime screw 242 is in contact with the piston 220 in the initial position such that the ram 228 does not move relative to piston 220 during triggering. By eliminating an axial space between the piston 220 and the ram 228 in the initial position, the ram 228 may be prevented from dynamically impacting the piston 220 once the injection device 210 has been fired, referred to as "shock loading". In some embodiments, the patient may feel or hear the impact between the ram 228 and the piston 220 if there is shock loading and/or the impact may potentially damage the syringe. In certain embodiments, a gap between the ram 228 and the piston 220 is provided if desired.

Referring to FIGS. 32-35B, in some embodiments, the injection device 210 is primed by the user. Syringes are commonly supplied to autoinjector manufacturers in a 'drug-prefilled' state. The prefilling process fills the syringe with drug, and may use various methods including a vacuum process that attempts to remove as much air as possible inside the syringe chamber before a plug/stopper is placed, sealing the syringe. Bubble priming, whereby all or most of the air is expelled from the syringe chamber through the needle prior to injection, is extremely common in manual injections: a bubble in an intravenous injection can cause an air embolism in a patient. Unfortunately, bubble priming is not as simple in an autoinjector and the presence of an air bubble is detrimental to the accuracy and precision of an autoinjector's drug delivery mechanism, which commonly relies upon advancing a ram abutted to the piston a tightly controlled travel distance. The bubble cannot be removed (primed) from the syringe without removing the needle cap resulting in a breach of the sterile barrier.

When an appreciable force is applied to a syringe piston during an injection, any bubbles remaining trapped within the syringe will compress, or displace ejected fluid decreasing the injected volume. This is due to pressure induced by the ram, the incompressible nature of liquids, and compressibility of gas. A steady-state pressure equilibrium is then reached while the liquid drug is ejected until the ram reaches the end of its stroke. At the end of the ram stroke, any previously compressed gasses will expand to equilibrium with the ambient. The rate upon which the gas expands is variable and dependent upon the ram force, the viscosity of the liquid, bubble size, needle lumen size and length, and the ambient pressure. As the bubble pressure approaches ambient, the rate of fluid expulsion decays, increasing injection time (e.g., preferably less than 10 seconds) for injectors with combined viscous drug liquid and small needle lumens. As delivered volume is related to the travel of the syringe plunger, the amount of liquid drug that is encompassed within this travel distance is required to be constant to allow accurate dispensing of drug.

In order to bubble prime the injection device 210, the injection device 210 may be configured to be primed by the user by pointing the distal end 210a upward and advancing the ram 228 relative to the fluid reservoir 218. By pointing the distal end 210a of the injection device 210 upward, buoyancy of the bubble positions it directly adjacent to the proximal end of the needle 222. Depending upon the viscosity of the liquid, a slight tapping of the injection device 210 may be required. In some embodiments, the bubble may be observed through the window 212b in the housing 212.

Figure 33C:
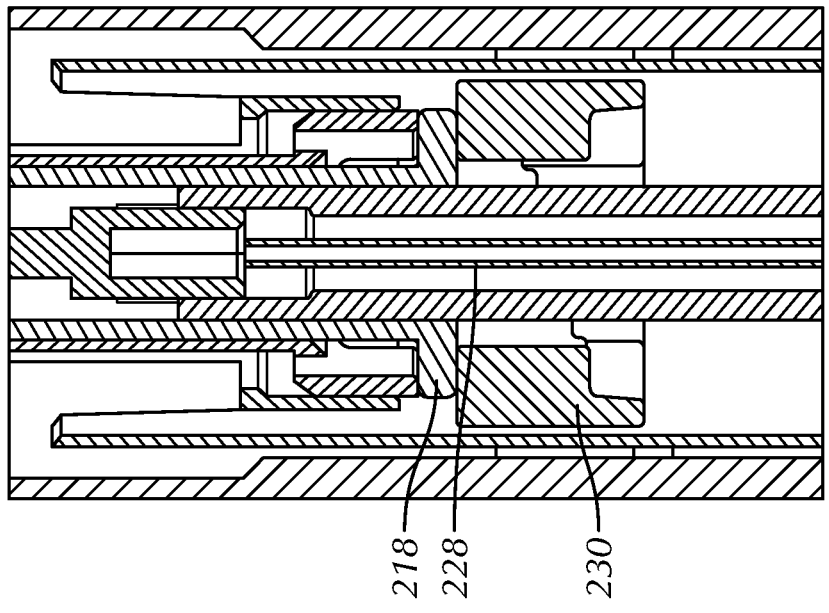
Figure 33D:
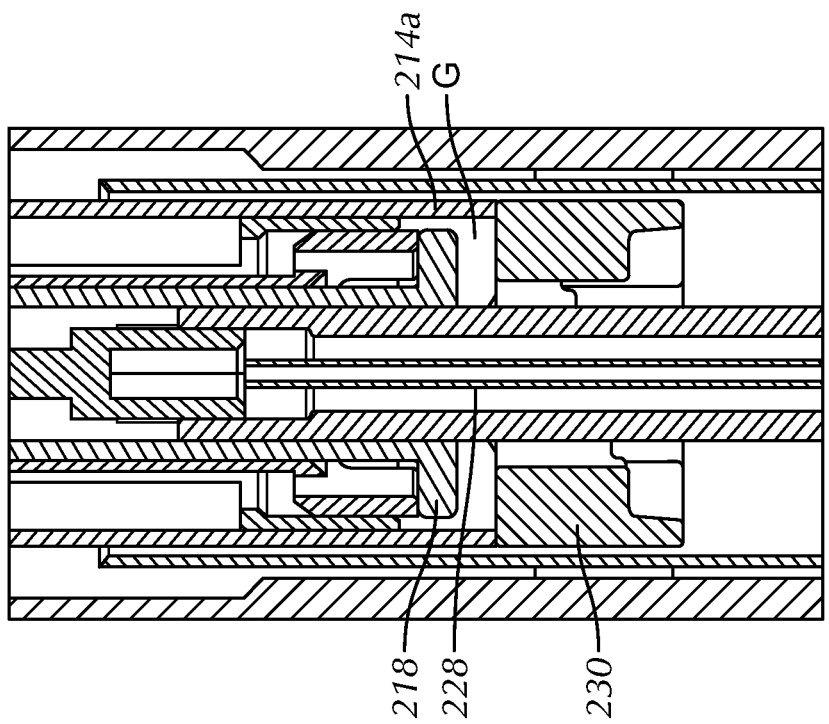

Referring to FIGS. 32-33D, in one embodiment, the injection device 210 is configured such that removing the safety cap 214 causes the ram 228 to advance a nominal predetermined distance, expelling the bubble from the fluid reservoir 218 and potentially a small amount of liquid from the needle 222. For example, a spacer 214a may be provided between the latch 232 and the proximal flanged end of the fluid reservoir 218. In one embodiment, the spacer 214a is a sleeve that extends proximally from the safety cap 214 to retain the slot stop 230 a distance G from a proximal end of the fluid reservoir 218. Removing the spacer 214a allows the firing mechanism, including the ram 228, to advance the distance G and have the slot stop 230 abut against the proximal end of the fluid reservoir 218 or whatever feature is coupled to the proximal end of the fluid reservoir 218 such as a bumper.

Referring to FIG. 36, in some embodiments, the ram 228 is expanded to preload the piston 220. In one embodiment, the ram 228 includes two or more nesting elements. In one embodiment, a torsional spring 142 is nested in an outer ram 144. The torsional spring 142 may have a keyed rod 146 passing completely through the torsional spring, and rotationally constrained to the torsional spring. The keyed rod 146 may be locked by a removable release pin 148 extending from the distal end 210b of the injection device 210 and inserted into a keyed slot 150 of an inner ram 152 on the other end. The release pin may constrain the torsional spring until use. Upon removal, the torsional spring will rotate the inner ram relative to the outer ram, extending the inner ram to release the bubble (or provide a preload immediately prior to bubble expulsion).

Annular or partially annular teeth in the nested ram elements may interlock, (e.g., internal teeth on the outer cylinder/external teeth or slots on the inner cylinder) allowing only one way relative movement of the nested ram elements, inducing the ram 228 to extend and preload the piston 220. In one embodiment, instead of teeth, the nested ram elements are internally/externally threaded, allowing preload from rotation of a device element. In one embodiment, the ram 228 includes a three part ram 228 comprised of both one way-tooth interaction and threaded interactions.

The spacer or ram 228 may be coupled to the safety cap 214 such that removing the safety cap 214 removes the spacer or expands the ram 228 and preloads a force onto the piston 220. In other embodiments, the user actuates a trigger such as by pulling a pin 244 (see FIGS. 34a-34B), flipping a switch, pushing a button, that pulls the spacer out of the loading stack or device entirely or expands the ram 228. In one embodiment, setting the dose setting mechanism 216 automatically preloads piston 220. For example, instructions or indication to twist the dose setting mechanism 216 may be visible through window 212a even to set the injection device 210 to the maximum dose. This initial twist of the dose setting mechanism 216 may be used to extend the ram 228 to prime the injection device 210. The dosage indicia 216e may be oriented (rotated 180 degrees from example shown in FIG. 19B) such that the number is readable when the distal end 210a of the injection device 210 is pointed up.

Figure 35A:
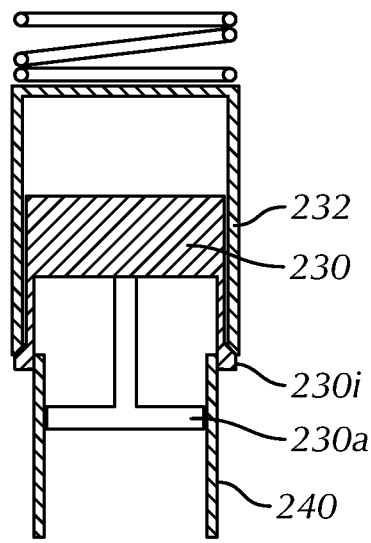
FIGS. 35a and 35b are cross sectional sketches of the latch, slot stop and guard of the injection device of FIG. 19A illustrating a priming configuration.
Figure 35B:
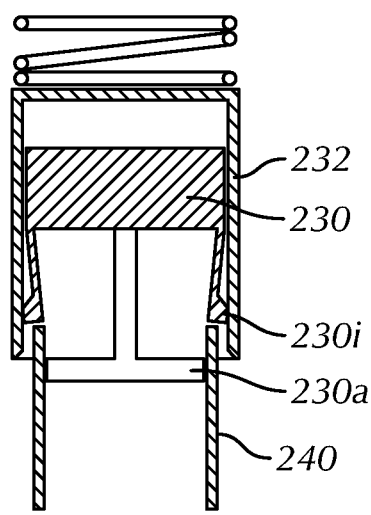

Referring to FIGS. 35a and 35b, in one embodiment, removal of the safety cap 214 allows the guard 240, under spring load, to extend a predetermined distance. This movement allows for one or more prime arms 230i to deflect radially inward and cause the second spring loaded assembly connected to the ram to advance a nominal distance to a predetermined set-point, inducing an axial preload on the piston 220. In one embodiment, the guard 240 is under a lower spring force than the firing mechanism such that coupling the priming of the injection device 210 to the guard 240 allows for the priming force to be controlled more precisely.

Once the safety cap 214 is removed, the fluid reservoir 218 may be bubble primed and ready for injection. A liquid receiver, such as a piece of absorbent material, may be positioned adjacent to the needle 222 toward the distal end 210a of the injection device 210 to capture any expelled liquid drug during priming. The liquid receiver may be in circumferential association with the needle 222 and may be attached to the housing 212, safety cap 214 or both (e.g., 2 pieces of absorbent material).

Referring to FIGS. 19C and 27A-27D, the injection device 210 may configured to prevent resetting after the firing mechanism is actuated so as to prevent a subsequent injection of the medicament by the injector, thereby configuring the injection device 210 as a single-use injector. In one embodiment, the injection device 210 includes a guard 240 that is slideably coupled to the housing 212. The injection device 210 may include a biasing member 238 coupled to the guard 240 and configured to bias the guard 240 toward a distal end 210a of the injection device 210. The guard 240 may be configured to extend axially past the injection conduit 222. In one embodiment, the guard 240 is configured to extend axially past the injection conduit 222 and lock axially relative to the housing 212 after removing the injection conduit 222 from the patient.

Figure 20A:
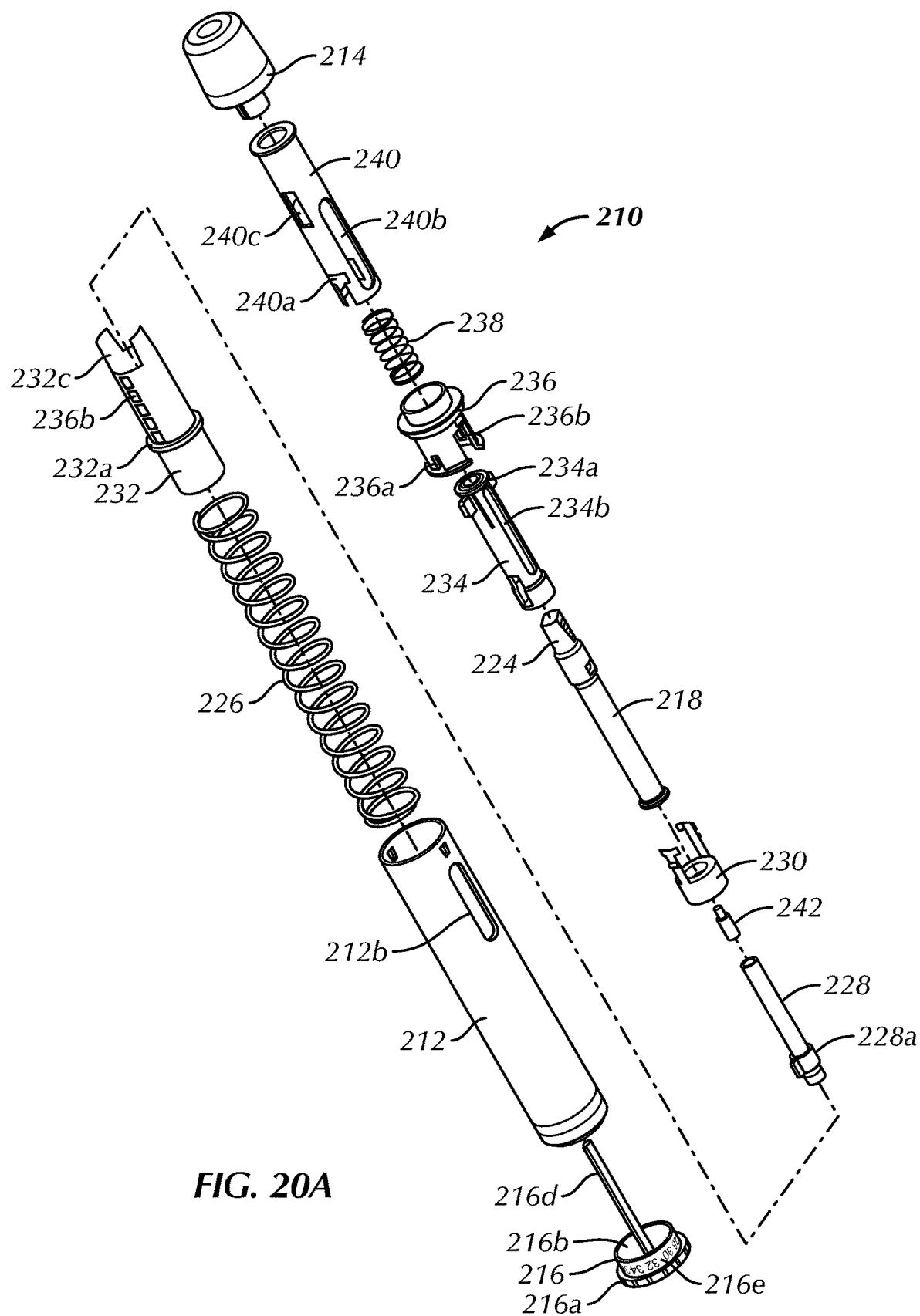
FIG. 20A is a first exploded perspective view of the injection device of FIG. 19A.
Figure 20B:
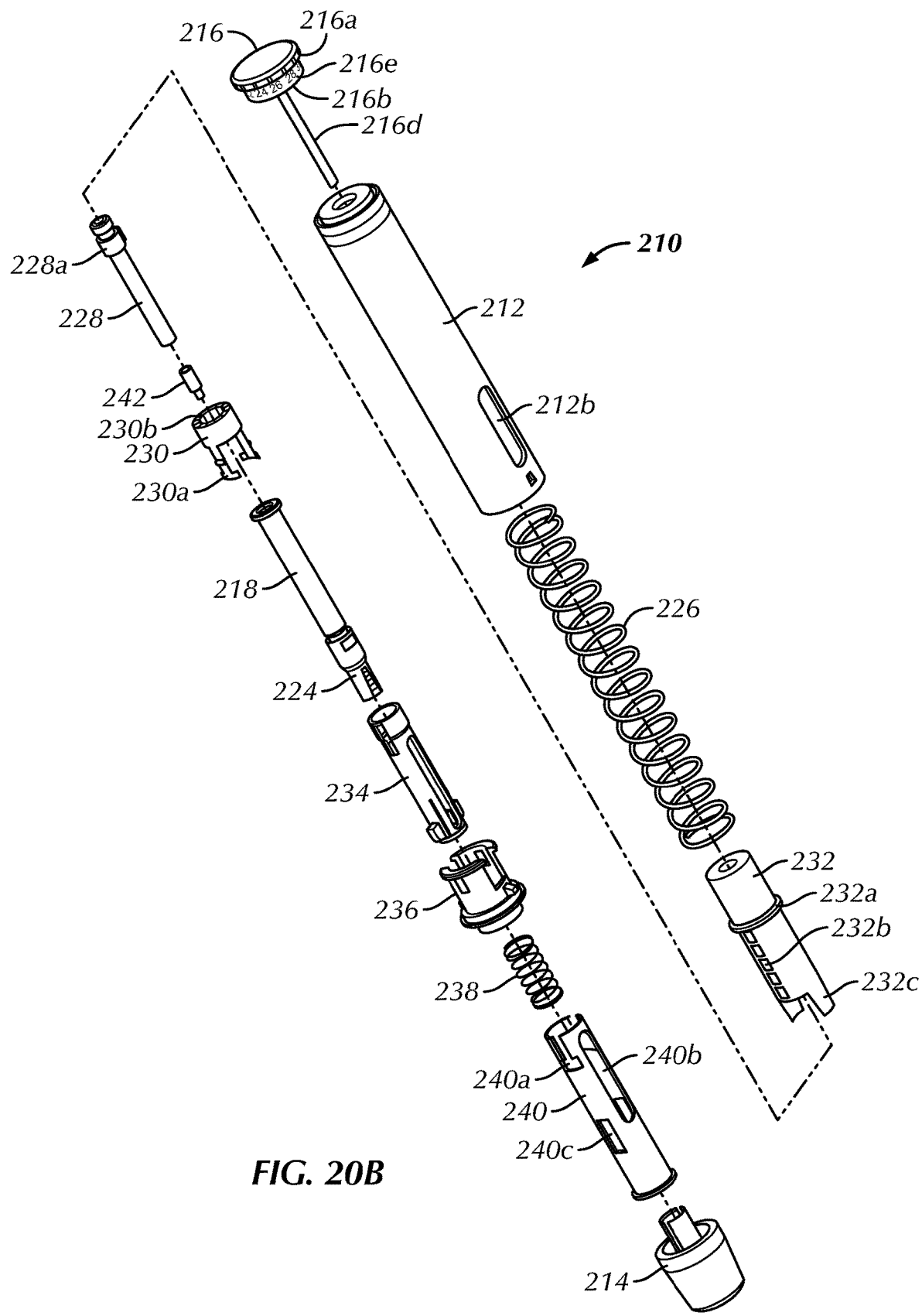
FIG. 20B is a second exploded perspective view of the injection device of FIG. 19A.

Referring to FIGS. 20A-20B, a sleeve 234 may be coupled to the fluid reservoir 218. The sleeve 234 may include a pair of diametrically opposed tabs 234a extending outwardly in the radial direction. The housing 212 may include a front retainer 236 coupled to the distal end of the housing 212. The front retainer 236 may include a pair of axially extending slots 236a configured to receive the tabs 234a of the sleeve 234. The safety cap 214 may releaseably couple to the front retainer 236. The biasing member 238 may be positioned within the front retainer 236 and engage the distal end of the sleeve 234. The other end of the biasing member 238 may be configured to engage a flange proximate the distal end of the guard 240. The guard 240 may include a pair of diametrically opposed and axially extending slots 240c for receiving the tabs 234a. The axial range of motion of the guard 240 may be dictated by the ends of the slots 240c of the guard 240 engaging the tabs 234a of the sleeve 234. The guard 240 and the sleeve 234 may include one or more openings 240b, 234b respectively for aligning with a window 212b of the housing 212 to reveal the level of medicament in the fluid reservoir 218. The fluid reservoir 218 may include indicia and/or the level of fluid contained therein that are visible through the window 212b so that the patient can verify that the appropriate volume of medicament is included in the injection device 210.

Referring to FIGS. 24A-27D, the firing mechanism may be automatically released based on the position of the injection conduit 222 relative to the patient. In one embodiment, retracting the guard 240 relative to the injection conduit 222 releases the firing mechanism. In other embodiment, the patient must actuate a button or another feature before or after retracting the guard 240, or in an embodiment not including a guard 240, in order to release the firing mechanism.

The injection device 210 may accommodate two injection volume adjustments. This may help to minimize the amount of unused drug. The first adjustment is set during assembly and sets the range of volume to be delivered (e.g., the dosing range). The dosing range may vary depending on the fill volume in the fluid reservoir 218. This amount may be set as part of the assembly process. In one embodiment, there are four configurations or SKUs. Each SKU will represent a maximum volume of fill to allow delivery of the maximum dose within that SKU (e.g., 0.8 to 1.0 ml volume delivery to the patient; 0.6 to 0.8 ml volume delivery to the patient; 0.4 to 0.6 ml volume delivery to the patient; and 0.2 to 0.4 ml volume delivery to the patient). The second adjustment is set by the user prior to injecting the medicament. The second volume adjustment sets the dose, a fraction of the volume in the fluid reservoir 218, and this dose to be delivered within the range allowed by the injection device 210. In one embodiment, the user may adjust the dose, up and down, until the injection is delivered.

Referring to FIGS. 24A-24E, during use of an exemplary embodiment, the user is aware what volume of medicament is provided in the injection device 210 and may verify by looking at the fluid reservoir 218 through the window 212b in the housing (see FIGS. 20A-20B). The user then selects the desired dose to be delivered, either all or a fraction of the volume of the fluid reservoir 218, by rotating the dose setting mechanism 216 relative to the housing 212. The user may verify that the appropriate dosage is selected by viewing the dosage amount indicated by the indicia visible through window 212a in the housing (see FIGS. 20A-20B). FIGS. 28A-28C show the injection device in a minimum dosage selection such that the ram 228 is rotated such that the wing 228b align with the shallowest slot 230b. In one embodiment, the medicament remaining in the fluid reservoir 218 following the injection is not delivered and may be discarded.

Referring to FIGS. 25A-25E, once the dosage is set by the user, the user removes the safety cap 214 from the front retainer 236 by pulling or twisting the safety cap 214 relative to the front retainer 236 (see FIG. 19C). Any priming is conducted if necessary, and the injection device 110 is ready for injection. The patient may then press the distal end of the guard 240 against their skin retracting the guard 240 proximally until the needle 222 penetrates the skin surface and the aperture 240a aligns with the retainer 230a.

Referring to FIGS. 25A-25E and 26A-26D, once the aperture 240a is aligned with the retainer 230a, the retainer 230a is radially released and the axial force of the latch on the retainer 230a pivots the projection 230c inwardly and out of the axial path of the latch 232 allowing the biasing member 226 to distally extend the latch 232, causing the ram 228 to urge the piston 220 distally and deliver the dose of medicament to the patient through the injection conduit 222. The shaft 216d may extend a sufficient distance in the distal direction so that the dose setting mechanism 216 remains rotatably fixed relative to the ram 228. Since the ram 228 is rotatably fixed by the wing's 228b engagement with the slot stop 230, the dose setting mechanism 216 is prevented from rotating in the fired position and ensuring that the dosage displayed through the window 212a is the dosage that was delivered. If the dose setting mechanism 216 did not remain coupled to the ram 228 in the fired position, then the dose setting mechanism 216 may be able to rotate relative to the ram 228 and cause confusion as to what dosage was delivered.

Referring to FIGS. 27A-27D, after the dose is delivered, the housing 212 is pulled away from the patient, pulling the needle 222 from the patient and allowing the biasing member 238 to urge the guard 240 distally past the end of the needle 222. A retaining member retains the guard 240 to lock the guard 240 relative to the needle 222 preventing further use of the injection device 210. The injection device 210 may then be safely discarded. An exemplary lock-out system is described below.

Referring to the drawings in detail, wherein like reference numerals indicate like elements throughout, there is shown in FIGS. 38A-42B a lock-out system for an injection device, generally designated 310, a third exemplary embodiment of the present invention. Various embodiments of the lock-out system are described in further detail below in reference to the exemplary embodiment shown in the figures. One or more of the embodiments discussed in reference to the lock-out system described below may be combined with one or more desirable features of the embodiments discussed in reference to the injection devices 110 and 210 described above.

Figure 40:
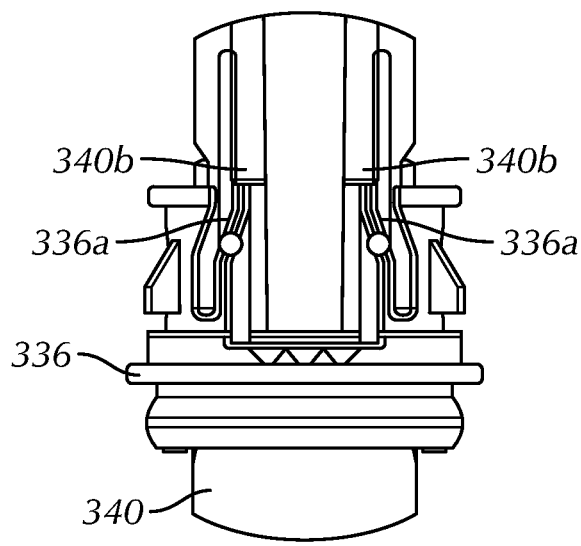
FIG. 40 is an enlarged side view of the front retainer retaining the guard shown within circle A of FIG. 38A.
Figure 41A:
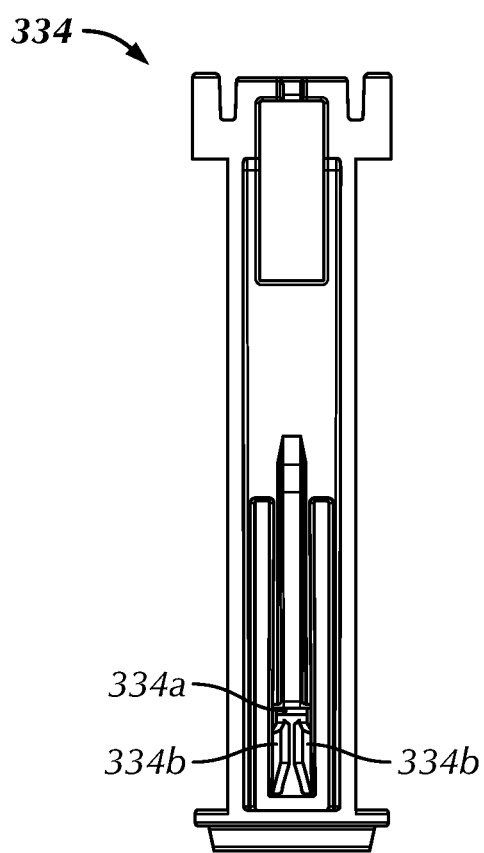
FIGS. 41A and 41B are side views of a sleeve of the injection device of FIGS. 38A and 38B.
Figure 41B:
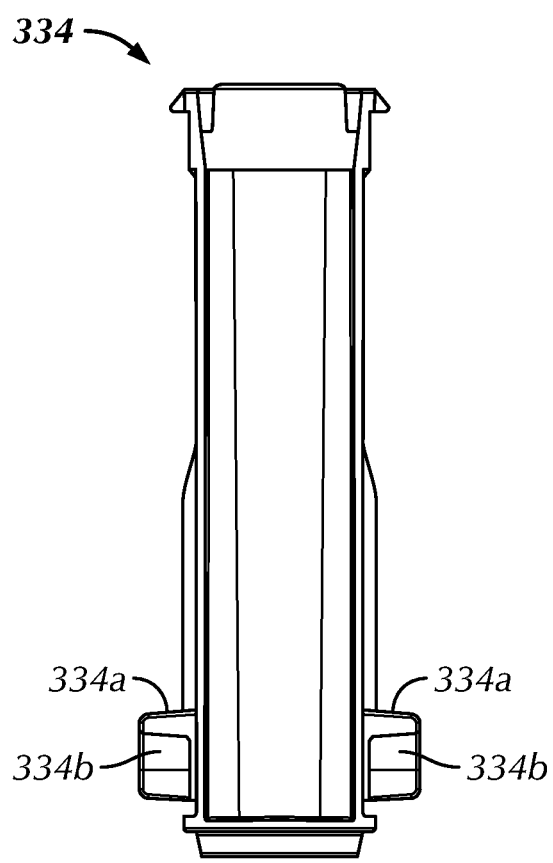

Referring to FIGS. 38A and 40, the front retainer 336, which is axially fixed relative to a housing and the fluid reservoir (not shown), may initially prevent the biasing member 338 (see FIGS. 43A and 43B) from distally extending the guard 340. The guard 340 however, may be free to retract relative to the front retainer 336 in the proximal direction. The front retainer 336 may include one or more arms 336a that engage with a corresponding stop 340b of the guard 340. In one embodiment, the front retainer 336 includes two pairs of arms 336a (the front pair of arms 336a being visible in the drawings).

Referring to FIGS. 38B, 39A, 41A and 41B, the injection device 310 may include a sleeve 334 fixed relative to the front retainer 336. The sleeve 334 may include a radial projection 334a. In one embodiment, the sleeve 334 includes a pair of diametrically opposed radial projections 334a (see FIG. 41B). In the initial position, the radial projection 334a may be positioned distally to the end of one or more arms 340a of the guard 340. The radial projection 334a may extend through a slot 340c in the guard 340. As the guard 340 is retracted during an injection, the slot 340c may be slid in a proximal direction relative to the radial projection 334a.

Figure 42:
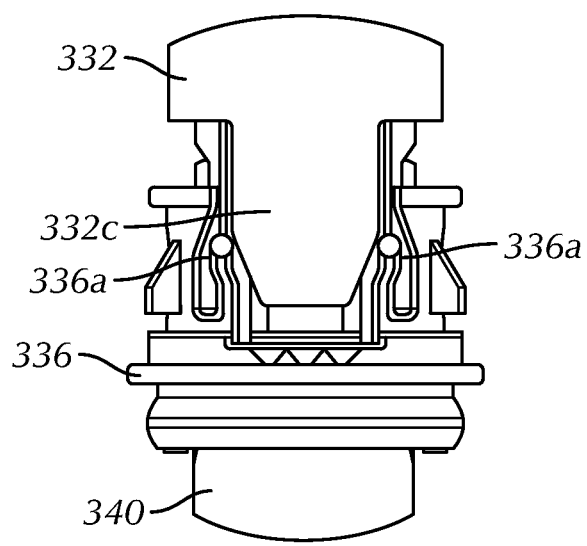
FIG. 42 is a side view of the front retainer and guard of FIG. 40 shown in a release position after the dose has been delivered.

Referring to FIG. 42, the latch may include one or more legs 332c. In one embodiment, the latch includes a pair of diametrically opposed legs 332c. The legs 332c may be tapered distally. Once the firing mechanism is actuated and the latch 332 is released, the latch 332 is fired distally by the biasing member 326 (see FIGS. 38A-38B). At the end of the delivery stroke, the legs 332c of the latch 332 engage with the arms 336a and flex the arms 335a out of the axial path of the stops 340b (see FIG. 40) of the guard 340.

Figure 43A:
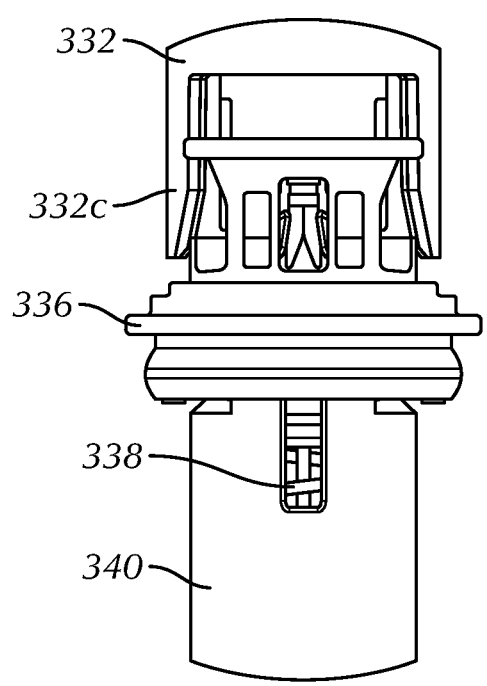
FIGS. 43A and 43B are side views of the guard, sleeve and front retainer and the guard and the sleeve respectively of the injection device of FIGS. 38A and 38B rotated 90 degrees from the view shown in FIG. 42 and with the guard extended and in the locked out position.
Figure 43B:
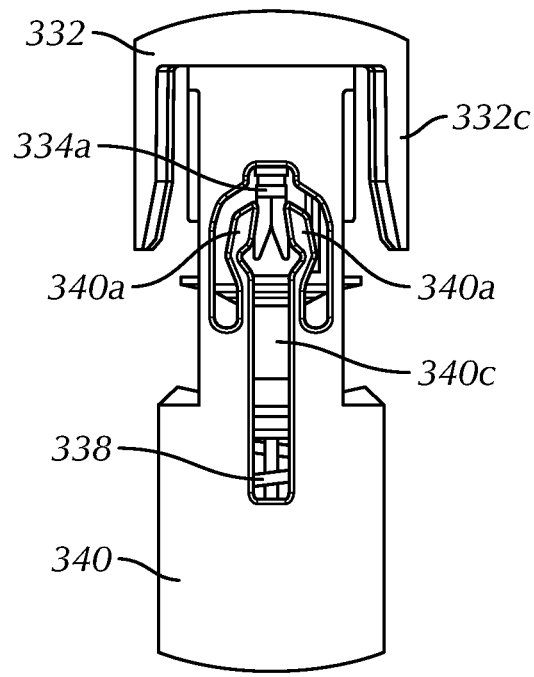

Referring to FIGS. 43A and 43B, once the arms 336a are disengaged from the stops 340b, the biasing member 338 extends the guard 340 distally to cover the end of the needle. As the guard 340 extends, the slot 340c of the guard is slid proximally relative to the radial projection 334a. As the guard 340 extends past the initial position of the guard 340, the arms 340a of the guard 340 extend over the radial projection 334a of the sleeve 334. As the arms 340a of the guard 340 extend over the radial projection 334a, the ends of the arms 340a flex away from one another until they engage with corresponding grooves 334*b* (see FIGS. 41A and 41B) and move closer to one another. The grooves 334*b* of the radial projection 334*a* are shaped to retain the arms 340*a* in the locked position and prevent the guard 340 from being urged in the proximal direction. In the locked position, the guard 340 is kept from being retracted in the proximal direction, preventing additional exposure or use of the needle. The guard 340 may extend axially past the end of the needle to in both the initial and locked positions. In one embodiment, the guard 340 is retracted to expose and allow insertion of the needle and is then extended to cover the needle. In one embodiment, the guard 340 extends further distally in the locked position relative to the end of the needle than in the initial position.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. An injection device for injecting medicament in a patient comprising:
    a housing configured to house a fluid reservoir having one of a plurality of volumes of medicament;
    an injection conduit fluidly coupled to the fluid reservoir defining a fluid pathway from the fluid reservoir to the patient;
    a firing mechanism coupled to the fluid reservoir and configured to expel the medicament from the fluid reservoir through the injection conduit;
    a volume setting mechanism coupled to the firing mechanism and configured to be adjusted to select the one of the plurality of volumes of medicament for the firing mechanism to expel;
    a dose setting mechanism configured to be adjusted to select a fraction of the one of the plurality of volumes of medicament that is injected from the injection conduit when the firing mechanism is actuated, and
    wherein the volume setting mechanism includes a nut and the firing mechanism includes a ram and a biasing member, the nut being threadably coupled to the ram, the nut being releaseably retained against a force of the biasing member in an initial position by a latch.

2. The injection device of claim 1, wherein the nut includes a plurality of indentations each configured to engage with a projection of the latch.

3. The injection device of claim 2, wherein each of the plurality of indentations includes a ring shaped groove extending circumferentially around the nut.

4. The injection device of claim 1 further comprising a guard that is slideably coupled to the housing, wherein the guard is configured to release the latch from the nut.

5. The injection device of claim 4 further comprising a second biasing member coupled to the guard and configured to bias the guard toward a distal end of the injection device, the guard configured to extend axially past the injection conduit.

6. The injection device of claim 5, wherein the guard extends further distally in a locked position than in an initial position.

7. The injection device of claim 1, wherein the nut is rotatable relative to the latch.

8. The injection device of claim 1, wherein the nut is configured to couple to the latch in one of a plurality of positions along an axial length of the nut, each of the plurality of positions along the axial length of the nut corresponding to one of the plurality of volumes of medicament for the firing mechanism to expel.

9. The injection device of claim 1, wherein the volume setting mechanism includes a ram extension threadably coupled to the ram, the ram extension configured to extend the length of the ram to one of a plurality of positions corresponding to one of the plurality of volumes of medicament for the firing mechanism to expel.

10. The injection device of claim 1, wherein the ram is rotatably fixed and axially moveable relative to the dose setting mechanism.

11. The injection device of claim 1, wherein the latch includes a latch arm releaseably retaining the nut in the initial position and a stop engaging the nut in a fired position, a distance between the latch arm and the stop being fixed.

12. The injection device of claim 1, wherein the firing mechanism includes a spring and the position of the spring being independent from the position of the dose setting mechanism.

13. The injection device of claim 1, wherein the dose setting mechanism includes a knob rotatably coupled to the housing.

14. The injection device of claim 1 further comprising a guard slideably coupled to the housing and configured to extend axially past the injection conduit and lock relative to the housing after removing the injection conduit from the patient.

15. The injection device of claim 1, wherein the injection conduit comprises a needle.

16. The injection device of claim 15 further comprising a syringe containing the fluid reservoir, wherein the needle is fixed to the syringe.

17. The injection device of claim 1, wherein the injection device is configured to prevent resetting after the firing mechanism is actuated so as to prevent a subsequent injection of the medicament by the injection device, thereby configuring the injection device as a single-use injector.

18. The injection device of claim 1, further comprising a safety cap coupled to the distal end of the housing, the safety cap being coupled to the firing mechanism such that decoupling the safety cap from the housing allows the firing mechanism to advance a predetermined distance relative to the fluid reservoir to prime the fluid reservoir.

19. The injection device of any of claim 1, wherein the firing mechanism is configured to deliver each of the selected fraction of the one of the plurality of volumes of medicament over a generally equal amount of time as compared to one another.

20. The injection device of claim 1, wherein the fraction is only greater than or equal to 0.5.

21. The injection device of any of claim 1, wherein the selected fraction results in a residual volume remaining in the fluid reservoir after delivery of 0.18 ml or less.

22. An injection device for injecting medicament in a patient comprising:
a housing configured to house a fluid reservoir having one of a plurality of volumes of medicament;
an injection conduit fluidly coupled to the fluid reservoir defining a fluid pathway from the fluid reservoir to the patient;
a firing mechanism coupled to the fluid reservoir and configured to expel the medicament from the fluid reservoir through the injection conduit;
a volume setting mechanism coupled to the firing mechanism and configured to be adjusted to select the one of the plurality of volumes of medicament for the firing mechanism to expel;
a dose setting mechanism configured to be adjusted to select a fraction of the one of the plurality of volumes of medicament that is injected from the injection conduit when the firing mechanism is actuated, and
wherein actuating the dose setting mechanism advances the firing mechanism a predetermined distance relative to the fluid reservoir to prime the fluid reservoir.

23. The injection device of claim 22, wherein the volume setting mechanism includes a nut and the firing mechanism includes a ram and a biasing member, the nut being threadably coupled to the ram, the nut being releaseably retained against a force of the biasing member in an initial position by a latch.

24. The injection device of claim 22, wherein the nut includes a plurality of indentations each configured to engage with a projection of the latch.

25. The injection device of claim 24, wherein each of the plurality of indentations includes a ring shaped groove extending circumferentially around the nut.

26. The injection device of claim 22 further comprising a guard that is slideably coupled to the housing, wherein the guard is configured to release the latch from the nut.

27. The injection device of claim 26 further comprising a second biasing member coupled to the guard and configured to bias the guard toward a distal end of the injection device, the guard configured to extend axially past the injection conduit.

28. The injection device of claim 27, wherein the guard extends further distally in a locked position than in an initial position.

29. The injection device of claim 22, wherein the nut is rotatable relative to the latch.

30. The injection device of claim 22, wherein the nut is configured to couple to the latch in one of a plurality of positions along an axial length of the nut, each of the plurality of positions along the axial length of the nut corresponding to one of the plurality of volumes of medicament for the firing mechanism to expel.

31. The injection device of claim 22, wherein the volume setting mechanism includes a ram extension threadably coupled to the ram, the ram extension configured to extend the length of the ram to one of a plurality of positions corresponding to one of the plurality of volumes of medicament for the firing mechanism to expel.

32. The injection device of claim 22, wherein the ram is rotatably fixed and axially moveable relative to the dose setting mechanism.

33. The injection device of claim 22, wherein the latch includes a latch arm releaseably retaining the nut in the initial position and a stop engaging the nut in a fired position, a distance between the latch arm and the stop being fixed.

34. The injection device of claim 22, further comprising a safety cap coupled to the distal end of the housing, the safety cap being coupled to the firing mechanism such that decoupling the safety cap from the housing allows the firing mechanism to advance a predetermined distance relative to the fluid reservoir to prime the fluid reservoir.

35. The injection device of claim 22, wherein the injection device is configured to prevent resetting after the firing mechanism is actuated so as to prevent a subsequent injection of the medicament by the injection device, thereby configuring the injection device as a single-use injector.

36. An injection device for injecting medicament in a patient comprising:
a firing mechanism having an actuator and a ram, the firing mechanism configured to be selectively preset during assembly to one of a plurality of positions based on a maximum volume of medicament to be delivered to the patient;
a dose setting mechanism configured to be selectably adjusted upon use, independent of the preset of the firing mechanism, to select a fraction of the maximum volume of medicament to be delivered to the patient; and
a volume setting mechanism including a nut threadably coupled to the ram, the nut being releaseably retained against a force of the actuator in an initial position by a latch.

37. An injection device for injecting medicament in a patient comprising:
a housing configured to house a fluid container having a piston and a fluid reservoir having one of a plurality of volumes of medicament, the fluid container including an injection conduit fluidly coupled to the fluid reservoir defining a fluid pathway from the fluid reservoir to the patient;
a ram coupled to the piston and configured to expel the medicament from the fluid reservoir through the injection conduit;
a spring biasing the ram toward the fluid container in an initial position;
a nut threadably coupled to the ram, the nut having a plurality of ring shaped grooves or projections;
a latch fixed relative to the housing and engaging a predetermined one of the plurality of ring shaped grooves or projections to retain the ram in one of a plurality of axial positions against a force of the spring in the initial position, the nut being rotatable relative to the latch in the initial position; and
a dose setting knob rotatably coupled to the housing and rotatably fixed and axially moveable relative to the ram in the initial position.

38. An injection device for injecting medicament in a patient comprising:

a housing configured to house a fluid container having a piston and a fluid reservoir having one of a plurality of volumes of medicament, the fluid container including an injection conduit fluidly coupled to the fluid reservoir configured to define a fluid pathway from the fluid reservoir to the patient;

a ram coupled to the piston and configured to expel the medicament from the fluid reservoir through the injection conduit, the ram having a radially extending wing;

a latch axially fixed and rotatably moveable relative to the ram, the ram having a plurality of radial features;

a spring biasing the latch toward the fluid container in an initial position;

a retainer fixed relative to the housing and engaging a predetermined one of the plurality of radial features to retain the ram in one of a plurality of axial positions against a force of the spring in the initial position;

a stop having a plurality of axially extending and radially projecting slots each extending a different axial depth, the ram being rotatably to align the wing with one of the plurality of slots in the initial position and the wing configured to engage the one of the plurality of slots in a fired position; and a dose setting knob rotatably coupled to the housing, the ram being rotatably fixed and axially moveable relative to the dose setting knob.

39. A method for assembling an injection device comprising:

inserting a fluid container having a fluid reservoir including one of a plurality of volumes of medicament into a housing, the fluid container including an injection conduit fluidly coupled to the fluid reservoir configured to define a fluid pathway from the fluid reservoir to the patient;

setting a volume setting mechanism based on a size of the one of the plurality of volumes of medicament;

coupling the volume setting mechanism to a firing mechanism, the firing mechanism including a ram and a biasing member,; and coupling the firing mechanism to the fluid reservoir, the firing mechanism configured to expel the medicament from the fluid reservoir through the injection conduit, the firing mechanism being coupled to a dose setting mechanism configured to select all or a fraction of the one of the plurality of volumes of medicament that is injected from the injection conduit when the firing mechanism is actuated, wherein the volume setting mechanism includes a nut threadably coupled to the ram and the nut is releaseably retained against a force of the biasing member in an initial position by a latch and setting the volume setting mechanism includes adjusting the position of the nut relative to the ram.

* * * * *